(12) United States Patent
Fraser et al.

(10) Patent No.: US 9,074,129 B2
(45) Date of Patent: Jul. 7, 2015

(54) MECHANOCHROMIC LUMINESCENT DIFLUOROBORON BETA-DIKETONATES

(75) Inventors: Cassandra L. Fraser, Charlottesville, VA (US); Guoqing Zhang, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 5 days.

(21) Appl. No.: 13/512,052

(22) PCT Filed: Dec. 1, 2010

(86) PCT No.: PCT/US2010/003074
§ 371 (c)(1),
(2), (4) Date: May 2, 2013

(87) PCT Pub. No.: WO2011/068537
PCT Pub. Date: Jun. 9, 2011

(65) Prior Publication Data
US 2013/0210053 A1    Aug. 15, 2013

Related U.S. Application Data

(60) Provisional application No. 61/265,404, filed on Dec. 1, 2009, provisional application No. 61/309,247, filed on Mar. 1, 2010.

(51) Int. Cl.
| | |
|---|---|
| *C09K 11/06* | (2006.01) |
| *C07F 5/02* | (2006.01) |
| *C09B 23/14* | (2006.01) |
| *C09B 57/10* | (2006.01) |

(52) U.S. Cl.
CPC . *C09K 11/06* (2013.01); *C07F 5/02* (2013.01); *C09K 2211/1007* (2013.01); *C09K 2211/1096* (2013.01); *C09B 23/141* (2013.01); *C09B 57/10* (2013.01)

(58) Field of Classification Search
CPC ...................................................... C09K 11/06
USPC ...................................... 546/13; 252/301.16
See application file for complete search history.

(56) References Cited

U.S. PATENT DOCUMENTS

| | | | |
|---|---|---|---|
| 3,567,439 A | 3/1971 | Daniel et al. | |
| 4,123,268 A * | 10/1978 | Halm | 430/83 |
| 4,394,428 A | 7/1983 | Van Allan | |
| 4,552,825 A | 11/1985 | Chen et al. | |
| 5,433,896 A | 7/1995 | Kang et al. | |
| 6,916,894 B2 | 7/2005 | Cammack et al. | |
| 7,955,861 B2 | 6/2011 | Fraser et al. | |
| 2009/0137057 A1 | 5/2009 | Fraser et al. | |
| 2013/0210053 A1 | 8/2013 | Fraser et al. | |

FOREIGN PATENT DOCUMENTS

| | | |
|---|---|---|
| JP | 2000030869 | 1/2000 |
| JP | 2000336045 | 12/2000 |
| JP | 2007502106 | 3/2007 |
| WO | WO9604249 | 2/1996 |
| WO | WO02078444 | 10/2002 |
| WO | WO2005046595 | 5/2005 |
| WO | WO2008054824 | 5/2008 |

OTHER PUBLICATIONS

Mirochnik, A. G. Fluorescence and photochemical properties of crystalline boron difluorides β-diketonato. Russian Chemical Bulletin. 49(6), 2000, 1024-1027.*
Liu, Tiandong, et al., "Arene effects of difluoroboron β-diketonate mechanochromic luminescence", J. Mater. Chem., 2011, 21, 8401-8408.
Liu, Tiandong, et al., "Arene effects of difluoroboron β-diketonate mechanochromic luminescence", J. Mater. Chem., 2011, 21, 8401-8408. Amendment published Jul. 4, 2011.
Liu, Tiandong, et al., "Arene effects of difluoroboron β-diketonate mechanochromic luminescence", J. Mater. Chem., 2011, 21, 8401-8408. Supplemental Material (ESI) for J. of Mat. Chem.
Nguyen, N., et al., "Alkyl chain length effects on solid-state difluoroboron β-diketonate mechanochromic luminescence", J. Mater. Chem. 2011, 21, 8409-8415.
Nguyen, N., et al., "Alkyl chain length effects on solid-state difluoroboron β-diketonate mechanochromic luminescence", J. Mater. Chem. 2011, 21, 8409-8415, Supplementary Material (ESI) for J. of Mat. Chem.
Zhang, G., et al., "Polymorphism and Reversible Mechanochromic Luminescence for Solid-State Difluoroboron Avobenzone", J. Am. Chem. Soc., 2010, 132, 2160-2162.
Zhang, G., et al., "Polymorphism and Reversible Mechanochromic Luminescence for Solid-State Difluoroboron Avobenzone", J. Am. Chem. Soc., 2010, 132, 2160-2162. Supporting Information.

(Continued)

*Primary Examiner* — Samantha Shterengarts
(74) *Attorney, Agent, or Firm* — Rodney L. Sparks

(57) ABSTRACT

The invention provides luminescent solid-state compositions comprising difluoroboron beta-diketonates wherein the compositions can exhibit mechanochromic luminescence. The mechanochromic effect on the luminescence can be reversible, such as thermally reversible. Various solid-state forms of the invention can have emission spectra that differ from the properties of the respective difluoroboron beta-diketonate in solution. The mechanochromic effect can be stimulated by pressure such as handwriting, and can be reversed over a period of minutes to hours at room temperature. The invention also provides methods of making and methods of using the solid-state compositions, such as for sensors and for information displays for use in biological sensing, and in art, design, and consumer products. Compositions of the invention, such as compositions in nanoparticulate form, or contained within a matrix material, can be used in conjunction with fluorescence microscopy to provide information concerning pressures and tensions within and external to living cells, tissues, or organisms.

27 Claims, 19 Drawing Sheets

(56) References Cited

OTHER PUBLICATIONS

Zhang, G., et al., "Reversible solid-state mechanochromic fluorescence from a boron lipid dye", J. Mater. Chem., 2011, 21, 8295-8299.

Zhang, G., et al., "Mechanochromic Luminescence Quenching: Force-Enhanced Singlet-to-Triplet Intersystem Crossing for Iodide-Substituted Difluoroboron-Dibenzoylemethane-Dodecane in the Solid State", Inorg. Chem. 2010, 49, 10747-10749.

Zhang, G., et al., "Multi-Emassive Difluoroboron Dibenzoylmethane Polylactide Exhibiting Intense Fluorescence and Oxygen-Sensitive Room-Temperature Phosphorescence", J. Am. Chem. Soc., 2007, 129—8942-8943.

Zhang, G., et al., "Multi-Emassive Difluoroboron Dibenzoylmethane Polylactide Exhibiting Intense Fluorescence and Oxygen-Sensitive Room-Temperature Phosphorescence", J. Am. Chem. Soc., 2007, 129—8942-8943. Supporting Information.

Zhang, G., et al., "Multi-Emassive Difluoroboron Dibenzoylmethane Polylactide Exhibiting Intense Fluorescence and Oxygen-Sensitive Room-Temperature Phosphorescence", Additions and Corrections, J. Am. Chem. Soc., 2007, 129, 15728.

Zhang, G., et al., "Emission Color Tuning with Polymer Molecular Weight for Difluoroboron Dibenzoylmethane-Polylactide", Adv. Mat., 2008, 20, 1-6.

Zhang, G., et al., "Emission Color Tuning with Polymer Molecular Weight for Difluoroboron Dibenzoylmethane-Polylactide", Adv. Mat., 2008, 20, 1-6. Supporting Information.

Pfister, A., et al., "Boron Polylactide Nanoparticles Exhibiting Fluorescence and Phosphorescence in Aqueous Medium", ACS Nano, vol. 2, No. 6, 1252-1258. Jun. 2008.

Zhang, G., et al., "Synthesis and Fluorescent Properties of Difluoroboron Dibenzoylmethane Polycaprolactone", Macromolecules, 2009, 42, 3092-2097.

Zhang, G., et al., "Difluoroboron Dibenzoylmethane PCL-PLA Block Copolymers: Matrix Effects on Room Temperature Phosphorescence", Macromolecules, 2009, 42, 3162-3169.

Zhang, G., et al., "A dual-emissive-materials design concept enables tumour hypoxia imaging", Nature Materials, vol. 8, Sep. 2009, 747-751.

Zhang, G., et al., "A dual-emissive-materials design concept enables tumour hypoxia imaging", Nature Materials, vol. 8, Sep. 2009, 747-751. Supplementary Information DOI:10.1039/MNAT2509. 1-7.

Fraser, C., et al., "Boron PLA for oxygen sensing & hypoxia imaging", Materials Today, Oct. 2009, vol. 12, No. 10, 48-50.

Zhang, G., et al., "Role of Boron in the Polymer Chemistry and Photophysical Properties of Difluoroboron-Dibenzoylmethane Polylactide", Macromolecules 2009, 42, 8627-8633.

Cogne-Laage, E., et al., "Diaroyl(methanato)boron Difluoride Compounds as Medium-Sensitive Two-Photon Fluorescent Probes", Chem. Eur. J. 2004, 10, 1445-1455.

Bender, J., "Site-Isolated Luminescent Europium Complexes with Polyester Macroligands: Metal-Centered Heteroarm Stars and Nanoscale Assemblies with Labile Block Junctions", J. Am. Chem. Soc., 2002, 124, 8526-8527.

Bender, J., "Site-Isolated Luminescent Europium Complexes with Polyester Macroligands: Metal-Centered Heteroarm Stars and Nanoscale Assemblies with Labile Block Junctions", J. Am. Chem. Soc., 2002, 124, 8526-8527. Supporting Information S1-S4.

Costela, A., "Efficient and highly photostable solid-state dye lasers based on modified dipyrromethene.BF2 complexes incorporated into solid matrices of poly(methyl methacrylate)", App. Phys. B 76, 365-369, 2003.

Han, L., et al., "High Efficiency of Dye-Sensitized Solar Cell and Module", IEEE, 2006, 179-182.

Chow, Y., et al., "Spectroscopic and Electrochemical Properties of 1,3-Diketonatoboron Derivatives", J. of Phys. Org. Chem., V. 9, 7-16 (1996).

\* cited by examiner

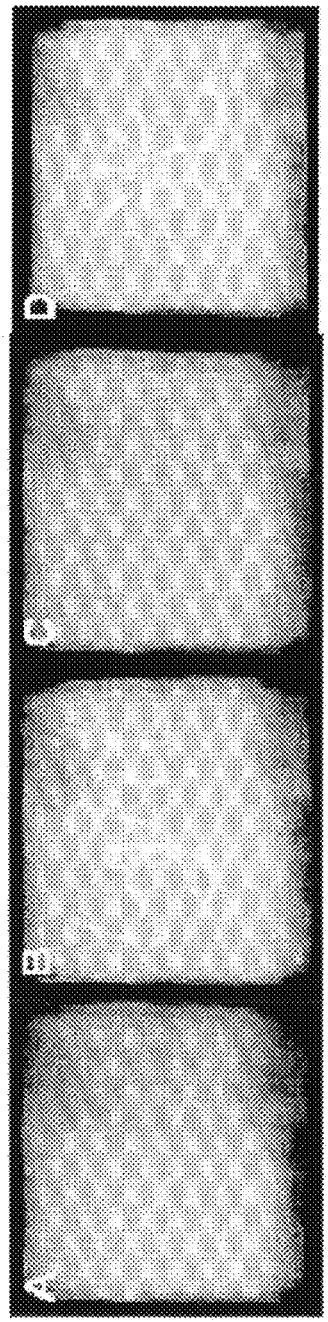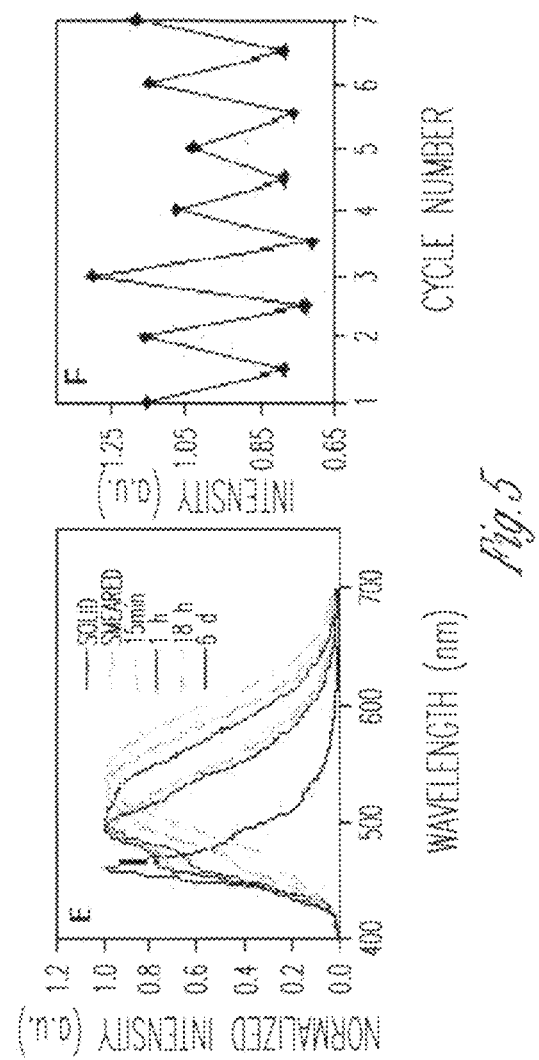
Fig. 5

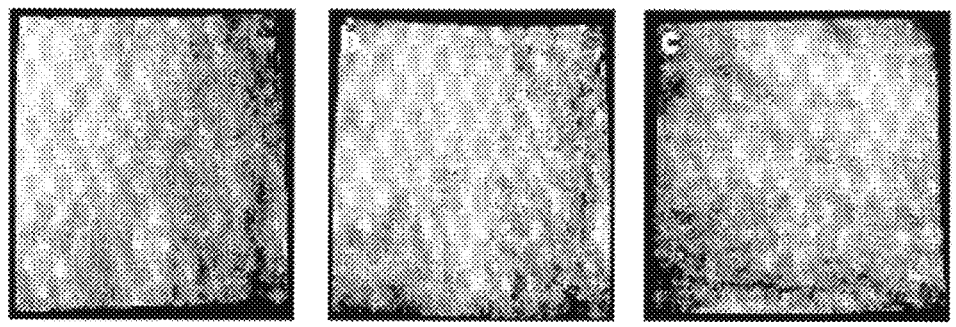
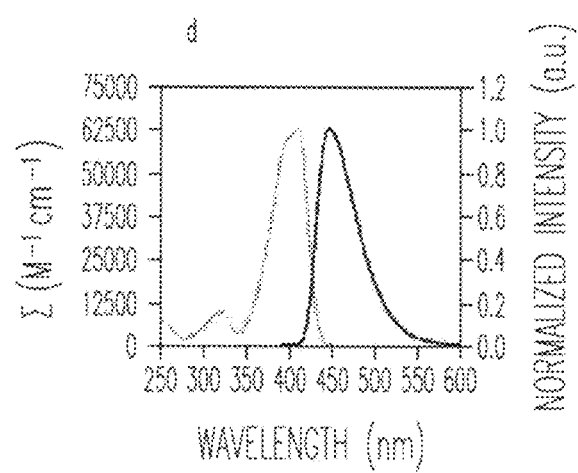
Fig. 8

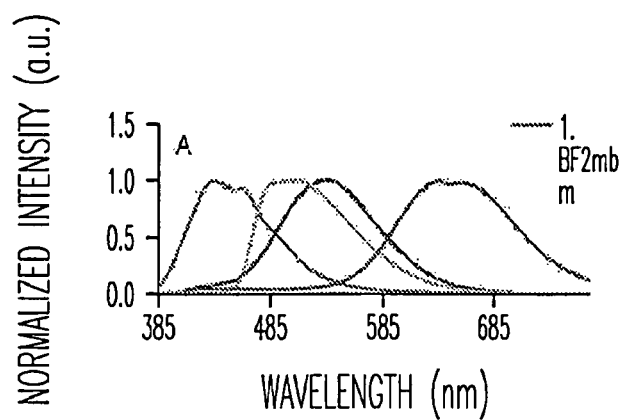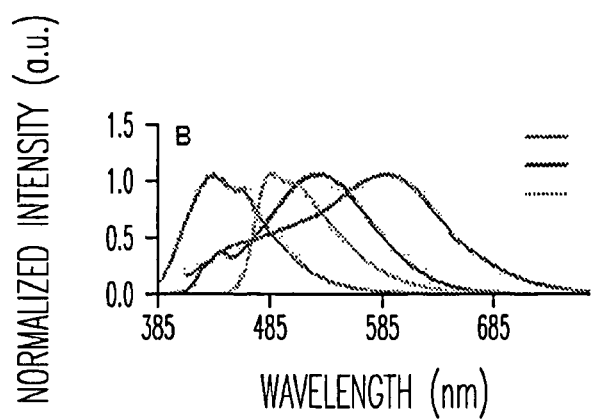
Fig. 11

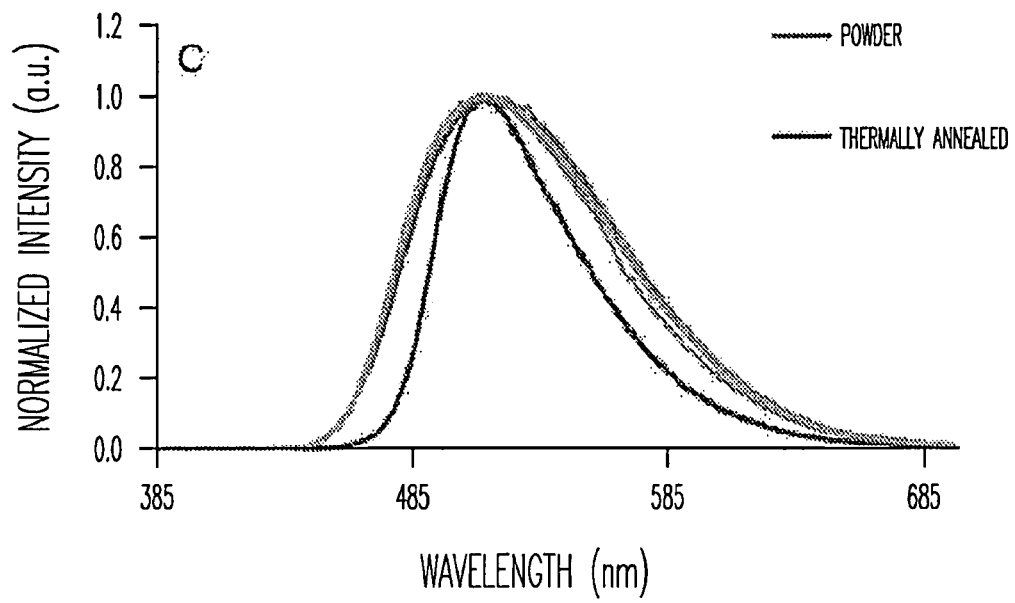
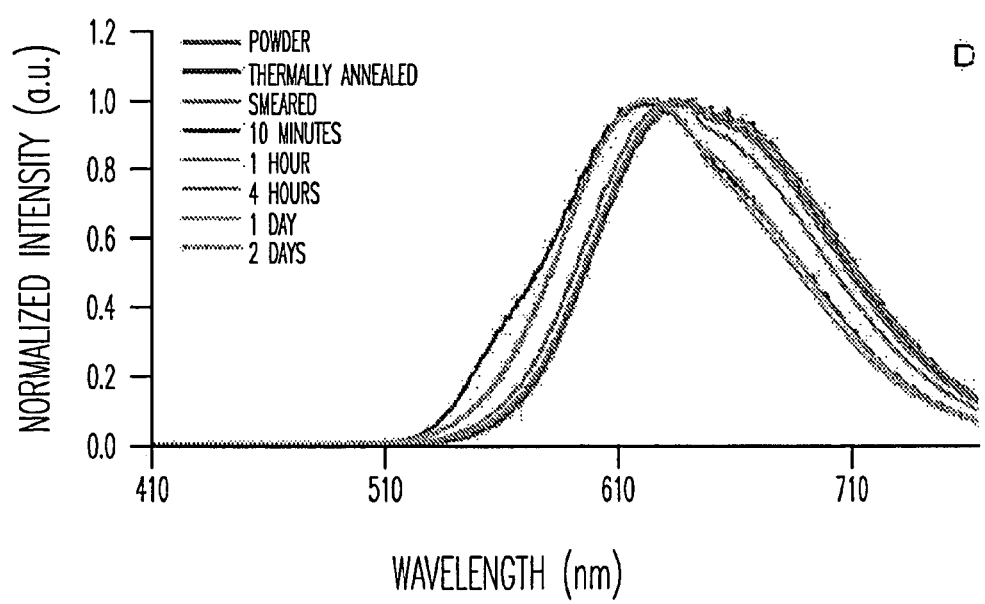
Fig.12 (CONT.)

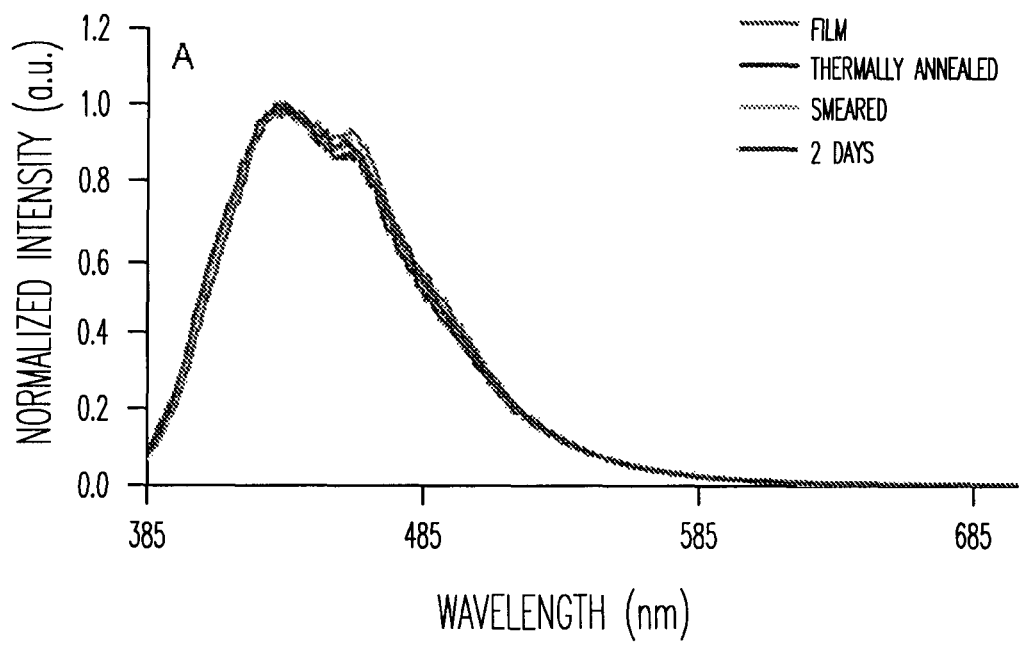
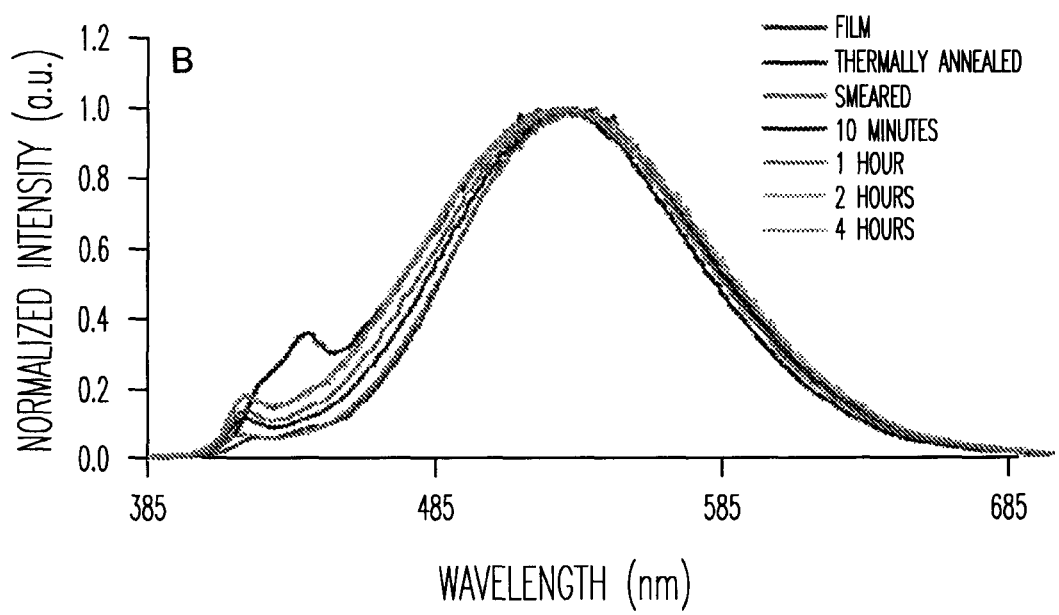
Fig. 13

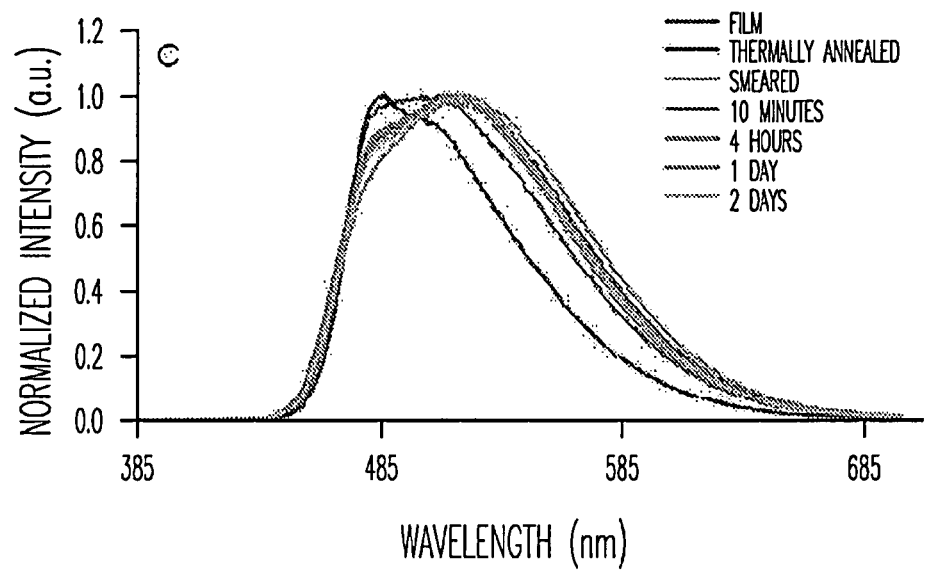
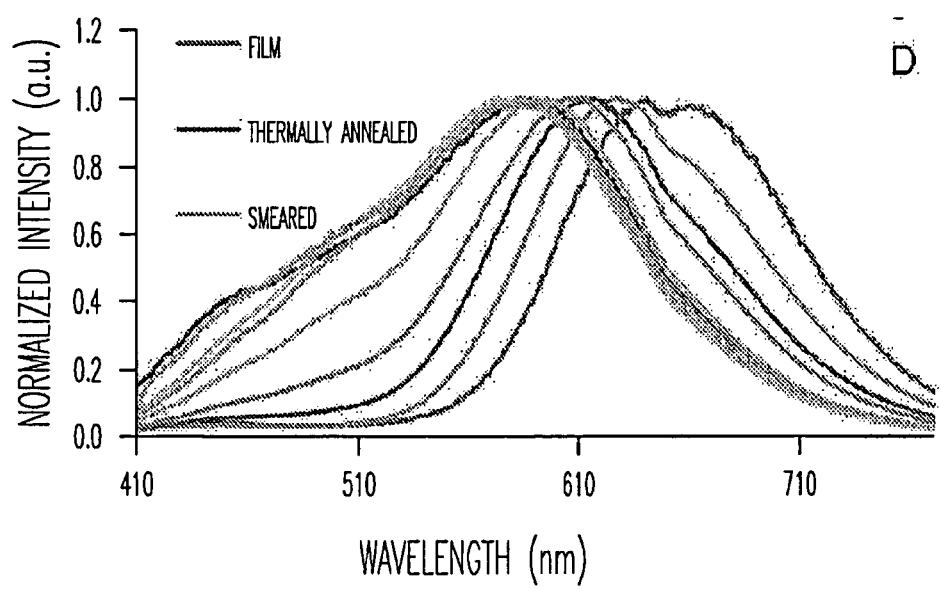
Fig. 13 (CONT.)

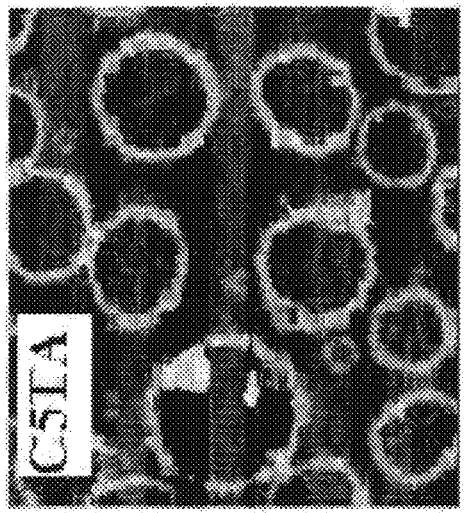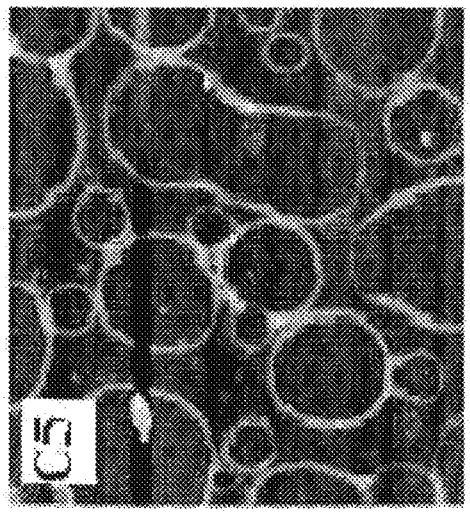
Fig. 14

MECHANOCHROMIC LUMINESCENT DIFLUOROBORON BETA-DIKETONATES

CROSS-REFERENCE TO RELATED APPLICATIONS

This application is a national stage filing of International Application No. PCT/US2010/003074, filed Dec. 1, 2010, which claims the priority under 35 U.S.C. §119(e) of U.S. Ser No. 61/265,404, filed Dec. 1, 2009, and of U.S. Ser. No. 61/309,247, filed Mar. 1, 2010, the disclosures of which are incorporated by reference in their entireties.

STATEMENT OF GOVERNMENT SUPPORT

This invention was made with government support under grant number CHE 0718879 awarded by the National Science Foundation. The government has certain rights in the invention.

BACKGROUND

Metal-free organic dyes that luminesce in the solid state are not common but have important applications in fields such as display technologies, sensing, nano-patterning, and solid-state lasers. Lately, new compounds such as dicyanopyrazines, 5-aryl-2,2'-bipyridyls, diazepines, heterocyclic quinol fluorophores, 2-aryl-3-hydroxyquinolones, fumaronitriles, dithienopyrroles, oxadiazoles, diborylphenylenes, pyrones, and perylenediimides have been reported to show solid-state fluorescence. However, many of these systems are synthetically complicated and employ materials that have limited industrial potential.

See for example:
Forrest, S. R.; Thompson, M. E. *Chem. Rev.* 2007, 107, 923-925.
Yang, J.-S.; Swager, T. M. *J. Am. Chem. Soc.* 1998, 120, 11864-11873.
Menard, E.; Meitl, M. A.; Sun, Y.; Park, J.-U.; Shir, D. J.-L.; Nam, Y.-S.; Jeon,
S.; Rogers, J. A. *Chem. Rev.* 2007, 107, 1117-1160.
Samuel, I. D. W.; Turnbull, G. A. *Chem. Rev.* 2007, 107, 1272-1295.
Park, S.-Y.; Ebihara, M.; Kubota, Y.; Funabiki, K.; Matsui, M. *Dyes Pigm.* 2009, 82, 258-267.
Karlsson, I.; Hillerström, L.; Stenfeldt, A.-L.; Mårtensson, J.; Börje, A. *Chem. Res. in Toxicol* 2009, 22, 1881-1892.
Chatelain, E.; Gabard, B. *Photochem. Photobiol.* 2001, 74, 401-406.
Barry, J.; Fritz, M.; Brender, J. R.; Smith, P. E. S.; Lee, D.-K.; Ramamoorthy, A. *J. Am. Chem. Soc.* 2009, 131, 4490-4498.
Ran, C.; Xu, X.; Raymond, S. B.; Ferrara, B. J.; Neal, K.; Bacskai, B. J.;
Medarova, Z.; Moore, A. *J. Am. Chem. Soc.* 2009, 131, 15257-15261.

The solid-state fluorescence of organic molecules strongly depends on the molecular structure and intermolecular interactions present in different morphologies. Various emission colors may be achieved from the same fluorophore by taking advantage of material polymorphism, which is controllable by processing methods. See, for example:
Schwoerer, M.; Wolf, H. C. *Organic Molecular Solids*, WILEY-VCH, Weinheim, 2007;
Mutai, T.; Satou, H.; Araki, K. *Nat. Mater.* 2005, 4, 685-7;
Zhang, H.; Zhang, Z.; Ye, K.; Zhang, J.; Wang, Y. *Adv. Mater.* 2006, 18, 2369-72;
Mizukami, S.; Houjou, H.; Sugaya, K.; Koyama, E.; Tokuhisa, H.; Sasaki, T.; Kanesato, M. *Chem. Mater.* 2005, 17, 50-6;
Kohmoto, S.; Tsuyuki, R.; Masu, H.; Azumaya, I.; Kishikawa, K. *Tetrahedron* Lett. 2008, 49, 39-43.

Another more unusual strategy involves force-induced emission color changes, or mechanochromic luminescence. Ito et al. (Ito, H.; Saito, T.; Oshima, N.; Kitamura, N.; Ishizaka, S.; Hinatsu, Y.; Wakeshima, M.; Kato, M.; Tsuge, K.; Sawamura, M. *J. Am. Chem. Soc.* 2008, 130, 10044-5) reported that the photoluminescence of $[(C_6F_5Au)_2(\mu\text{-}1,4\text{-diisocyanobenzene})]$ can be switched from blue to yellow by grinding the solid. Ordered aggregates and an amorphous solid are believed to be responsible for the blue-shifted and red-shifted emission colors, respectively. Mechanochromic luminescence has also been attributed to the disruption of hydrogen bonding, resulting in a less ordered polymorph (Sagara, Y.; Mutai, T.; Yoshikawa, I.; Araki, K. *J. Am. Chem. Soc.* 2007, 129, 1520-1). More recently, Chung et al. (Chung, J. W.; You, Y.; Huh, H. S.; An, B.-K.; Yoon, S.-J.; Kim, S. H.; Lee, S. W.; Park, S. Y. *J. Am. Chem. Soc.* 2009, 131, 8163-72) reported fluorescence "turn on" by either UV irradiation or shear force for a cyanostilbene system.

Mechanochromic luminescence is rare, and to our knowledge systems such as we disclose and claim below, that are reversible at room temperature, are unprecedented. For previously described systems, redissolving the ground solid and drying, heating, exposure to solvent vapor or other methods were required to erase the marks and revert to the initial, ordered state. For examples see: Sagara, Y.; Kato, T. "Mechanically Induced Luminescence Changes in Molecular Assemblies" *Nat. Chem.* 2009, 1, 605-10.

SUMMARY

The invention in various embodiments is directed to compositions comprising mechanochromic luminescent (ML) solid-state forms of difluoroboron β-diketonate (2,2-difluoro-1,3,2-dioxaborazine) derivatives, which can be reversibly mechanochromic; to methods of generating mechanochromic luminescent surfaces and materials incorporating the compositions, including rewritable surfaces; to display devices incorporating the optionally rewritable mechanochromic luminescent surfaces; to biological probes comprising, for example, nanoparticulate forms of the compositions useful for making in vivo measurements of tension and pressure; and to art, design, forensic, intelligence, and consumer products incorporating the compositions.

In various embodiments, the invention provides a composition comprising a mechanochromic luminescent solid-state form of a difluoroboron β-diketonate of formula (I)

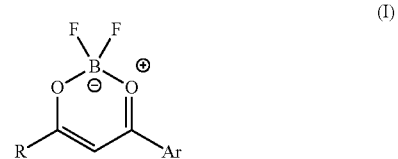

wherein
R is alkyl, alkenyl, alkynyl, cycloalkyl, or cycloalkylalkyl, wherein any alkyl, alkenyl, alkynyl, cycloalkyl, or cycloalkylalkyl is optionally substituted with 1-5 independently selected J groups; or R is Ar; wherein each Ar is an independently selected aryl, arylalkenyl, arylalkynyl, heteroaryl, heteroarylalkenyl, or heteroarylalkynyl group, wherein any aryl or heteroaryl can be monocyclic or polycyclic, and is optionally substituted with 1-5 independently selected J groups;

J is F, Cl, Br, I, OR', OC(O)N(R')$_2$, CN, NO, NO$_2$, ONO$_2$, N$_3$, CF$_3$, OCF$_3$, R', N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J;

or any salt thereof.

In various embodiments, the invention provides a method of preparing the luminescent solid-state compositions of the invention comprising forming a solution in an organic solvent of a compound of formula (I), then removing the solvent, for example, by evaporation; or comprising spreading a solid crystalline or amorphous form of the compound of formula (I) on a surface.

In various embodiments, the invention provides a mechanochromic luminescent solid state display or display device comprising the composition of the invention or a composition prepared by the method of the invention, wherein the display optionally includes a system for illumination, such as with ultraviolet (UV) light.

In various embodiments, the invention provides a biological probe system comprising the composition of the invention or a composition prepared by the method of the invention wherein a luminescence emission of the composition provides information about a biological environment in a cell or tissue or intact organism, such as nanoparticles disposed in vivo and observed with a fluorescence microscopy system.

In various embodiments, the invention provides a kit for forensic detection, for example for detection of fingerprints or other biological or chemical samples deposited on a surface, comprising a solid-state composition of the invention or a composition prepared by the method of invention and, optionally, an application system and/or a UV light source.

In various embodiments, the invention provides a compound of formula (I) as disclosed and claimed herein.

In various embodiments, the invention provides a solid-state mechanochromic luminescent composition comprising a difluoroboron β-diketonate composition of formula (I) and a second light-absorbing or luminescing material. The presence of the second light-absorbing or luminescent material can alter the luminescence properties of the composition relative to the luminescence properties of the difluoroboron β-diketonate of formula (I).

In various embodiments, the invention provides a solid-state mechanochromic luminescent composition comprising a β-diketone composition of formula (II) and a second light-absorbing or luminescing material. The presence of the second light-absorbing or luminescent material can alter the luminescence properties of the composition relative to the luminescence properties of the difluoroboron β-diketone of formula (II).

BRIEF DESCRIPTION OF THE FIGURES

FIG. 5 shows the fluorescence emission ($\lambda_{ex}$=365 nm) of a thermally annealed BF$_2$AVB solid film: (A) on a piece of weighing paper; (B) the mechanochromic luminescence image of the word "light" written with a cotton swab tip on the BF$_2$AVB film deposited on the weighing paper; (C) a display of the reversible mechanochromic effect with original emission spectrum restored by heating the film with a heat gun for ~3-5 s, and (D) a display of the rewritable mechanochromic fluorescence demonstrated by the Chinese character "light" written with a cotton swab tip on the restored film shown in (C); (E) a luminescence emission spectra of BF$_2$AVB blue solid and the smeared solid film on a quartz substrate monitored over time after smearing; and (F) the luminescence intensity monitored at 535 nm versus smearing/thermal erasing cycle number.

FIG. 8 shows mechanochromic luminescence of BF$_2$dbmOC$_{12}$H$_{25}$ on a piece of weighing paper, wherein the solid-state composition has been put under mechanical pressure by scratching; the scratched region luminescing under UVA light in (8b) appears yellow orange. Image (8a) was taken prior to scratching and (8c) shows erasure of the writing by brief thermal annealing. FIG. (8d) shows the absorption and emission spectra of BF$_2$dbm(I)OC$_{12}$H$_{25}$ in CH$_2$Cl$_2$ solution.

FIG. 11 shows solid-state emission spectra of amorphous films of difluorodioxaborazine compounds $BF_2mbm$, $BF_2dbm$, $BF_2nbm$, and $BF_2abm$, spincast from $CH_2Cl_2$ solutions (1 mg/mL) onto glass; (A): before thermal annealing; (B): after thermal annealing.

FIG. 13 shows normalized emission spectra of amorphous $BF_2mbm$, $BF_2dbm$, $BF_2nbm$, and $BF_2abm$ on cover glass: (A) $BF_2mbm$, $\lambda_{ex}$=369 nm; (B) $BF_2dbm$, $\lambda_{ex}$=369 nm; (C) $BF_2nbm$, $\lambda_{ex}$=369 nm; (D) $BF_2abm$, $\lambda_{ex}$=397 nm.

FIG. 14 shows images of as-spun (left) and thermally annealed (TA) (right) compound $C_5$ spin-cast films.

DETAILED DESCRIPTION

Definitions

Figure 1:
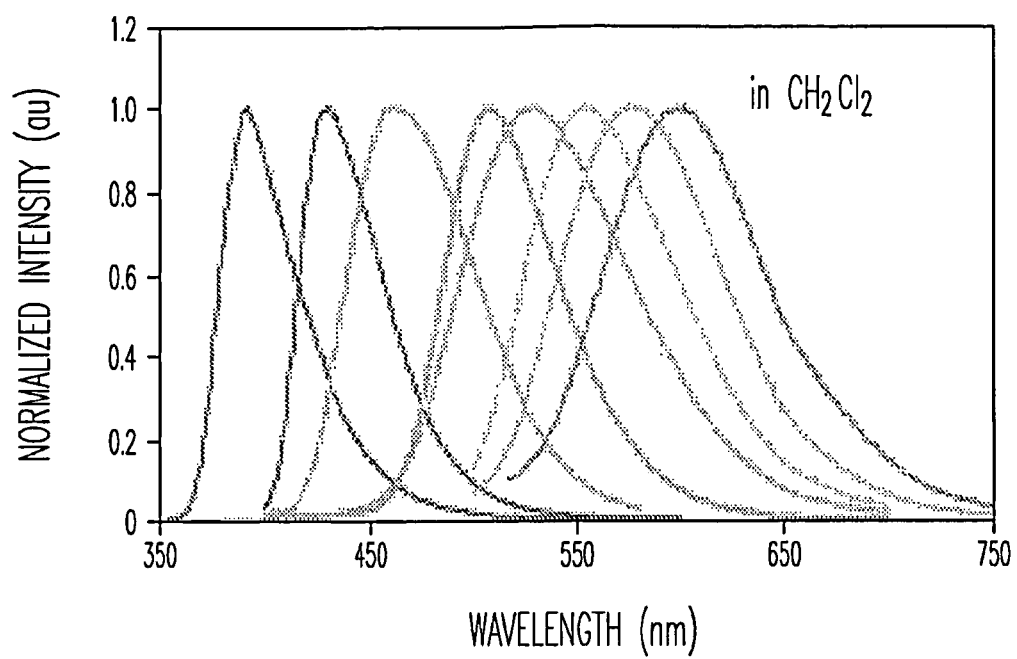
FIG. 1 shows luminescence emission color tuning. Fluorescence spectra of compounds 1-8 in CH$_2$Cl$_2$ are shown. BF$_2$bdk ligand code shows groups disposed on core difluoroboron β-diketone ring: Me=methyl, Ph=phenyl, Np=naphthyl, An=anthracyl, Py=pyridyl, TFM=trifluoromethyl. 1: Me-PhOMe, 2: Ph-PhOMe, 3: Me-NpOMe, 4: Me-Py, 5: Np-NpOMe, 6: TFM-Np, 7: Ph-An, 8: Np-An.

The terms "luminescence", "luminescing", "luminescent", and related words as used herein refer to phosphorescence and/or fluorescence; i.e., the terms refer to the total release of photons other than by simple reflectance by a substance when placed under illumination, such as by a source of ultraviolet light, regardless of the physical mechanism by which such emission occurs. Typically, ultraviolet light of wavelength ($\lambda_{ex}$) is used to stimulate emission of photons from the luminescent composition, which has a characteristic emission spectrum ($\lambda_{em}$), quantum efficiency ($\Phi_F$) and excited state decay constant ($\tau_f$).

A "solid-state" composition, as the term is used herein, refers to a material that is a solid at the temperature examined (usually room temperature, about 20° C.), that is not dissolved in a liquid solvent but is in the physical state of a solid, which can be amorphous, crystalline, in a film, in bulk, and so forth. The solid compositions of the invention can be used individually or in combination as films, coatings, or blends in combination with other solid matrices or substrates (e.g. paper, plastic, polymer, glass, quartz, etc).

The boron-containing compositions themselves, termed difluoroboron 1-diketonate (2,2-difluoro-1,3,2-dioxaborazine) derivatives, as discussed below, are also referred to as "dyes", "compounds of the invention", and the like herein.

"Mechanochromic", "mechanochromism", "mechanoresponsive," and related terms as used herein refer to the phenomenon of a substance changing color upon mechanical disturbance, perturbation, pressure, shearing/smearing, or the like. In the present invention, the terms "mechanochromic", etc., refers to changes in the luminescent emission spectrum of light from a solid-state composition after mechanical disturbance, rather than to the color of the composition as viewed in visible light; thus the phenomenon referred to is specifically "mechanochromic luminescence" throughout. A mechanochromic luminescent effect can be observed after disturbance or pressure of a solid-state composition of the invention as applied by a solid physical object (swab tip, pencil eraser, artist's brush), a stream of gas (a breath), a stream of a liquid such as water, the impression of a solid stamp, pressure applied by a piston or other device for transmitting pressure, cellular adhesion, migration, mechanically active tissues and organs, or the like. The mechanochromic luminescent effect is observed in the luminescence of the perturbed solid under illumination by UV light.

A "heavy atom" as the term is used herein refers to an atom of an element with an atomic mass greater than that of argon.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N–1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3- pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), dihydro-benzo[b]thiophenyl), 6-(2,3-dihydro-benzo[b]thiophenyl), dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x\text{-}C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkyl, more preferred is —$(C_1\text{-}C_3)$perfluoroalkyl, most preferred is —$CF_3$.

The term "$(C_x\text{—}C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkylene, more preferred is —$(C_1\text{-}C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

The term "azido" refers to an N$_3$ group. An "azide" can be an organic azide or can be a salt of the azide (N$_3$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^+$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. Other salt-forming ions include triflate, tosylate, PF$_6^+$, BF$_4^+$, and BPh$_4^-$.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or a mixture of compounds according to formula (I), which contains the named compound or mixture of compounds according to formula (I) in an amount of at least 10 percent by weight of the total weight.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

DETAILED DESCRIPTION

The invention is directed in various embodiments to solid-state mechanochromic luminescent forms of difluoroboron β-diketonates (2,2,-difluoro-1,3,2-dioxaborazines), wherein the mechanochromic effect can be reversible; to methods of preparing the solid state compositions; to methods of using the solid state compositions such as in sensors and displays; to methods of generating mechanically responsive surfaces incorporating the compositions, including rewritable ones; to biological probes comprising, for example nanoparticulate or other aggregate forms of the compositions, to biomechanical sensors for mechanically active cells, tissues or organisms that interact with composition-containing mechanoresponsive surfaces and matrices, and to art, design, forensic, intelligence, and consumer products incorporating the compositions. Solid-state compositions of the invention and prepared by methods of the invention can have shifted emission wavelengths, narrow emission bandwidths, and luminescence emission wavelengths variable by mechanical effects such as pressure. In various embodiments, the mechanochromic luminescence is reversible, such as by heating, or by allowing to stand at room temperature for a period of time.

In various embodiments, the invention provides a composition comprising a mechanochromic luminescent solid-state form of a difluoroboron β-diketonate of formula (I)

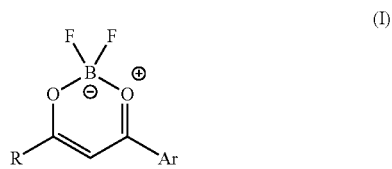

(I)

wherein

R is alkyl, alkenyl, alkynyl, cycloalkyl, or cycloalkylalkyl, wherein any alkyl, alkenyl, alkynyl, cycloalkyl, or cycloalkylalkyl is optionally substituted with 1-5 independently selected J groups; or R is Ar; wherein each Ar is an independently selected aryl, arylalkenyl, arylalkynyl, heteroaryl, heteroarylalkenyl, or heteroarylalkynyl group, wherein any aryl or heteroaryl can be monocyclic or polycyclic, and is optionally substituted with 1-5 independently selected J groups;

J is F, Cl, Br, I, OR', OC(O)N(R')$_2$, CN, NO, NO$_2$, ONO$_2$, N$_3$, CF$_3$, OCF$_3$, R', N(R')$_2$, SR', SOW, SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R'; wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J;

or any salt thereof.

The difluoroboron β-diketonates of formula (I) are also termed difluoroboronate complexes of propane-1,3-dione derivatives, propane-1,3-dionedifluoroboronates, and 2,2-difluoro-1,3,2-dioxaborazines. The terms "difluoroboron β-diketonate(s)" as used throughout to refer to compounds of this structural class. In various embodiments, the two substituent groups can be an optionally substituted alkyl and an optionally substituted aryl or heteroaryl group, or can both be identical or different optionally substituted aryl or heteroaryl groups.

The structure can be described by two resonance, or canonical forms, of the following structures:

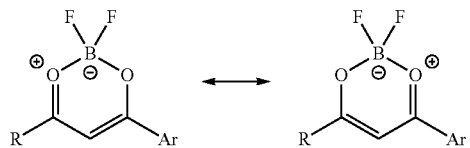

It is understood that the resonance forms are not isomers but are both resonance contributors to the actual electronic structure of the molecule, as in the case of benzene resonance structures. When R and Ar are identical, the two resonance contributors are degenerate.

For convenience, the charges can be omitted in structural representations, but they are understood to be present in a formal sense.

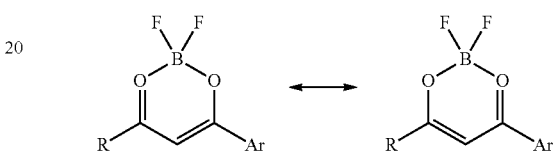

The complete nature of the electronic structure of these rings is open to interpretation, but it appears to have a distinctly aromatic nature judging from the stability of the compounds, e.g., to hydrolysis. All of the above formulas refer to the same class of compounds, difluoroboron β-diketonates as disclosed and claimed herein.

In various embodiments, the invention provides particular solid-state forms of difluoroboron β-diketonates possessing altered optical properties, such as luminescence emission wavelengths and bandwidths, compared to the properties of the respective compounds observed in solution. Furthermore, the solid-state luminescence is mechanochromic. The mechanochromic solid-state forms have the property that the luminescence emission spectra are altered by mechanical pressure or disturbance of the solid-state composition, such as by scratching, rubbing, smearing, or touching a film of the material. By luminescence is meant both phosphorescence or fluorescence, or both, that is, the emission of light upon stimulation by illumination, for example by ultraviolet illumination. A sample of a mechanochromic luminescent material can luminesce (i.e., fluoresce and/or phosphoresce) with a particular color (emission spectrum) when undisturbed, but luminesce with another color (emission spectrum) after disturbance, such as by application of pressure. The disturbance can be the application of pressure to a substrate bearing a film layer of the solid-state luminescent material of the invention, wherein the amount of pressure required to produce a visible or detectable change in the emission spectrum can vary from compound to compound and from one type of solid state composition to another or depending on thickness of a layer of the mechanoresponsive luminescent dye. For example, different crystalline forms, or amorphous or microcrystalline forms, of the same chemical compound can possess different emission spectra in both the undisturbed and in the disturbed condition. In various embodiments, the emission luminescence of a mechanically perturbed portion of the composition of the invention can be red-shifted or can be blue-shifted relative the emission luminescence of an unperturbed portion of the respective composition, depending on the particular structure of the difluoroboron β-diketonate used. Red-shifting with mechanical disturbance is most common.

In various embodiments, the mechanochromic effect can be reversible under various conditions. For example, the mechanochromic effect can be reversed spontaneously in the time frame of seconds to minutes at room temperature (i.e., about 20° C.), or upon heating to elevated temperatures, or in the presence of a vapor or gas.

In various embodiments, the invention provides different varieties or states of the solid-state forms, each of which can have characteristic mechanochromic luminescence properties. For example, the solid-state form can be a film, deposited on a substrate such as glass, quartz, paper, synthetic papers or sheets such as Yupo®, cloth, plastic sheets (e.g. PLA, Vyco®), inorganic substrates such as ceramics, and the like. The film can be deposited by applying a solution of the difluorodioxaborazine on the substrate surface, then removing the solvent. For example, a film can be spin-cast onto a surface. Alternatively, the solid can be deposited directly onto a surface such as by spraying an aerosol, dust deposition, spreading a melted form, smearing the solid or the like. Alternatively, the dye may be thoroughly mixed with a solid matrix or support material which can then be fabricated in different ways (e.g. as bulk materials, particles, fibers, coatings, etc) to generate mechanoresponsive dye impregnated materials. This could be by mixing the dye and matrix materials as solids, or dissolving the dye and matrix material in solution and then removing the solvent with microphase separation to generate responsive dye aggregates, or by some combination of solid and solution mixing.

In other embodiments, the solid-state form can be a crystalline form, or one of, or a mixture of multiple crystalline forms in which a particular compound can be obtained. In various embodiments, each of a plurality of crystalline forms of the compound of formula (I) each can have a luminescence emission spectrum that is distinct from at least one of a different crystalline form. For example, for the compound $BF_2AVB$, discussed below, at least three distinct crystalline forms, and an amorphous form, each with distinct mechanochromic luminescent properties, have been characterized. In various embodiments, the solid-state form can be a nanoparticulate solid-state form, i.e., having individual solid particles of less than about 1 micron in diameter make up the bulk composition. Particle size can also influence mechanochromic luminescent properties of the solid-state forms of the invention. Additionally, thermal annealing (i.e. heating) of the coatings and films and solids that are applied to surfaces or combined with matrices in different ways, can produce more crystalline materials, and thus, a greater emission color shift upon smearing to generate an amorphous state.

The physical disturbance that can result in a detectable amount of mechanochromic luminescence can vary from compound to compound and among solid-state forms of the compounds. In various embodiments, a mechanochromic luminescent effect can be visible to the human eye after only the pressure of a touch is applied to a solid-state form such as a film or a powder. In other embodiments, a higher degree of pressure can be needed. The amount of mechanochromic luminescence observed can be a function of the amount and the duration of the applied pressure. In many embodiments, the pressure that can be applied with a cotton swab tip or a pencil eraser is sufficient to result in an unmistakable change in luminescence color under UV light illumination. For example, in various embodiments, the mechanochromic effect on the luminescence can induced by a pressure of at least about 1 $gm/cm^2$ on the solid-state form, or about 10 $gm/cm^2$ or about 100 $gm/cm^2$ on the solid-state form of the invention. A pressure of 1 kilopascal (kPa) is about 10.2 $gm/cm^2$, so 1 $gm/cm^2 \sim 0.1$ kPa.

In various embodiments, the solid-state forms of the invention can be used in conjunction with fluorescence microscopy to measure pressures and tractions at the cellular level. Such forces have been measured to be in the range of 0.1-5.0 kilopascals (about 1-50 $gm/cm^2$). See, for example, W. Legant, et al., "Measurement of mechanical tractions exerted by cells in three-dimensional matrices," *Nature Methods*, published online 14 Nov. 2010; DOI:10.1038/NMETH.1531. Mechanoresponsive materials containing the luminescent dye as coatings or impregnated in a matrix can serve as biomechanical sensors (e.g. tension, traction, or movement sensors) for mechanically active cells, tissues and organisms (e.g. as cells or cell assemblies migrate and grow on or within the mechanoresponsive surfaces or tissue matrices). Mechanoresponsive dyes that are also oxygen sensitive (i.e. heavy atom containing systems with enhanced triplet emission) could provide information about mechanical forces and oxygen levels (e.g. in a tissue engineering matrix), as mechanical force is necessary to activate the oxygen sensitivity, causing the luminescence to be quenched in mechanically perturbed regions. Alternatively, disposing, for example, nanoparticles of solid-state forms of the invention or dye aggregates of different sorts, within a living tissue or cell, then monitoring the emission luminescence of the nanoparticles, can provide semi-quantitative data concerning the pressure or tension within the living tissue or cell. The mechanosensitivity of the composition can be tuned synthetically and through processing, to match the force range and type of interest.

In various embodiments, the mechanochromic effect on the luminescence is reversible, as discussed in greater detail below. By "reversible" is meant that the effect of the mechanical perturbation or pressure disappears over time, restoring the original luminescence of the solid-state form. This reversibility can be observed in various embodiments at room temperature, and can occur over the period of seconds to hours. In other embodiments, an elevated temperature can be needed to cause the reversion of the mechanochromic effect on the luminescence to the original unperturbed luminescence properties. In various embodiments, reversibility can be achieved through exposure of the perturbed solid-state form of the invention to a vapor, such as nitrogen, or a solvent vapor, or the like.

In various embodiments, the physical parameters of the luminescence of a solid-state form of the invention are distinct from the parameters of luminescence of the same chemical compound but dissolved in a solvent. For example, in various embodiments, a luminescence light emission band of a solid-state form of formula (I) of the invention can be more narrow than a luminescence light emission band from the respective difluoroboron β-diketonate of formula (I) in solution, or wherein the luminescence light emission band of the composition of claim 1 is bathochromically shifted with respect to a luminescence light emission band from the respective difluoroboron β-diketonate of formula (I) in solution, or both. This effect is believed to arise from special ordered, aggregate states of the solid-state forms of the difluoroboron β-diketonate of formula (I).

The solid-state form of the invention can comprise any of a broad range of chemical structures, with the understanding that each solid-state form of each compound will have its own characteristic properties of luminescence, mechanochromic luminescent behavior, and reversibility of the mechanochromic luminescence effect.

In various embodiments, for the compound of formula (I), R can be alkyl, or, in other embodiments, R can be alkyl substituted with halogen, more specifically, R can be fluoroalkyl. For example, R can be a linear or branched alkyl chain, which can include double or triple bonds or cycloalkyl groups therein, or can be a cycloalkyl or cycloalkylalkyl group, any of which can be mono- or independently multi-substituted with a J group as defined herein.

In various other embodiments, for the compound of formula (I), R can be aryl or heteroaryl, optionally substituted with 1-5 J. For example, R can be phenyl, naphthyl, anthracinyl, or can be pyridyl, quinolyl, or the like.

In various embodiments, the Ar group can be an independently selected aryl or heteroaryl group, wherein any aryl or heteroaryl can be monocyclic or polycyclic, and is optionally substituted with 1-5 J groups. The central difluoroboron β-diketonate (difluorodioxaborazinyl) ring is substituted with at least one Ar group, which is aromatic, but the other substituent can be aromatic or aliphatic in nature. Substitution with various J groups can occur on either aromatic or aliphatic groups provided the substitution provides a structure of at least moderate chemical stability such that the compound can be deposited to provide a solid-state form without overwhelming decomposition.

J groups can include F, Cl, Br, I, OR', OC(O)N(R')$_2$, CN, NO, NO$_2$, ONO$_2$, N$_3$, CF$_3$, OCF$_3$, R', N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

More specifically, the difluoroboron β-diketonate of formula (I) can be of formula

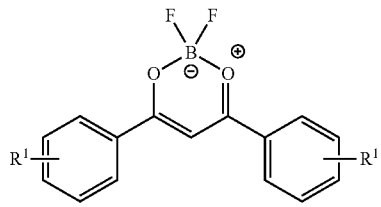

wherein each independently selected R' is C1-C24 alkyl or C1-C24 alkoxy, wherein any alkyl or alkoxy can be unsubstituted or can be mono- or independently multi-substituted with J. Or, the difluoroboron β-diketonate of formula (I) can of the more regiochemically defined formula

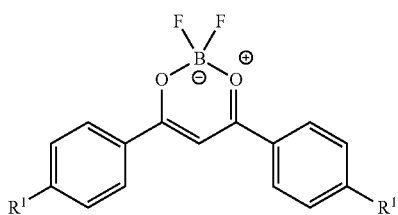

wherein each independently selected R$^1$ is C1-C24 alkyl or C1-C24 alkoxy, wherein any alkyl or alkoxy can be unsubstituted or can be mono- or independently multi-substituted with J.

In both of the above embodiments, both substituent groups on the central difluoroboron β-diketonate (difluorodioxaborazinyl) ring are substituted phenyl groups. In other embodiments, the difluoroboron β-diketonate of formula (I) can comprise a fused bicyclic or tricyclic aromatic ring, optionally substituted with 1-5 independently selected J.

More specifically, the compound can be of formula BF$_2$AVB

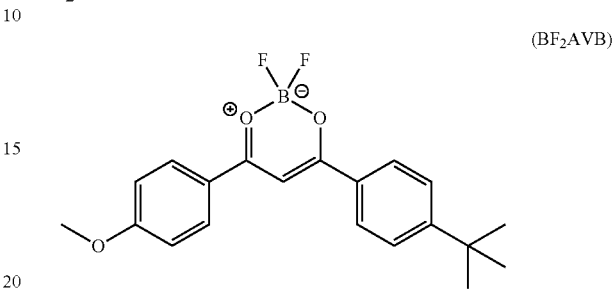

(BF$_2$AVB)

or can be a homolog of BF$_2$AVB wherein the methoxy group is replaced by longer alkoxy chains, either straight chain or branched, or can bear an alkyl group other than t-butyl.

In various embodiments, difluoroboron β-diketonates of formula (I) can be conjugated through appropriate functional groups (OH, NH$_2$, etc.) to biomolecules such as fatty acids, lipids, and peptides/proteins.

The UV light absorption spectrum, and the luminescence emission spectrum, can be tuned by varying the identity of the R and the Ar groups, and the substituents on the R and the Ar groups. For example each Ar group can be an independently selected phenyl, naphthyl, or pyridyl group, which can bear one or more alkoxy, halo, haloalkyl, or amino substituents, or the like. If the R group is other than Ar, it can likewise bear one or more alkoxy, halo, haloalkyl, or amino substituents, or the like, and can further include double bond and triple bond unsaturations, which can be isolated or conjugated with the ring and/or with other unsaturations. It is within ordinary skill to synthesize and evaluate the UV light absorption spectrum, and the luminescence emission spectrum, of any compound for which a composition of the invention is prepared. See, for example, FIG. 1, below, showing the emission color tunability for compounds 1-8:

1: Me-PhOMe, 2: Ph-PhOMe, 3: Me-NpOMe, 4: Me-Py, 5: Np-NpOMe, 6: TFM-Np, 7: Ph-An, 8: Np-An; wherein the two groups are disposed on a 2,2-difluoro-1,3,2-dioxaborazine ring according to the following abbreviations: Me=methyl, Ph=phenyl, Np=naphthyl, An=anthracyl, Py=pyrenyl, TFM=trifluoromethyl. Accordingly, the composition of the invention can be any of the mechanochromic luminescent solid-state forms of any of the following structures:

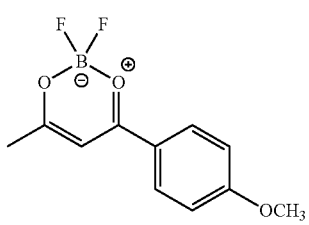

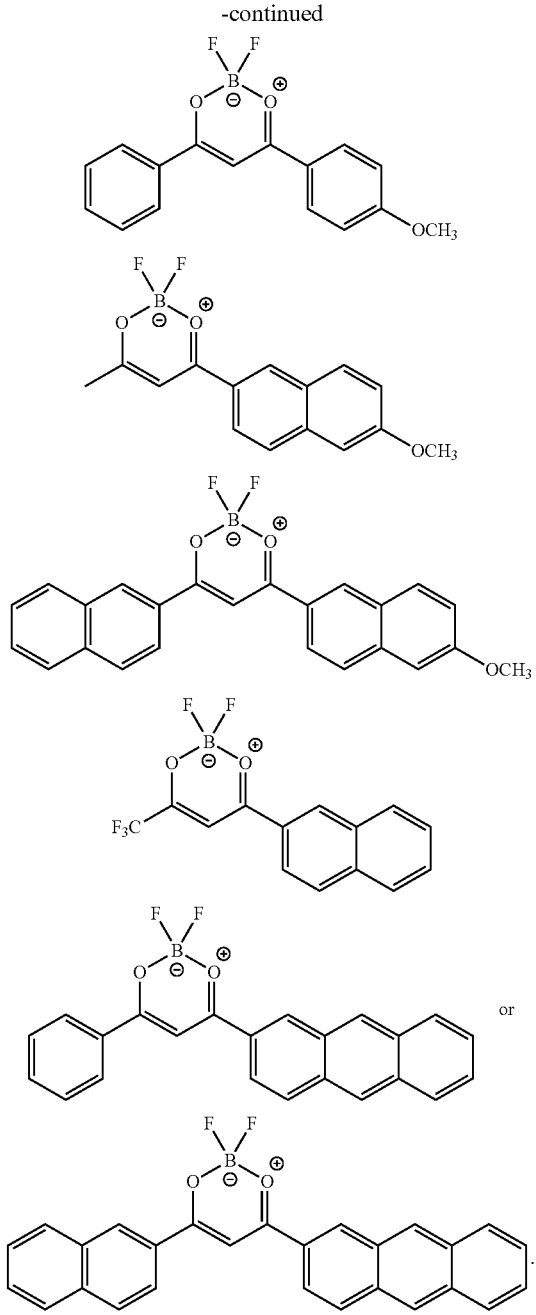
Some exemplary compounds of formula (I) for solid-state compositions of the invention include diaryl, aryl alkyl, and aryl haloalkyl difluorodioxaborazines, examples of which are shown below.
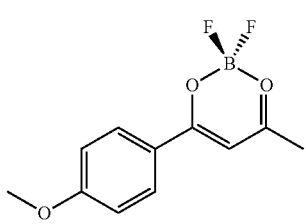
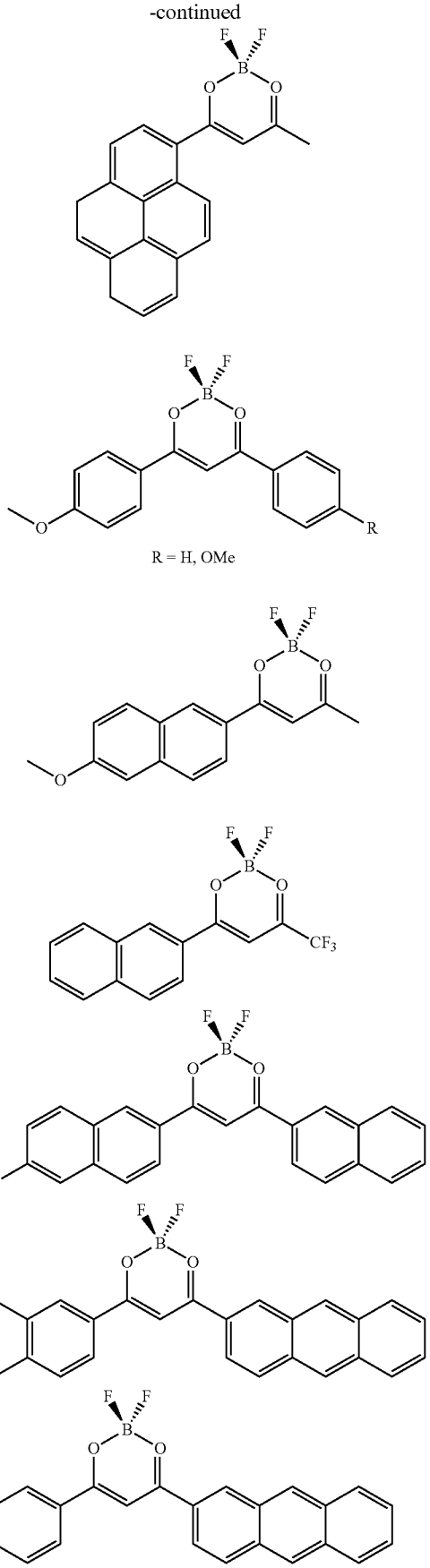
R = H, OMe

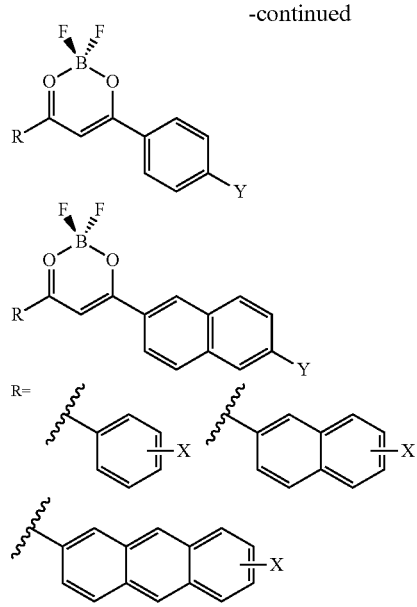

X, Y = H, halide, OR, NR$_2$, OCH$_2$CH$_2$OH, other substituents
Note: There can be multiple substituents per arene ring In various embodiments, the invention provides a mechanochromic luminescent solid-state form of compound of formula (I) wherein at least one Ar is phenyl, napthyl, or anthracyl, any of which can be mono- or independently multi-substituted with halo, amino, mono- or di-alkylamino, mono- or bis-hydroxyalkylamino, hydroxy, alkoxy, or hydroxyalkoxy.

In various embodiments, the Ar group can comprise an alkenylaryl or alkynylaryl, which can be mono- or independently multi-substituted with J groups as described above. For example, compounds of formula (I) can include compounds of the formulas

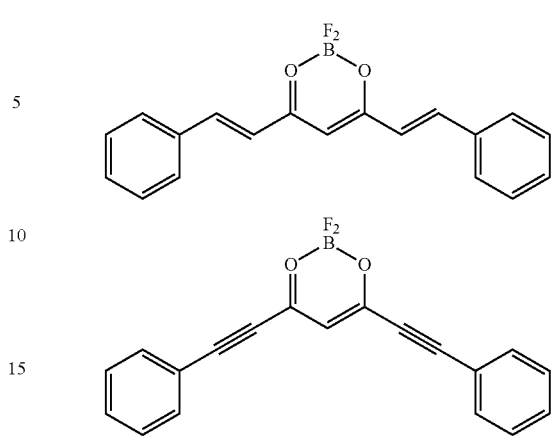

and related structures, including compounds comprising heteroaryl rings, J-substituted aryl and heteroaryl rings, and the like. A specific example is

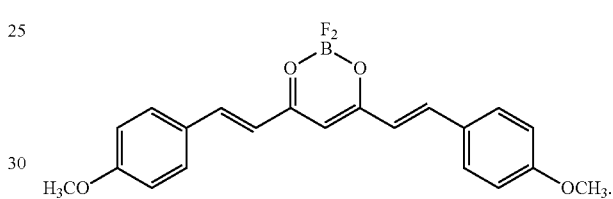

Solid state mechanochromic luminescent forms of these compounds are compositions of the invention.

In various embodiments, the invention provides a mechanochromic luminescent solid-state form of compound of formula (I) wherein the compound is any of the following:

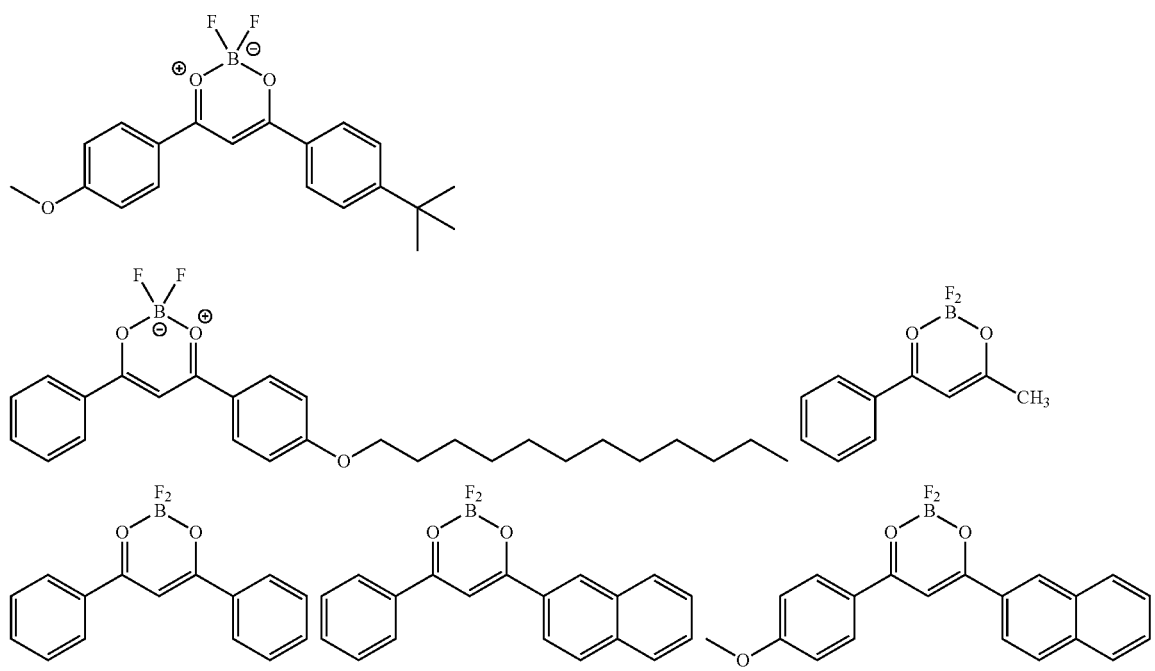

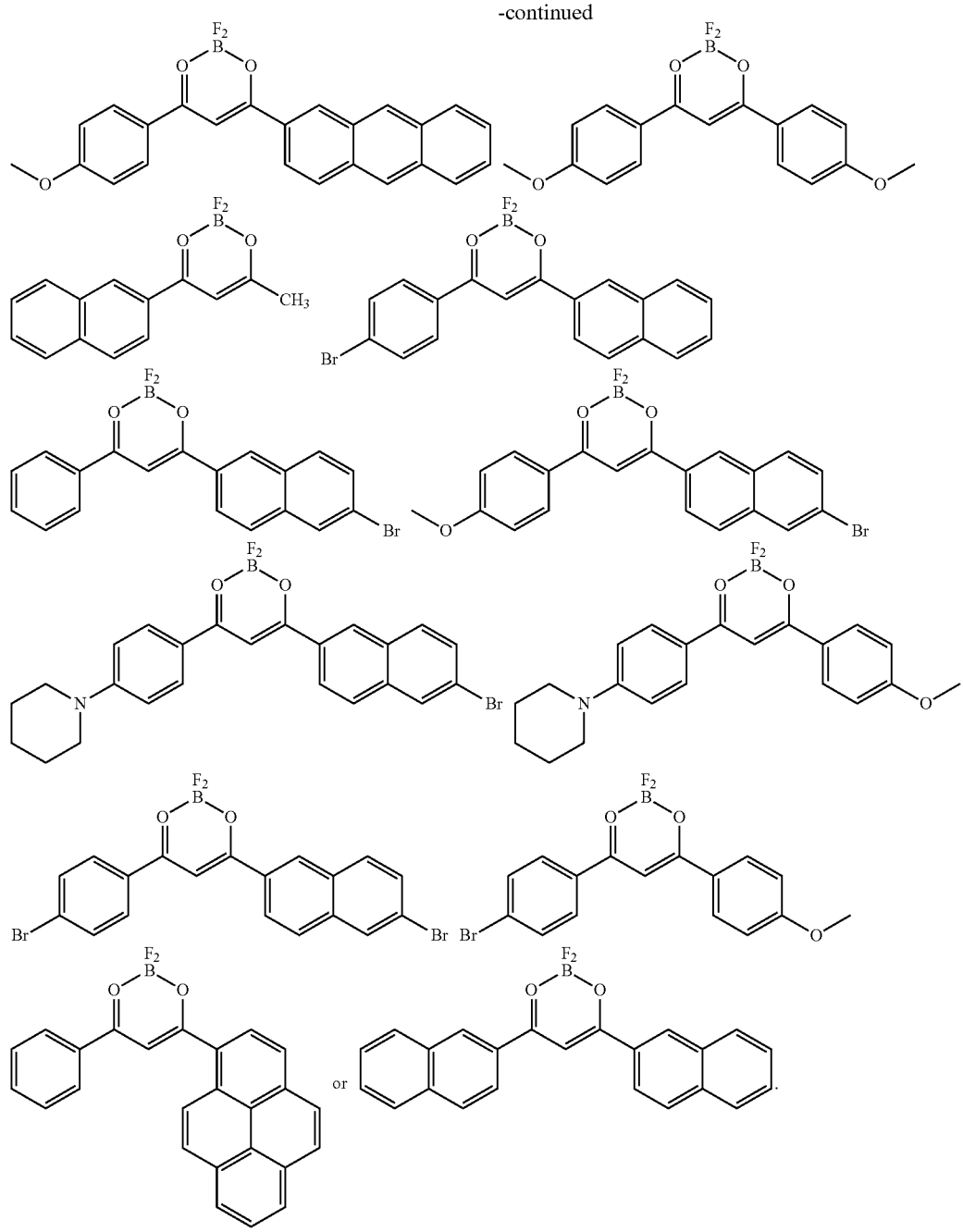

The spectral characteristic of solid-state forms can be further altered in the substances including basic nitrogen atoms (amines) in the structures, such as the piperidine derivatives shown above. Protonation of the amines, or formation of complexes between the amino groups and Lewis acids, or metal ions, can serve to alter the emission characteristics of the solid-state forms.

In various embodiments, a solid-state form of the invention can be combined with a second light absorbing or luminescing material to provide a solid-state composition comprising the two materials. A solid state composition comprising a compound of the invention plus a second luminescent material can be termed a "light-bridge" or energy transfer composition, because the presence of the second material can alter the mechanochromic luminescent properties of the composition with respect to a comparable composition lacking the second material. The second light absorbing or luminescent material can be another difluoroboron β-diketonate of the invention, or it can be of an entirely different structural class. It is not necessary that the second light-absorbing or luminescent compound itself luminesce, or luminesce in the solid state, but it should have a significant ability to absorb and transfer light energy. In various embodiments, more than one additional light absorbing or luminescing material can be components of the solid-state composition including a difluoroboronate β-diketonate compound. One or more of the additional compounds can be other difluoroboronate β-diketonates, or can be other dyes or luminescent materials, for example, various kinds of Rhodamine dyes.

In various embodiments, the second luminescent material does not in pure form exhibit significant solid-state luminescence (i.e., only exhibits luminescence when in solution), but in the inventive composition the second material can alter the luminescent properties of the composition. More specifically, the second luminescent material can comprise Rhodamine B or a salt thereof.

During the course of solid-state property studies, it was discovered that even trace amounts of Rhodamine B (RhB) alter the emission color of $BF_2AVB$ solid films and that scratching the RhB doped film intensifies the resultant orange RhB emission. This suggests strong interactions (physical and/or chemical) between the two species, given that normally RhB does not emit in the solid state. Energy transfer (ET) from the boron dye to RhB may occur, with scratching serving as a mechanically induced "light bridge", increasing ET efficiency. That other UV absorbing solid-state matrices such as acetophenone and 8-hydroxyl quinoline do not promote RhB emission, suggests something unique about the difluoroboronate β-diketonate class of compounds. Other of the numerous Rhodamine dyes, for instance those available from Sigma-Aldrich, can be used in place of Rhodamine B. $BF_2AVB$ and RhB are emissive species with spectral overlap required for Förster ET. Because (β-diketones are structurally similar to $BF_2$bdks,bdk/RhB compositions comprising β-diketones without the difluoroboronate complexation, can exhibit "light bridge" properties as well. It is possible that under these solid-state conditions, the ET rate between boron dyes and Rh is faster than fluorescence (or non-radiative decay of bdks) and a different mechanism is operative. Boronate (formula (I)) or diketone (formula (II)) dye films can be spin cast onto glass and characterized before and after soaking in aqueous rhodamine solutions of different concentrations to test for sensitivity (i.e. absorption, excitation, emission, lifetime, and morphology via AFM and XRD.) For various practical uses it is best to attach the boron dye or bdk to glass and other surfaces so that they aren't readily washed or rubbed off. Fortuitously, a difunctional, vinyl ether-substituted dbm ligand, $dbm(OVE)_2$, readily forms crosslinked ligand or boron dye coatings when treated with radical initiators or $BF_3$ respectively.

These stabilized films produce the same effects when subjected to RhB treatment. Thus, the diketone, boron dye, and RhB and applied force may be combined in different ways, sequences, and media. In one arrangement, the light absorbing compound (e.g. $BF_2$bdk or bdk) and RhB may be combined in advance (as solid or evaporated solution mixtures, e.g. spin cast films) and then the emission may be enhanced or further activated with an applied force. Alternatively, the diketone coating may be treated with a "$BF_2$" source (e.g. $BF_3$ or reactive $BF_4$— salt), then a scratch applied, followed by exposure to RhB solid or solutions to "light up" the mechanically perturbed regions. Alternatively, the RhB may be delivered to the $BF_2$bdk or bdk material or coated surface with force (e.g. with a liquid or solid applicator or dispenser). This configuration could be useful in biotechnological contexts, such as RhB detection assays (e.g. where the RhB originated from a labeled biomolecule, cell or tissue extract), including high throughput formats. Even mechanically active RhB labeled cells, cell aggregates, tissues, or organisms can serve as the RhB delivery device to press or otherwise mechanically combine the RhB with the $BF_2$bdk or bdk composition to activate the "light bridge" effect. In this way, these material mixtures can visualize or generate maps of RhB labeled cell migration, tissue forces, and organism movement and behavior, as mechanically active RhB labeled biological systems come in contact with the $BF_2$bdk or bdk containing material. Compositions, substrates/matrices, and dye processing can be utilized to generate mechanosensors in the force range of interest.

Accordingly, in various embodiments, the invention provides a composition comprising a diketone of formula (II)

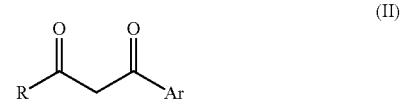

wherein

R is alkyl, alkenyl, alkynyl, cycloalkyl, or cycloalkylalkyl, wherein any alkyl, alkenyl, alkynyl, cycloalkyl, or cycloalkylalkyl is optionally substituted with 1-5 independently selected J groups; or R is Ar; wherein each Ar is an independently selected aryl or heteroaryl group, wherein any aryl or heteroaryl can be monocyclic or polycyclic, and is optionally substituted with 1-5 independently selected J groups;

J is F, Cl, Br, I, OR', OC(O)N(R')$_2$, CN, NO, NO$_2$, ONO$_2$, N$_3$, CF$_3$, OCF$_3$, R', N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J; or a salt thereof;

and a second luminescent material.

In various embodiments, the second luminescent material does not in pure form exhibit significant solid-state luminescence (i.e., only exhibits luminescence when in solution), but in the inventive composition the second material can alter the luminescent properties of the composition. More specifically, the second luminescent material can comprise Rhodamine B.

Synthesis of difluoroboron β-diketonates

Compounds can be prepared according to methods described herein and in documents incorporated by reference here, see the Examples section. One synthetic approach is to contact a propane-1,3-dione with $BF_3$ etherate in solution, which readily yields the difluoroboron β-diketonate compound. Propane-1,3-diones, bearing one or more aromatic substituents, which are well known in the art, can be prepared by appropriate methods including Claisen condensation.

The Claisen condensation as it takes places between an ester and a carbonyl compound containing an active (enolizable) hydrogen atom is well known to produce propane-1,3-diones as needed for formation of the difluorodioxaborazine compounds of the invention. A reaction scheme for an exemplary Claisen condensation is shown below:

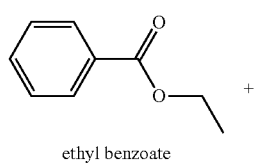

ethyl benzoate

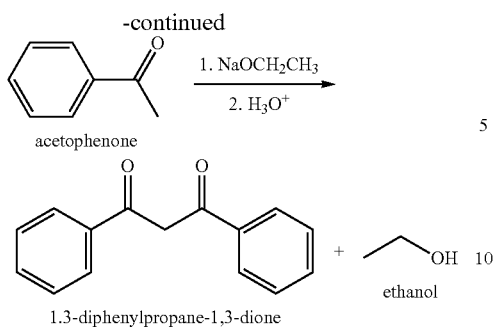

acetophenone

1. NaOCH₂CH₃
2. H₃O⁺

+ ethanol (CH₃CH₂OH)

1,3-diphenylpropane-1,3-dione

It is within ordinary skill to select suitable precursors to provide propane-1,3-diones of the appropriate structure. For example, polycyclic aromatic compounds, heteroaryl compounds, substituted aryl and heteroaryl compounds, alkyl-aryl or haloalkyl-aryl propane-1,3-diones can all be prepared by this method. Reactive functional groups, i.e., substituent groups designated as J groups in the definition of the compound of formula (I) herein can be introduced bearing suitable protecting groups, such as oxygen- or hydroxyl-protecting groups, and nitrogen- or amino-protecting groups, as are well-known in the art. A wide range of precursor esters and ketones are commercially available, and others can be prepared by literature procedures used by those of ordinary skill in the art of organic synthesis.

The propane-1,3-diones thus obtained are readily converted to the difluoroboron β-diketonates of the invention, such as by contacting the diketone with boron trifluoride etherate in solution, such as in THF solution at room temperature. Groups such as substituent amino groups that might react with boron trifluoride etherate can be carried through this conversion in protected form using suitable protecting groups such as are well-known in the art, which can be removed from the stable difluorodioxaborazine compounds to provide target compounds of the invention.

Inventive solid-state forms of the compounds can be prepared by various methods as described herein and known to the person of ordinary skill, such as by dissolving the compound in a solvent, then removing the solvent, such as by evaporation under vacuum, spin-casting, spray drying, precipitation with a non-solvent, and the like.

A range of synthetic procedures enabling the person of ordinary skill to prepare various structural classes are provided below in the Examples.

Exemplary Embodiments

It has been discovered that various solid-state forms of difluoroboron avobenzone (avobenzene difluoroboronate, BF₂AVB), such as crystalline forms of various

BF₂AVB

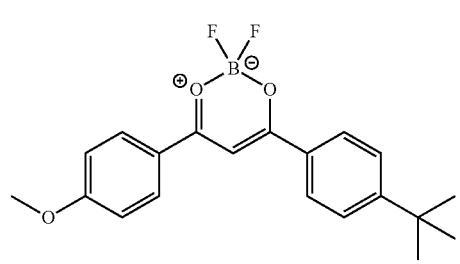

morphologies, and amorphous films, possesses unexpected narrowband, morphology-dependent luminescence. Crystalline and amorphous solid forms can also exhibits unusual reversible mechanochromic luminescence that recovers spontaneously over time at room temperature, or more quickly with heating. Thus, a film of an inventive solid form of a difluorodioxaborazine compound, luminescing at a particular wavelength under UV illumination, can be marked by application of pressure such as by a pencil eraser or a finger tip, such that the area so marked exhibits luminescence of a different emission wavelength or color.

Figure 2:
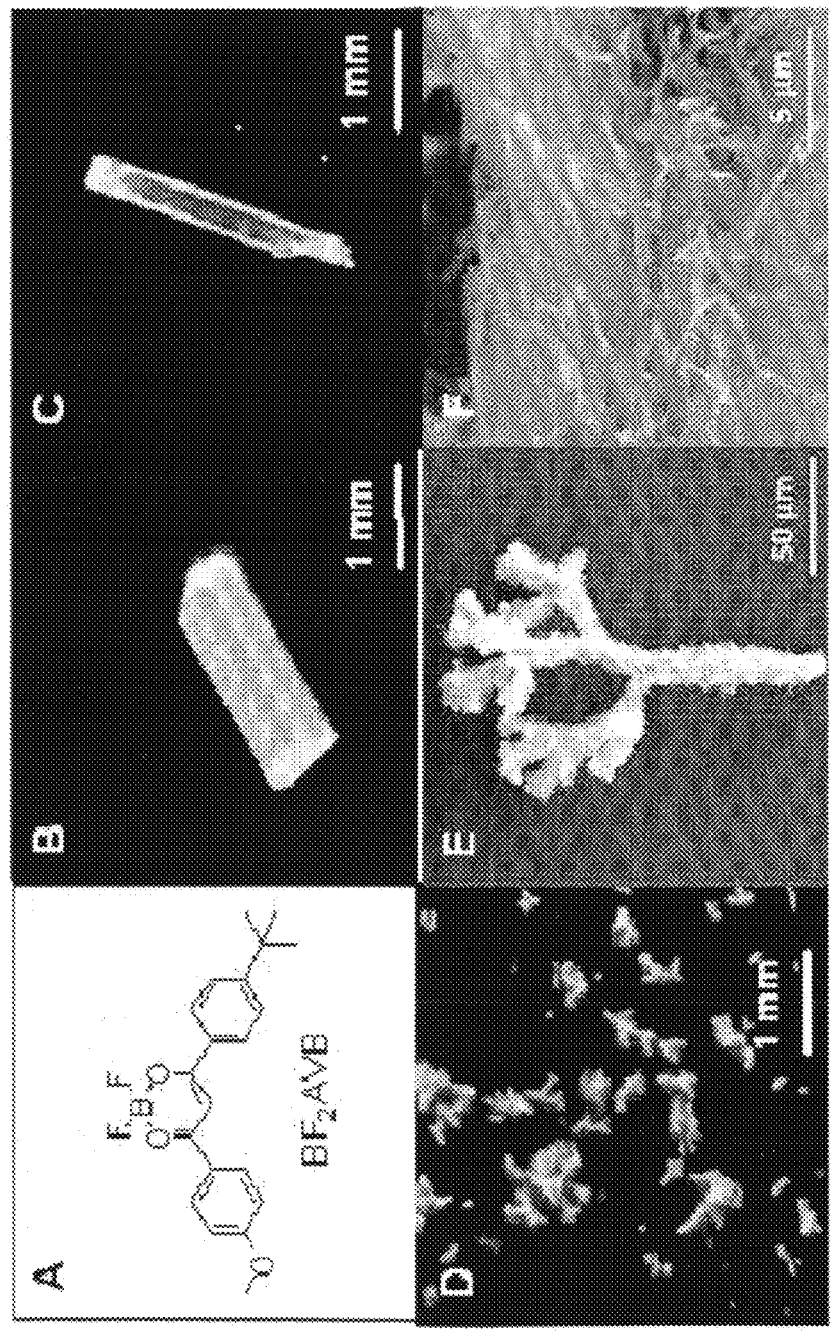
FIG. 2 shows (A) the chemical structure of BF$_2$AVB, and photographs showing (B) green-luminescing, and (C) cyan-luminescing crystals and (D) blue-luminescing coral-like solid under UV excitation (X=365 nm), as well as (E) SEM images of the dendritic coral-like structure, and (F) a magnified view of the porous surface of the dendritic structure.

During slow solvent evaporation, BF₂AVB forms two different types of crystals: large green-emitting prism-like crystals and cyan-emitting needle-like crystals. Images of BF₂AVB crystals under UV excitation are shown in FIG. 2. While exploring different processing conditions, we discovered another very interesting solid-state form (FIG. 2D) via CH₂Cl₂ evaporation from a cotton swab. The morphology of the material thus fabricated was examined by scanning electron microscopy (SEM) to reveal dendritic BF₂AVB solids typically several hundred microns in size with highly porous surfaces comprised of feathery thin sheets (FIGS. 2E and 2F).

As shown in Scheme 1, BF₂AVB can be prepared using the general procedure outline above of a Claisen condensation followed by contacting the propane-1,3-dione with boron trifluoride etherate in solution.

Scheme 1: Synthesis of avobenzene difluorobornate

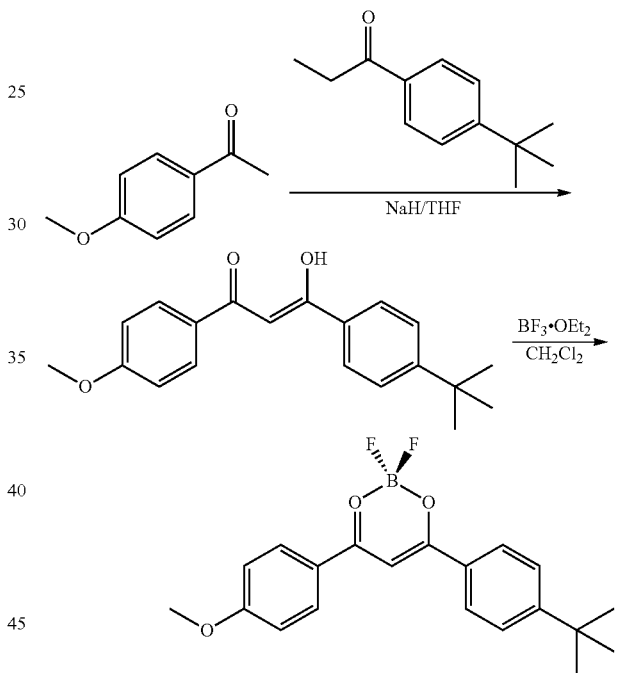

Various solid state forms of BF₂AVB were prepared according to procedures outlined below, include three crystalline forms and an amorphous film form, each of which displays distinct mechanochromic luminescent properties.

Figure 3:
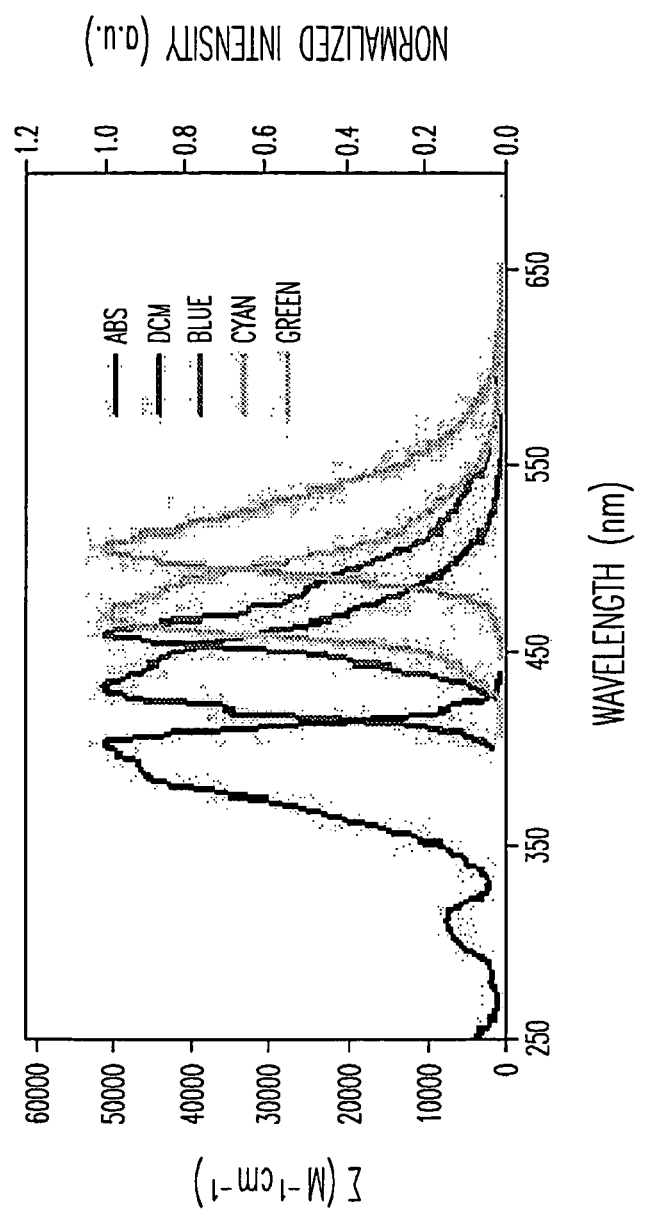
FIG. 3 shows an absorption spectrum in CH$_2$Cl$_2$ (DCM) and a fluorescence emission spectra ($\lambda_{ex}$=369 nm) for BF$_2$AVB in optically dilute CH$_2$Cl$_2$ solution, and the corresponding spectra of dendritic (blue-luminescing), needle (cyan-luminescing) and prism (green-luminescing) solid-state forms of BF$_2$AVB, having FWHM=47, 31, 42, and 41 nm, respectively.
Figure 4A:
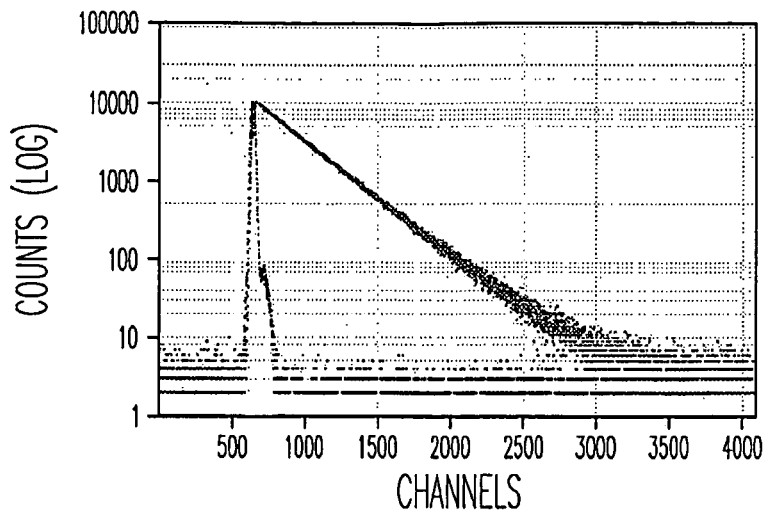
FIG. 4 shows: (A) a fluorescence lifetime decay profile for the green-luminescing BF$_2$AVB crystal (Time-to-amplitude converter (TAC) range: 200 ns; blue dots are prompt decay); (B) a fluorescence lifetime decay profile for the cyan-luminescing BF$_2$AVB crystal (TAC range: 100 ns; blue dots are prompt decay); (C) a fluorescence lifetime decay profile for the blue-luminescing BF$_2$AVB dendritic solid (TAC range: 100 ns, blue dots are prompt decay).
Figure 4B:
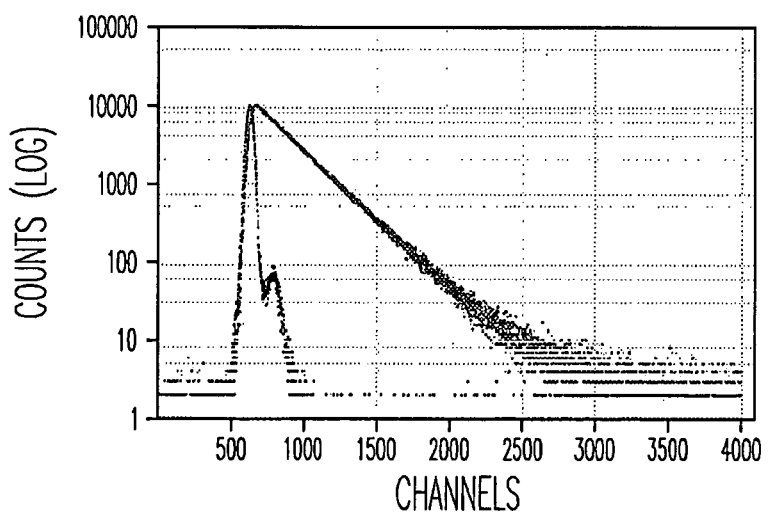
Figure 4C:
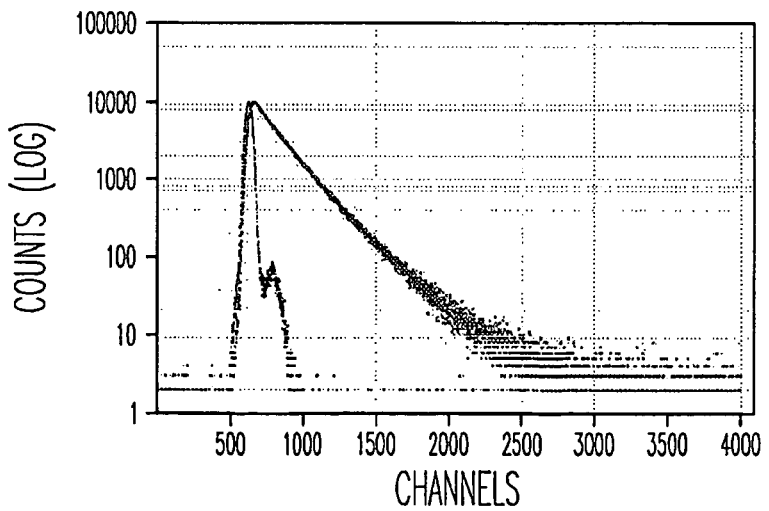

Under a UV lamp, the three forms of BF₂AVB solids exhibited green, cyan, and blue emissions, corresponding to the prism, needle and dendritic solids, respectively. Steady-state fluorescence spectra are shown in FIG. 3. Normally BF₂(β-diketonate)$_{(s)}$ emission is significantly redshifted and broadened relative to dye solutions (Ono, K.; Yoshikawa, K.; Tsuji, Y.; Yamaguchi, H.; Uozumi, R.; Tomura, M.; Taga, K.; Saito, K. *Tetrahedron* 2007, 63, 9354-8). For example, many difluoroboron dibenzoylmethane (dbm) derivatives show bathochromic shifts of ~100 nm with ~50 nm bandwidth broadening (Mirochnik, A. G.; Bukvetskii, B. V.; Fedorenko, E. V.; Karasev, V. E. *Russ. Chem. Bull.* 2004, 53, 291-6). In contrast, all three BF₂AVB solids show very narrow bandwidth emission compared fluorescence in CH₂Cl₂ ($\lambda_{em}$=433 nm; FWHM (full width at half maximum)=47 nm). Among them, the dendritic solid formed by rapid solvent evaporation shows the most narrow emission band (FWHM=31 nm) with peak intensity $\lambda_{max}$=459 nm. The cyan and green emitting crystals have emission maxima at 470 and 505 nm and FWHM values of 47 and 42 nm, respectively. The dendritic form of the solid-state composition has rich emission structures, perhaps due to vibrational or multi-component contributions. The fluorescence lifetimes $\tau_f$ of the green, cyan, and blue solids exhibit a decreasing trend of 16.7, 6.9, and 5.4 ns, indicating that the green crystal may be the most energetically stable form. Also, both of the single crystals have single-exponential decay (FIGS. 4(A), 4(B)). The dendritic solid can be fit to double exponential decay (FIG. 4(C)), where a more heterogeneous molecular environment may be present in comparison to the single crystals.

The morphology-sensitive solid-state emission of $BF_2AVB$ is also evident upon mechanical perturbation. When the blue-emitting $BF_2AVB$ dendritic solid (—3 mg) is smeared onto a piece of weighing paper (2×2 in$^2$), it exhibits yellow emission under UV excitation ($\lambda_{ex}$=365 nm). After a few minutes, the bright yellow fluorescence fades and a greenish emission emerges. This fading process is facilitated by brief heating (~30 s in ~110° C. oven or ~3-5 s with a heat gun), resulting in a green-blue emission color under UV excitation. After thermal annealing, even a small mechanical perturbation, such as a slight touch with the tip of a cotton swab, can change the green-blue $BF_2AVB$ film emission to yellow (FIG. 5). The yellow emission gradually reverts back to green again at room temperature, with much faster recovery at elevated temperature. After annealing, the written regions are no longer readable.

Mechanochromic emission changes for solid-state $BF_2AVB$ were also investigated by fluorescence spectroscopy. FIG. 5E shows the initial and post-smearing fluorescence spectra for the solid on a quartz substrate as a function of recovery time. Consistent with visual observation, after $BF_2AVB$ was smeared, the fluorescence spectrum was drastically broadened with the full width at half maximum (FWHM) increasing from 30 nm to 119 nm. The corresponding emission maximum shifted from 460 nm to 542 nm with a tiny shoulder at ~460 nm which closely matches the starting solid emission. The recovery dynamics are also evident from the spectra recorded at different times. After smearing, the blue shoulder grew (up to 1 h), the main peak gradually blue shifted, and the FWHM decreased with time. The emission color stabilized after ~1 day and could be switched back to yellow emission with smearing. Regardless of the initial state (single crystal or dendritic solid), smeared $BF_2AVB$ solids exhibit similar yellow emission and their recovery dynamics are also similar as long as the smeared solid film has approximately the same thickness. (Slower recovery has been observed for thicker films.) FIG. 5F verifies fluorescence "rewritability" of a $BF_2AVB$ solid film on a piece of weighing paper.

Figure 6:
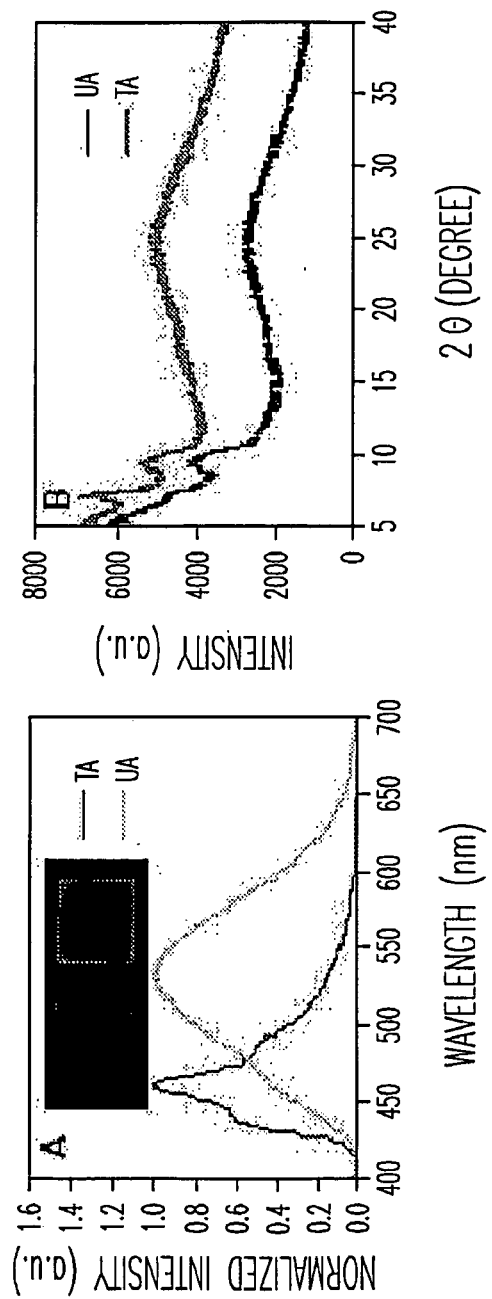
FIG. 6 shows (A) BF$_2$AVB spin-cast films luminescence emission ($\lambda_{ex}$=365 nm) and (B) X-ray diffraction spectra for unannealed (UA) and thermally annealed (TA) samples.
Figure 7:
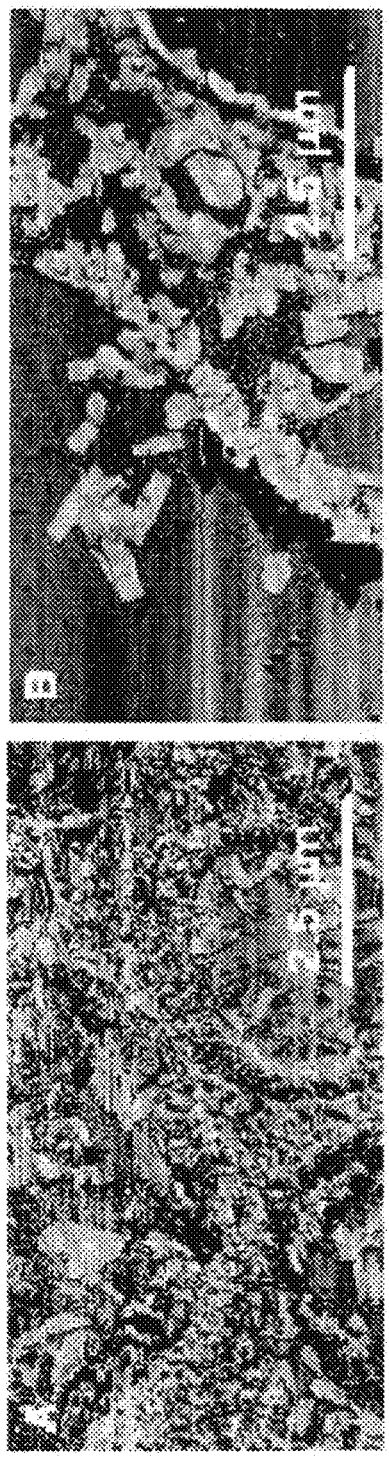
FIG. 7 shows AFM images of BF$_2$AVB spin-cast films on glass substrates (A) before and (B) after thermal annealing.

An amorphous $BF_2AVB$ film on a glass substrate was formed by spin coating from $CH_2Cl_2$ solution. The emission spectrum of the resulting film resembles that of the smeared $BF_2AVB$ solid, significantly redshifted and broadened ($\lambda_F$=530 nm). Thermal annealing at 110° C. for 5 min however, turned the film emission blue ($\lambda_F$=459 nm), similar to the dendritic solid emission except that the thin film shows a high-energy shoulder at ~440 nm. The emission spectra of the $BF_2AVB$ spin-cast film at room temperature and after annealing are presented in FIG. 6A. $BF_2AVB$ film morphologies before and after thermal treatments were examined with XRD and atomic force microscopy (AFM). As is clearly shown in FIG. 6B, a sharp peak at 2 θ=5.3° appeared for the heat-treated film, suggestive of crystalline transformation during the annealing process. The details of ordered film regions were also visualized by AFM (FIG. 7). Well-defined rectangular sheet-like aggregates form after thermal treatment of the freshly spun film, which is mostly amorphous. But even prior to thermal treatment, some regions of the film were already crystalline looking, suggesting a strong tendency for ordering.

Based upon the data presented above, we suggest that the yellow emission may arise from the amorphous state of $BF_2AVB$, where excimers may form in mechanically perturbed regions due to greater rotational freedom. Furthermore these excimers may serve as low-energy traps for exciton transfer in the crystals, which may help to explain the observed emission color changes and relative retention of XRD features. This hypothesis can be supported by fluorescence spectroscopy at 77 K, where the freshly smeared regions (that are yellow at room temperature) become green and spectra match the background fluorescence of the unscratched annealed film. The yellow emission is restored in the scratched regions as the sample is warmed back to room temperature.

Since $BF_2AVB$ excimer formation may require conformational change, rigidifying the solid may suppress this process and efficiently reduce the yellow emission from the smeared regions. Finally, although the emission of the smeared region is redshifted, its excitation spectrum is actually blueshifted compared to that of the blue dendritic solid. This suggests that the yellow emission after smearing is due to an excited state effect rather than ground state association.

Morphology dependent fluorescence and unusual reversible mechanochromic luminescence for solid-state $BF_2AVB$ has been discovered by the inventors herein. $BF_2AVB(s)$ shows unexpectedly sharp emission spectra that can be tuned via the solid form, such as single crystals, dendritic solid, or spincast film. Single crystal XRD reveals that $BF_2AVB$ molecules can form multiple emissive aggregation states with different intermolecular interactions. Fluorescence color is dramatically altered after crushing or physically smearing $BF_2AVB$ crystals or upon scratching or rubbing annealed film samples. The mechanochromic fluorescence recovers reproducibly. From a material design standpoint, the fact that the scratched or rubbed region emission fades over time and merges with the background color makes $BF_2AVB$ a self-healing optical material.

Polymorphic and Process Dependent Fluorescence of $BF_2AVB$ $BF_2AVB$ (FIG. 2A) was obtained as yellow crystals and can be processed in many different ways. It was found that two distinct types of crystals, both needle- and prism-like, can be produced by slow evaporation of solvent (e.g., acetone). Under UV excitation, cyan and green fluorescence were observed for the needle (FIG. 2C) and prism (FIG. 2B), respectively. Further investigation of the emission with a fluorometer shows that both crystals have very narrow spectral bands for solid-state dyes. X-ray analysis revealed that cyan and green emitting crystals have different molecular packing.

The solid can also be processed as other forms such as porous solids, films, and nanoparticles suspended in water. All of these physical forms correspond to their characteristic, reproducible emission spectra. For example, a dendritic porous solid of $BF_2AVB$ (FIG. 2D, dendritic structure clearly visualized from SEM images, FIGS. 2E-F) is prepared by the following method: A cotton swab was dipped into a $BF_2AVB$ $CH_2Cl_2$ (5 mg/mL) solution, then removed and let stand for rapid solvent evaporation. With time, a light emitting solid crystallized on the surface of the cotton fibers. Visual inspection of this process revealed that the crystals started to nucleate and grow within minutes in air, and then collapsed onto the cotton swab after the $CH_2Cl_2$ evaporation neared completion. The emission color changed from blue to spotted gold to blue again during this process. The dried solid adsorbed onto the cotton swab surface appeared to have very low density, as the tiny bright blue particles have "fly away" properties from the cotton substrate when the swab is subjected to movement or airflow. The material was harvested by gently tapping the swab over weighing paper or directly into a vial to dislodge the BF$_2$AVB solid. It was also discovered that the substrate that is used to grow these porous solid particles can significantly affect the emission colors of BF$_2$AVB in the solid state. For example, instead of using a cotton swab, if glass wool swab was used, the harvested particles have cyan-green emission color under UV excitation (e.g. cotton swab: blue; glass wool: aqua). In fact, this simple solvent evaporation method can be a practical method for preparing porous materials for inventive solid-state compositions.

A thin layer of film of BF$_2$AVB solid on a glass substrate can be obtained by the solvent spin-coating method. Specifically, a film was formed by dropwise addition of a CH$_2$Cl$_2$ solution of BF$_2$AVB (1 mg/mL) onto a glass substrate at rpm=3000. The emission spectrum of the resulting film is greenish yellow ($\lambda_{em}$=530 nm). Thermal annealing at 110° C. for 5 min however, turned the film emission blue ($\lambda_{em}$=459 nm), similar to the dendritic solid emission except that the thin film shows a high-energy shoulder at ~440 nm. The emission spectra of the BF$_2$AVB spin-cast film at room temperature and after annealing are presented in FIG. 6A. BF$_2$AVB film morphologies before and after thermal treatments were examined with XRD and atomic force microscopy (AFM). As is clearly shown in FIG. 6B, a sharp peak at 2 θ=5.3° appeared for the heat-treated film, suggestive of crystalline transformation during the annealing process. The details of ordered film regions were also visualized by AFM (FIG. 7). Well-defined rectangular sheet-like aggregates form after thermal treatment of the freshly spun film, which is mostly amorphous. But even prior to thermal treatment, some regions of the film were already crystalline looking, suggesting a strong tendency for ordering.

When the blue-emitting BF$_2$AVB dendritic solid (~3 mg) is smeared onto a piece of weighing paper (2×2 in$^2$), it exhibits yellow emission under UV blacklight excitation ($\lambda_{ex}$=365 nm). After a few minutes, the bright yellow fluorescence fades and a greenish emission emerges. This fading process is facilitated by brief heating (~30 s in ~110° C. oven or ~3-5 s with a heat gun), resulting in a green-blue emission color under UV excitation. After thermal annealing, even a small mechanical perturbation, such as a slight touch with the tip of a cotton swab, can change the green-blue BF$_2$AVB film emission to yellow. The yellow emission gradually reverts back to green again at room temperature, with much faster recovery at elevated temperature. After annealing, the written regions are no longer readable. Many other substrates are also possible for achieving this effect, including polymers such as commercial polylactide (PLA), polyethylene (PE), Yupo® synthetic paper, regular paper, glass, and quartz, as described below, each with characteristic sensitivities and recovery behavior. Many other substrates are also possible. It was noticed that in some cases, such as when using polymers as the substrates, the boron dyes may become embedded and integrated with the film, not just on the surface, and harder pressing may be required to observe mechanochromic luminescence. But the advantage in this case, is that physical scratching will not remove the boron dyes from the surface as readily upon rubbing.

Mechanochromic emission changes for solid-state BF$_2$AVB were also investigated by fluorescence spectroscopy. FIG. 5E shows the initial and post-smearing fluorescence spectra for the solid on a quartz substrate as a function of recovery time. Consistent with visual observation, after BF$_2$AVB was smeared, the fluorescence spectrum was drastically broadened with the full width at half maximum (FWHM) increasing from 30 nm to 119 nm. The corresponding emission maximum shifted from 460 nm to 542 nm with a tiny shoulder at ~460 nm which closely matches the starting solid emission. The recovery dynamics are also evident from the spectra recorded at different times. After smearing, the blue shoulder grew (up to 1 h), the main peak gradually blue shifted, and the FWHM decreased with time. The emission color stabilized after ~1 day and could be switched back to yellow emission with smearing. Regardless of the initial state (single crystal or dendritic solid), smeared BF$_2$AVB solids exhibit similar yellow emission and their recovery dynamics are also similar as long as the smeared solid film has approximately the same thickness. (Slower recovery has been observed for thicker films.) FIG. 5F verifies fluorescence "rewritability" of a BF$_2$AVB solid film on a piece of weighing paper.

BF$_2$AVB Solid Used as a Fluorescent Fingerprint Visualization Agent.

Figure 10:
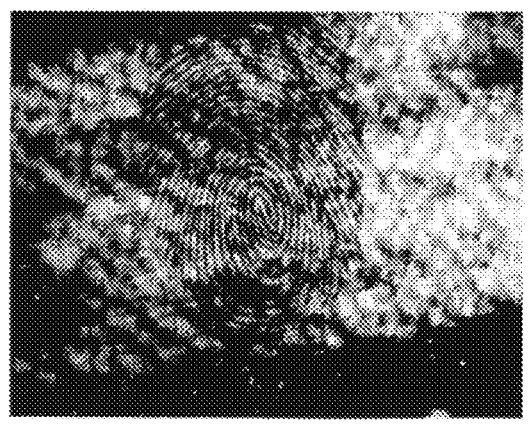
FIG. 10 shows an image of a fingerprint obtained by dusting with BF$_2$AVB. Yellow regions corresponded to smeared compound and also, valleys in fingerprint. Blue regions are either unsmeared dye or contact regions of fingerprint.

We found that BF$_2$AVB is also excellent for fingerprint detection and visualization by two different methods. In the first method, a few milligrams of BF$_2$AVB solid are freshly smeared onto weighing paper. When a finger contacts the solid film, a mark of the fingerprint is left on the film as detected by UV excitation. The contact part appears blue while the "valleys" in the finger that do not contact the paper remain yellow. This could be caused by trace amount of human oil or body heat or some other mechanism. Alternatively, fingerprint patterns can also be made visible under UV excitation in the opposite sequence. That is, first a finger contacts the weighing paper, even quite lightly. Then afterwards it may be gently dusted with BF$_2$AVB solid over the contact region. The contact parts of the fingerprint are blue emitting, whereas the "valleys" not touching the paper remain yellow under UV excitation. (See FIG. 10 below).

Difluoroboron Diketone Dyes and Photophysical Concepts in an Art Folio Project

The solid compounds, shown below, disposed on folio paper, can be mechanically perturbed on the folio paper surfaces to form glowing stripes (cyan, green, orange and violet) under black light illumination. This demonstrates the utility and appeal of these materials for artists, printmakers and designers.

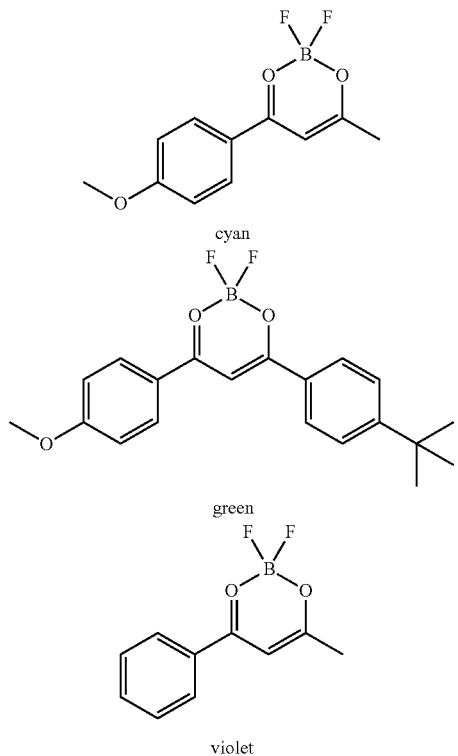

Mechanochromic Luminescence of BF$_2$dbmOC$_{12}$H$_{25}$

We have also discovered fabrication dependent emission and reversible mechanochromic luminescence (ML) for thin films of BF$_2$dbmOC$_{12}$H$_{25}$.

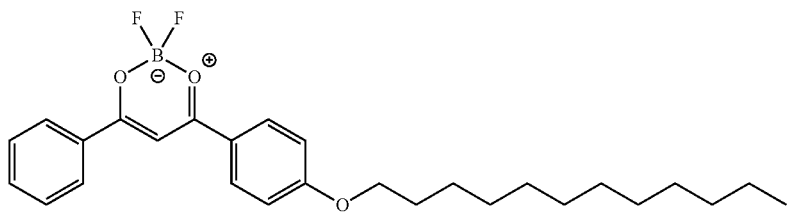 [SMILES: CCCCCCCCCCCCOc1ccc(C2=[O+][B-](F)(F)OC(c3ccccc3)=C2)cc1]

This composition also possesses process dependent emission and reversible mechanochromic luminescence as a solid-state form of the invention, for example see FIG. 8. Compared to $BF_2AVB$, the mechanochromic luminescence of $BF_2dbmOC_{12}H_{25}$ has much faster recovery dynamics (a few minutes) probably due to the better mobility (lower melting point) from the lipid chain at room temperature.

In various embodiments, other structural modifications of the compounds of formula (I) can be used to prepare solid-state forms of the luminescent dyes with a variety of properties. It is within ordinary skill to make and test various crystalline or amorphous solid-state forms of a compound of formula (I) for mechanochromic luminescence, reversibility of the mechanochromic effect, emission spectral parameters, and the like. Along with modifying the ligands (e.g. different arenes, alkyl groups) and substituents (e.g. halide, OR, etc) of compounds of formula (I), and testing many different material processing methods, other steps taken to tune these properties are to vary the length and saturation of the alkyl chain to test the limits of the blueshift and piezochromism, and the transition temperatures and dynamics of these processes. For example, variations in chain length, symmetry, and unsaturation can be made. Additionally, the position of the aromatic nucleus within the alkyl chain environment can be changed by single or multiple alkyl substitutions of both arene rings, i.e., when R is Ar and one or both Ar groups are alkyl-substituted. Other self-organizing units from liquid crystal, supramolecular, model membrane, nanoscience, and other fields can also serve as building blocks with known optical features, physical properties, and structural propensities for attachment to this family of mechanochromic luminescent dyes. Of course, compound polarity and hydrogen bonding also serve as important design features in modifying optical properties that are dependent upon molecular packing in static and dynamic, responsive contexts.

Given the desirable optical properties of $BF_2bdk$ dyes for biology and interest in exploring other organized media known to support room temperature phosphorescence (RTP), we prepared alkyl-substituted dioxaborazines such as $BF_2dbmOC_{12}H_{25}$. When blue-luminescing solids are crushed their emission becomes yellow. Rubbing or scratching on the surface of dye treated weighing paper generates yellow marks that gradually fade over ~2-3 min time, and erasing is faster with heating. Fading rate is thickness, temperature, substrate, and additive dependent.

Mechanochromic Luminescence Additional Examples

Figure 9:
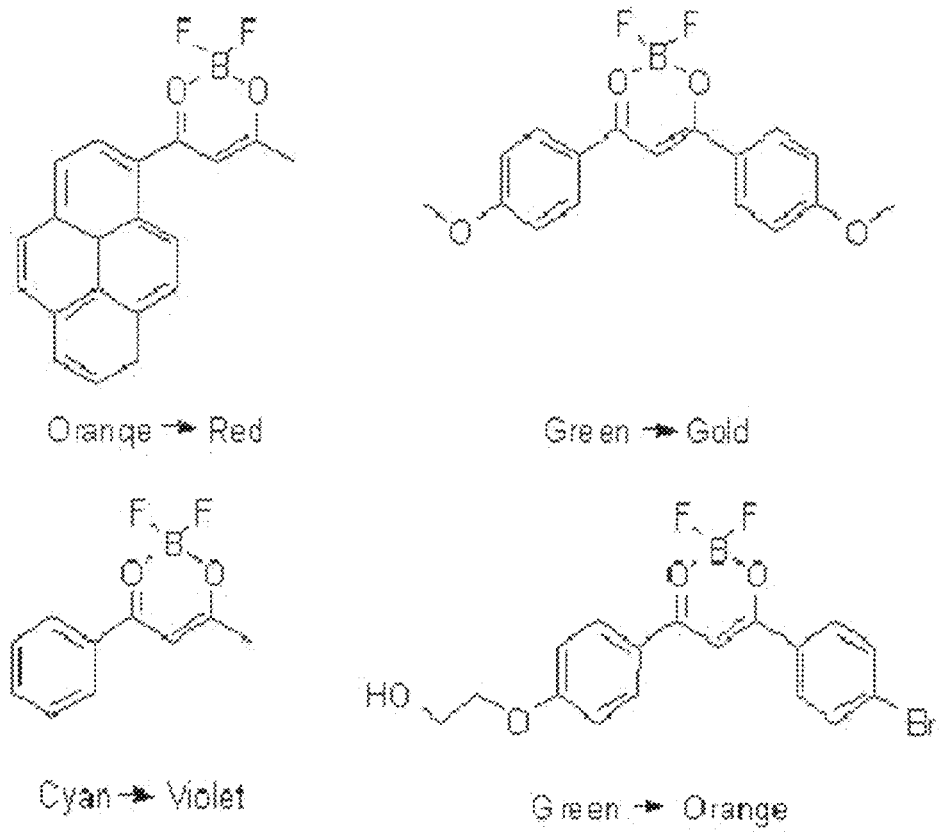
FIG. 9 shows some additional difluoroboron β-diketonates exhibiting mechanochromic luminescence. Emission colors before and after mechanical perturbation are indicated below each chemical structure (before scratching→after scratching). Before scratching emission colors refer to the colors that were observed after thermally annealing the sample but prior to scratching.

Many compositions of the invention exhibit mechanochromic luminescence. Some additional representative examples are shown below in FIG. 9. Recovery rates after scratching are thickness and chemical structure dependent. Typical times for recovering range from minutes to days for thin films (e.g. 2-3 mg on 2×2 in² weighing paper).

A variety of known (see: (1) *Chemistry—A European Journal*, 10(6), 1445-1455, 2004; (2) *Russian Chemical Bulletin, International Edition*, Vol. 57, No. 6, pp. 1190-1193, June, 2008; (3) *Journal of Physical Organic Chemistry* (1996), 9(1), 7-16) and novel compounds of formula (I) having luminescent solid-state forms were evaluated for mechanochromic luminescence, as shown in Table 1, below. Samples shown in the table are in their powder forms. Mechanochromic luminescence (ML) was examined for thermally annealed samples and smeared samples. The X values for thermally annealed and mechanically perturbed (smeared) samples are indicated.

TABLE 1

Mechanochromic luminescence of solid-state compositions

| Sample | Sample | ML? | λ(annealed) | λ(smeared) |
|---|---|---|---|---|
| 1 | *(structure)* | No | | |
| 2 | *(structure)* | Yes | 518 nm | 534 nm |

TABLE 1-continued

Mechanochromic luminescence of solid-state compositions

| Sample | Sample | ML? | λ(annealed) | λ(smeared) |
|---|---|---|---|---|
| 3 | [structure: BF2 complex with phenyl and 2-naphthyl groups] | Yes | 511 nm | 515 nm |
| 4 | [structure: BF2 complex with phenyl and 2-anthracenyl groups] | Yes | 662 nm | 634 nm |
| 5 | [structure: BF2 complex with 4-methoxyphenyl and CH3 groups] | No | 475 nm | 473 nm (broader) |
| 6 | [structure: BF2 complex with 4-methoxyphenyl and phenyl groups] | No | | |
| 7 | [structure: BF2 complex with 4-methoxyphenyl and 2-naphthyl groups] | Yes | 487 nm | 510 nm (broader) |
| 8 | [structure: BF2 complex with 4-methoxyphenyl and 6,7-dimethyl-2-naphthyl groups] | Yes | | |
| 9 | [structure: BF2 complex with two 4-methoxyphenyl groups] | Yes | 494 nm | 533 nm |

TABLE 1-continued

Mechanochromic luminescence of solid-state compositions

| Sample | Sample | ML? | λ(annealed) | λ(smeared) |
|---|---|---|---|---|
| 10 | naphthalen-2-yl with BF$_2$ dioxaborine bearing CH$_3$ | No | | |
| 11 | 4-bromophenyl and naphthalen-2-yl BF$_2$ dioxaborine | Yes | 510 nm | 533 nm |
| 12 | phenyl and 6-bromonaphthalen-2-yl BF$_2$ dioxaborine | No | | |
| 13 | 4-methoxyphenyl and 6-methylnaphthalen-2-yl BF$_2$ dioxaborine | Yes | 510 nm | 537 nm |
| 14 | 4-piperidinophenyl and 6-methylnaphthalen-2-yl BF$_2$ dioxaborine | Yes | 597 nm | 615 nm |
| 15 | 4-piperidinophenyl and 4-hydroxyphenyl BF$_2$ dioxaborine | No | | |
| 16 | 4-bromophenyl and 6-methylnaphthalen-2-yl BF$_2$ dioxaborine | No | | |

TABLE 1-continued

Mechanochromic luminescence of solid-state compositions

| Sample | Sample | ML? | λ(annealed) | λ(smeared) |
|---|---|---|---|---|
| 17 | (structure: BF$_2$ complex with 4-bromophenyl and 4-methoxyphenyl substituents) | Yes | | |
| 18 | (structure: BF$_2$ complex with phenyl and pyrenyl substituents) | Yes | 608 nm | 584 nm |
| 19 | (structure: BF$_2$ complex with two 2-naphthyl substituents) | Yes | 515 nm | 523 nm (broader) |
| 20 | (structure: BF$_2$ complex with 6-methoxy-2-naphthyl and 3,4-dimethylphenyl substituents) | Yes | 530 nm | 571 nm |

Mechanochromic luminescent (ML) systems are rare, but ones that self-erase at well below the melting point and can be rewritten many times (FIG. 5) may be unprecedented. Initially we thought that the $C_{12}$ tail might be important for ordering and the ML recovery process, however even crystalline BF$_2$AVB (see above), exhibits this feature, and both dyes also display morphology and process dependent emission. For BF$_2$AVB, blue (FIG. 2), cyan and green crystalline forms were isolated and single crystal XRD analysis reveals different molecular packing for cyan and green polymorphs. For spin cast films, initial green emission for amorphous samples becomes narrow bandwidth blue (FWHM=30 vs 47 nm for CH$_2$Cl$_2$ solution) upon ordering via thermal annealing, suggestive of J-aggregates. Given that scratching leads to redshifted fluorescence, it was reasoned that it too, decreases the singlet-triplet energy gap, and as with heavy atom systems, might facilitate intersystem crossing. In fact, this is what we observed for I-substituted BF$_2$dbm(I)OC$_{12}$H$_{25}$, namely, increased triplet intensity with mechanical perturbation under air-free conditions. Under air, phosphorescence is quenched and scratched regions become dark, resulting in a new method for generating a mechanically induced negative image. One hypothesis is that the ML effect in solid-state boron dyes arises from excimer emission from molecules released from the constrained crystal lattice.

Effects of Aryl Substituents on Mechanochromic Luminescence

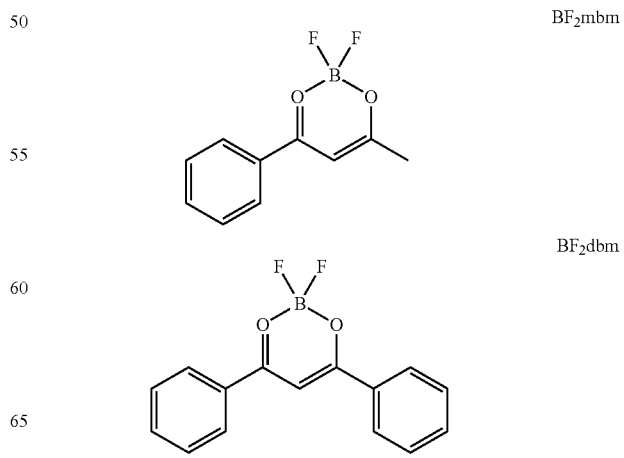

BF$_2$nbm

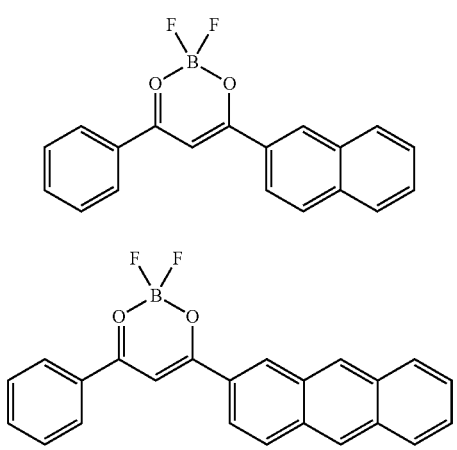

BF$_2$abm

Figure 12:
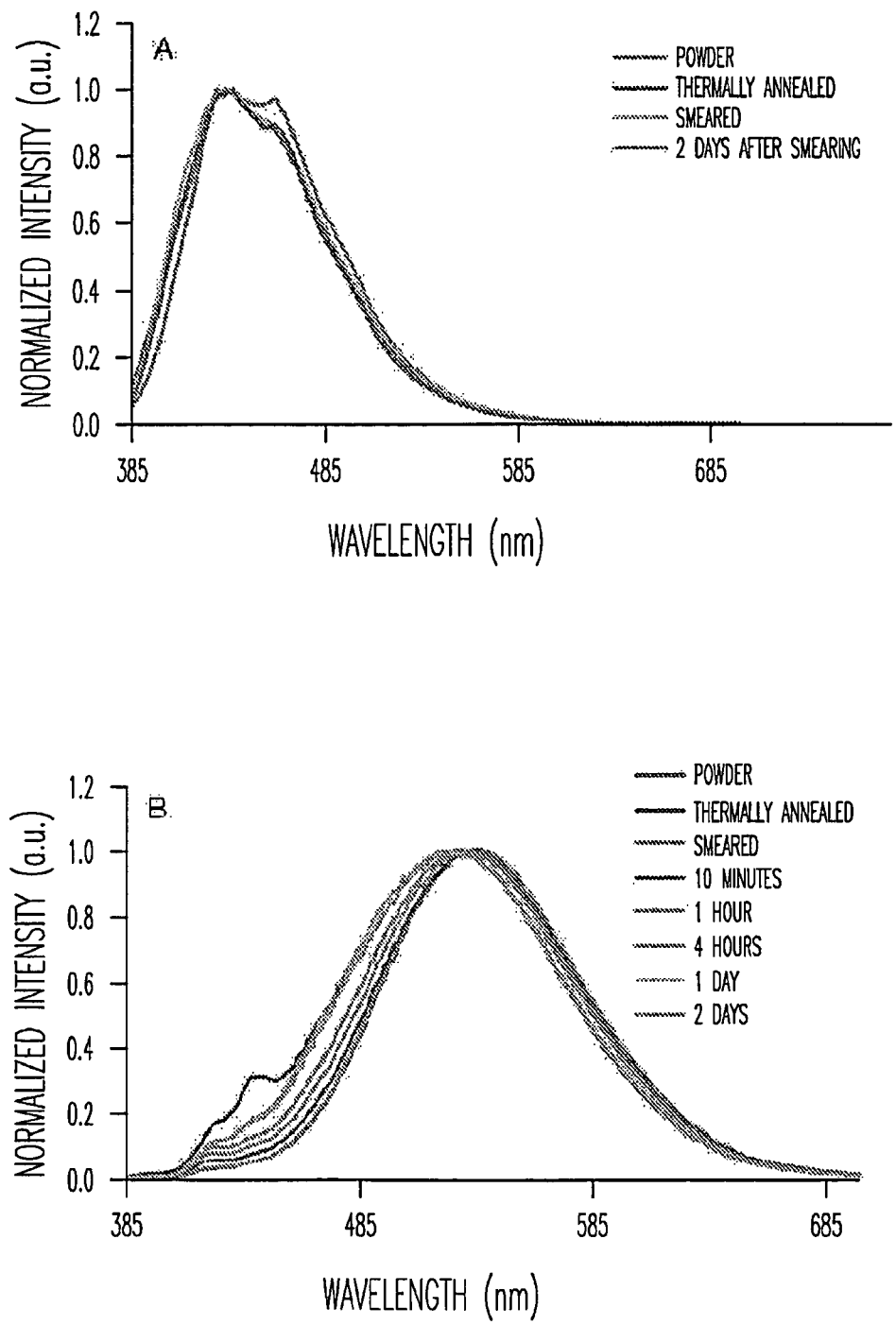
FIG. 12 shows normalized emission spectra of $BF_2mbm$, $BF_2dbm$, $BF_2nbm$, and $BF_2abm$ powders on quartz: (A) $BF_2mbm$, $\lambda_{ex}$=369 nm; (B) $BF_2dbm$, $\lambda_{ex}$=369 nm; (C) $BF_2nbm$, $\lambda_{ex}$=369 nm; (D) $BF_2abm$, $\lambda_{ex}$=397 nm.

The above compounds BF$_2$mbm, BF$_2$dbm, BF$_2$nbm, and BF$_2$abm were prepared as described in the Examples section and in accordance with Schemes 2A, 2B, and 2C, shown below. The crystalline BF$_2$mbm and BF$_2$dbm showed significant change in emission when they were smeared to powders (FIGS. 11A, 11B). For example, the crystalline BF$_2$dbm has two emission peaks at 446 nm and 522 nm respectively. To distinguish mechanochromism from the size dependent emission, powders of the above four compounds were coated on cuvettes to diminish the influence of sample size. Their emission properties under mechanic stimuli were investigated. (see FIG. 12). As a comparison, amorphous solid-state forms of the above four compounds were prepared on cover glass via spin casting and their mechanochromic luminescence are shown in FIG. 13. Data are summarized in Table 2 (from FIG. 12) and Table 3 (from FIG. 13), below.

Scheme 2A

Synthesis of BF2nbm

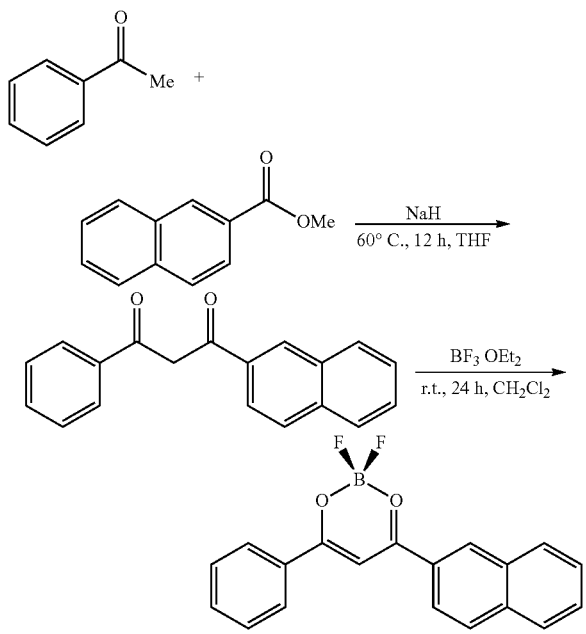

Scheme 2B

Synthesis of BF2mbm, BF2dbm

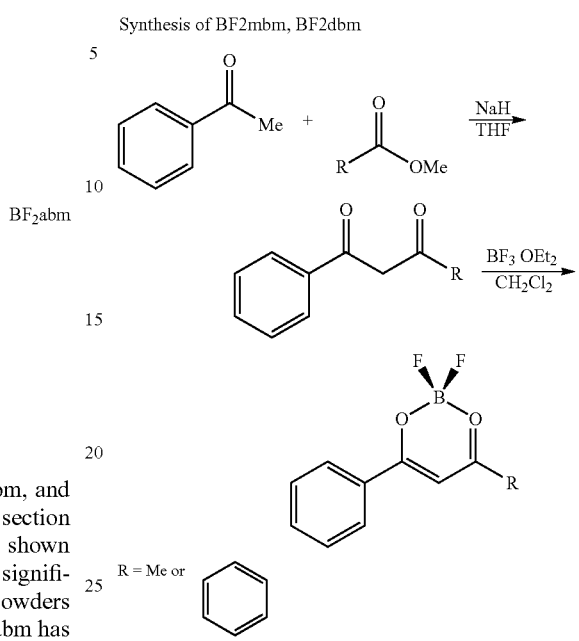

R = Me or [phenyl]

Scheme 2C

Synthesis of BF2abm

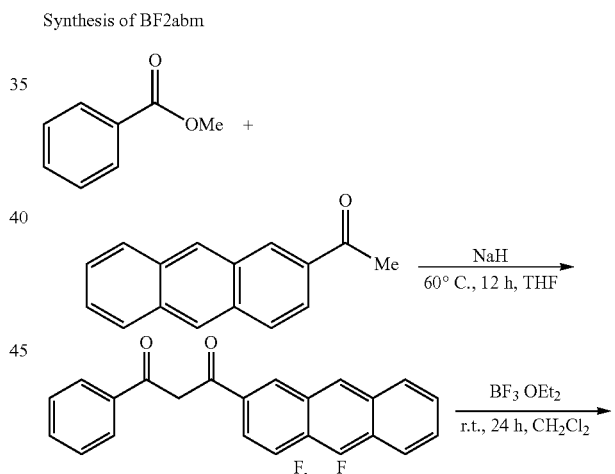

TABLE 2

Emission maxima and bandwidths for powders on quartz.

| BF$_2$bdk | $\lambda_P$ (nm) | $\lambda_{TA}$ (nm) | $\lambda_S$ (nm) | fwhm$_P$ (nm) | fwhm$_{TA}$ (nm) | fwhm$_S$ (nm) |
|---|---|---|---|---|---|---|
| BF$_2$mbm | 433 | 429 | 434 | 87 | 87 | 90 |
| BF$_2$dbm | 531 | 529 | 534 | 100 | 110 | 101 |

TABLE 2-continued

Emission maxima and bandwidths for powders on quartz.

| BF$_2$bdk | $\lambda_P$ (nm) | $\lambda_{TA}$ (nm) | $\lambda_S$ (nm) | fwhm$_P$ (nm) | fwhm$_{TA}$ (nm) | fwhm$_S$ (nm) |
|---|---|---|---|---|---|---|
| BF$_2$nbm | 512 | 511 | 515 | 63 | 63 | 95 |
| BF$_2$abm | 643 | 622 | 634 | 117 | 115 | 117 |

$P$ = powder;
$TA$ = thermally annealed;
$S$ = smeared;
fwhm = full width at half maximum

TABLE 3

Emission maxima and bandwidths for spin-cast films on glass.

| BF$_2$bdk | $\lambda_A$ (nm) | $\lambda_{TA}$ (nm) | $\lambda_S$ (nm) | fwhm$_A$ (nm) | fwhm$_{TA}$ (nm) | fwhm$_S$ (nm) |
|---|---|---|---|---|---|---|
| BF$_2$mbm | 434 | 435 | 433 | 83 | 79 | 82 |
| BF$_2$dbm | 534 | 531 | 541 | 100 | 109 | 102 |
| BF$_2$nbm | 502 | 487 | 516 | 96 | 76 | 109 |
| BF$_2$abm | 641 | 584 | 636 | 123 | 162 | 117 |

$A$ = amorphous;
$TA$ = thermally annealed,
$S$ = smeared;
fwhm = full width at half maximum It is thus shown that the aromatic groups have dramatic influences on the fluorophores' ML properties. Besides the emission wavelength changes, the aromatic group identity influences the details of the mechanochromic luminescence, e.g., the wavelength shift after application of pressure and the recovery rate at various temperatures. Samples processing methods can also affect their ML behaviors.

The emission spectra of BF$_2$mbm has a major peak at 433 nm accompanied by a shoulder peak at 459 nm. The shoulder emission of its powder species was slightly increased after thermally annealing at 110° C. for 10 min (FIG. 12A). Mechanical pressure removed the enhancement of the shoulder peak, and resulted in emission spectra overlap with the spectrum of the sample before annealing. Amorphous BF$_2$mbm is even less responsive to mechanical force. (FIG. 13A) Its emission spectra are nearly identical after treatment either with annealing or smearing. Thus, BF$_2$mbm can not be considered mechanochromic mechanochromic on this substrate and under these particular processing conditions.

FIG. 12B and FIG. 13B show the ML behavior of BF$_2$dbm. The emission spectrum of crystalline BF$_2$dbm after mechanic perturbation was nearly identical to that before annealing. The low wavelength emission emerged under annealing disappeared, which can be interpreted as the crash of the aggregated species. The time-resolved emission kept moving gradually the short wavelength region until the main emission overlap with that of the thermally annealed sample. The amorphous sample's behavior is similar. Notably, recovery dynamics of BF$_2$dbm on various substrates have significant differences. The recovery of the spin cast film only lasted less than 2 hours, whereas the powders on cuvettes took up to 1 day. Though it was suggested that multiple factors could contribute to ML, but thermal annealing may be the most important issue. Clearly, BF$_2$dbm aggregated and formed a thermally preferred structure, which induced the hypsochromic shift. Mechanical force caused the thermally stable structure to shrink and break the aggregated species. This process is represented by the red-shift in emission after the smearing. Multiple interactions, such as strong dipolar nature, offset arene stacking, steric effect and other interactions may promote BF$_2$dbm to regain the thermally preferred configuration.

BF$_2$nbm exhibits different ML properties. With respect to the sample on a quartz substrate (FIG. 12C), emission did not show any change before and after thermally annealing. However, the emission peak was drastically broadened after smearing; the fwhm was increased from 62 nm to 96 nm. Surprisingly, the emission maxima did not shift as a response to the mechanic perturbation and remained at 513 nm. The emission spectrum after mechanical perturbation is similar to the original emission spectrum. The band was broadened and the interdimeric emission was increased. In the first 10 minutes after smearing, a small shrinkage of the emission band emerged, but the spectra then remained unchanged up to 2 days. BF$_2$nbm is stable after smearing. The extension of the aromatic ring system has profound influence on the ML properties. It can not only affect the emission maxima, but also determine the recovery of the luminescence. BF$_2$abm showed the most distinct emission change upon smearing. Emission maxima shift from 622 nm to 634 nm for the powder sample, and from 584 nm to 628 nm for the amorphous species. Both emissions for the smeared samples moved towards the thermally annealed emission, but the recovery rates are dramatic different. It takes up to 1 day for the powder sample, but only 1 hour for the amorphous BF$_2$abm. In both cases, the shoulder emission cannot be retrieved. Similar to BF$_2$dbm, the aggregation of the dye cannot happen at room temperature.

Thermal annealing is one of the key factors that can be useful in producing arene samples exhibiting ML properties. A direct mechanic perturbation was applied to unannealed solid-state forms of the above compounds as a film on cover glass. Their emission spectra showed much less change compared to the annealed samples.

In another comparative study, a series of BF$_2$dbmOR derivatives (where R=C$_n$H$_{2n+1}$ and n=1, 2, 3, 5, 6, 12, 14, 18) were synthesized, and their luminescent properties in the solution and solid-state were studied by fluorescence spectroscopy, lifetime measurements, XRD, and AFM.

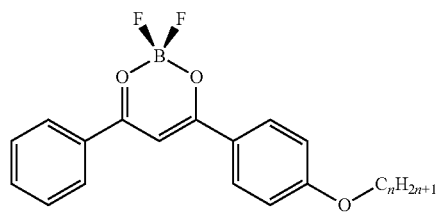

Compounds of the BF$_2$dbmOR series are designated C$_n$, wherein n is the number of carbon atoms in the alkoxyl substituent. BF$_2$dbmOR compounds were synthesized via standard Claisen condensation of the appropriate alkoxyacetophenone with methyl benzoate, followed by boronation in CH$_2$Cl$_2$ and purification by column chromatography and recrystallization. See Examples, below. All the compounds were obtained as yellow powders with solid-state emission colors ranging from yellow to cyan upon UV excitation (365 nm). In $CH_2Cl_2$ solution, all the dyes exhibit high extinction coefficients, ranging from 50,100 to 66,200 ($M^{-1}$ $cm^1$). All the compounds displayed absorption maxima at 399 nm and emission maxima at 435±1 nm (fwhm ~52 nm) with high quantum yields (>82%) and similar fluorescence lifetimes (~2.0 ns) (Table 4, below). The data shown in Table 4 indicate that increasing the alkyl chain length of the alkoxy group does not substantially affect the photophysical properties in solution.

TABLE 4

Optical measurements for compounds $C_n$ in solution ($CH_2Cl_2$).

|  | $\epsilon$ ($M^{-1}$ $cm^{-1}$) | $\lambda_{abs}$ (nm) | $\lambda_{em}$ (nm) | $\Phi_F$ | $\tau_F$ (ns) |
|---|---|---|---|---|---|
| C1 | 51,900 | 399 | 434 | 0.93 | 2.05 |
| C2 | 56,800 | 399 | 436 | 0.91 | 2.04 |
| C3 | 65,100 | 399 | 435 | 1.00 | 2.10 |
| C5 | 51,000 | 399 | 436 | 1.00 | 2.03 |
| C6 | 50,100 | 399 | 437 | 1.00 | 2.04 |
| C12 | 51,600 | 399 | 439 | 1.00 | 2.02 |
| C14 | 66,200 | 399 | 437 | 0.94 | 2.05 |
| C16 | 58,100 | 399 | 438 | 0.82 | 2.05 |
| C18 | 57,700 | 399 | 436 | 1.00 | 2.02 |

Solid-State Photophysical Properties.

Contrary to the solution optical properties, the solid-state PL properties varies significantly when altering the chain length of alkoxy group. Table 5, below, summarizes solid state luminescence data for $C_n$ films, prepared by evaporation and by spin-casting.

TABLE 5

Solid-state fluorescence data summary for of $C_n$ dyes films.

|  | Evaporated films[a] | | Spin-cast film | | | |
|---|---|---|---|---|---|---|
|  | | | TA[e] | | AS | |
|  | $\lambda_{em}$[b] | $\tau_f$[c] | $\lambda_{em}$[b] | $\tau_f$[c] | $\lambda_{em}$[b] | $\tau_f$[c] |
| C1 | 544 | 36.96 (96.53%), 6.81 (3.47%) | 540 | 44.52 (80.48%), 25.74 (19.52%) | 544 | 43.26 (86.48%), 23.50 (13.52%) |
| C2 | 473 | 5.11 (45.77%), 7.96 (47.30%), 1.50 (6.93%) | 497, ~470[d] | 8.32 (70.98%), 14.40 (22.56%), 2.40 (6.46%) | 499 | 10.28 (77.42%), 18.89 (15.99%), 3.06 (6.59%) |
| C3 | 501 | 3.51 (60.27%), 6.70 (38.87%), 2.64 (0.05%) | 482, ~460[d] | 4.95 (45.29%), 8.72 (45.26%), 1.33 (9.45%) | 523 | 43.85 (63.52%), 12.71 (27.25%), 2.65 (9.22%) |
| C5 | 491 | 5.45 (72.34%), 10.91 (15.39%), 1.62 (12.27) | 453, ~470[d] | 4.23 (45.10%), 1.12 (41.00%), 13.33 (13.90%) | 511 | 16.00 (40.61%), 4.06 (4.80%), 34.52 (54.59%) |
| C6 | 483 | 6.14 (65.08%) 10.93 (17.58%), 2.37 (17.55) | 478, ~460[d] | 5.31(65.42%), 1.86 (22.46%), 12.41 (12.12%) | 506 | 10.96 (51.38%), 23.22 (37.07%), 2.98 (11.55%) |
| C12 | 474 | 6.32 (81.22%), 2.45 (10.05%), 13.17 (8.72%) | 466, ~450[d] | 5.88 (77.02%), 13.58 (12.51%), 1.91 (10.47%) | 504 | 29.83 (56.03%), 9.96 (30.97%), 1.26 (13.00%) |
| C14 | 480 | 5.08 (62.45%), 2.01 (30.36%), 11.8 (7.19%) | 457, ~470[d] | 5.87 (78.70%), 1.79 (11.48%), 1.24 (9.82%) | 510 | 39.38 (52.44%), 14.59 (39.75%), 2.91(7.81%) |
| C16 | 475 | 5.08 (71.83%), 1.94 (16.04%), 10.29 (12.22%) | 470, ~450[d] | 3.26 (70.00%), 1.35 (24.09%), 8.44 (5.91%) | 507 | 35.23 (51.91%), 10.64 (10.64%), 2.23 (12.93%) |
| C18 | 479 | 1.41 (58.85%), 3.33 (39%), 1.32 (3.71%) | 472, ~450[d] | 3.60 (59.27%), 1.46 (34.52%), 13.97 (6.21%) | 518 | 43.86 (59.77%), 13.47 (30.34%), 2.60 (9.89%) |

[a]Evaporated films were formed by allowing a solution of 2 mg/mL of $C_n$ in $CH_2Cl_2$ to slowly evaporate under ambient conditions in small glass vials.
[b]$\lambda_{em}$ are given in nm units.
[c]Lifetimes are given in nsec unless otherwise noted. (TAC range = 200 ns except for $C_1$)
[d]Shoulder peaks.
[e]Thermally annealing was done at 110° C. for five minutes.

Table 6, below, summarizes solid state luminescence data for $C_n$ powders, thermally annealed and smeared.

TABLE 6

Solid state fluorescence summary for of $C_n$ dyes powders.

|  | Powders[a] | Smeared powders | | | |
|---|---|---|---|---|---|
|  |  | TA | | Smeared | |
|  | $\lambda_{em}$ | $\lambda_{em}$ | $\tau_f$ | $\lambda_{em}$ | $\tau_f$ |
| C1 | 550 | 544 | 36.25 (68.40%), 18.39 (31.60%) | 544 | 36.36 (73.05%), 18.44 (26.96%) |
| C2 | 507 | 472 | 5.47 (67.63%), 9.60 (22.94%), 1.48 (9.43%) | 509 | 9.33 (40.98%), 33.92 (42.94%), 1.92 (16.07%) |
| C3 | 500 | 488 | 11.8 (60.32), 5.92 (32.67%), 1.06 (6.71%) | 527 | 6.98 (48.89%), 25.71 (34.26%), 1.39 (17.25%) |
| C5 | 496 | 491 | 8.80 (76.69%), 16.4 (20.30%), 1.94 (2.98%) | 514 | 31.1 (53.60%), 12.3 (38.75%), 2.4 (7.65%) |
| C6 | 489 | 475 | 4.50 (58.84%), 1.14 (20.67%), 11.5 (20.49%) | 494 | 8.86 (50.64%), 21.8 (39.00%), 1.77 (10.33%) |
| C12 |  | 473 | 5.88 (60.55%), 16.66 (19.00%), 1.82 (20.45%) | 496 | 33.80 (57.63%), 12.46 (34.39%), 2.17 (7.98%) |
| C14 |  | 476 | 5.32 (69.46%), 1.73 (16.32%), 12.8 (14.22%) | 501 | 31.91 (50.84%), 9.90 (35.01%), 1.79 (14.45%) |

TABLE 6-continued

Solid state fluorescence summary for of $C_n$ dyes powders.

| Powders[a] | TA | | Smeared powders Smeared | |
|---|---|---|---|---|
| | $\lambda_{em}$ | $\lambda_{em}$ | $\tau_f$ | $\lambda_{em}$ | $\tau_f$ |
| C16 | 471 | 470 | 4.15 (58.30%), 1.49 (29.33%), 10.54 (12.05%) | 508 | 31.93 (50.77%), 9.92 (35.05%), 1.79 (14.18%) |
| C18 | 473 | 472 | 2.99 (54.33%), 0.65 (34.27%), 11.2 (11.40%) | 506 | 35.15 (53.72%), 11.54 (34.18%), 1.79 (12.10%) |

[a]Powders were prepared by recrystallization method with 1:1 $CH_2Cl_2$/Hexanes The evaporated thin films were formed by allowing solutions of 2 mg/mL of $C_n$ in $CH_2Cl_2$ to slowly evaporate in small vials. Naked eye observation revealed the resulting crystalline solid compound $C_1$ emits in yellow region, compounds $C_2$ and $C_{12-18}$ in blue region and compounds $C_{3-6}$ in blue-green region upon UV excitation (365 nm). Even though compounds $C_2$ and $C_{12-18}$ show similar emission maxima (~475 nm), careful inspection of the emission spectra further reviewed that compounds $C_{12}$-$C_{18}$ possess broader spectral peaks (fwhm (nm)=58, 80, 66, 78, respectively) when compared with compound $C_2$ (fwhm=58 nm). Meanwhile, comparison between compounds $C_2$-$C_6$ also shows interesting effects of structure on properties. Different emission maxima observed for these compounds probably suggest a variety of molecular packing orientations induced by the different chain lengths of the alkoxy group. In summary, the solid-state luminescent behaviors or the compound $C_n$ analogues are not only governed by π-π interaction but also alkyl chain length. This is consistent with previous finding, which showed that different intermolecular interactions, such as H-bonding also influence the solid-state orientation. Lifetime measurement showed multiexponential decays, but there is not a real trend observed for these dyes, probably due to extremely complex decay pathways associated with solid-state luminescence.

Emission for as-spun (AS) or unannealed (UA) and thermally annealed (TA) films displayed different emission spectra (Table 5). AS and TA films were fabricated from 1 mg/mL solutions of dyes in $CH_2Cl_2$, and annealing was conducted at 110° C. for 5 minutes. It was found that the emission spectra of compounds $C_1$ and $C_2$ do not change from AS to TA solid-state forms, however the band features are different among the solid-state forms of the two compounds. While compound $C_1$ displayed a broad, structureless band with $\tau_f$=44 ns and close to single exponential decay, TA $C_2$ films possessed a narrower band with blue-shifted maxima and shorter lifetime (~8 ns) (Table 5). In addition, all other $C_n$ AS films also show broad, unstructured peaks with $\lambda_{em}$=~510 nm (except for C3, whose $\lambda_{em}$=~530 nm) and long lifetimes ($\tau_F$ ranges from 23 to 44 ns) which can be fitted to 2-3 exponentials, indicative of a more complex decays compared with $C_1$, probably due to multiple emissive species in the AS films. Thermally annealing induced a hypsochromic shift for all $C_{3-18}$, with the shift ranges from 30 to 60 nm and with much shorter lifetime ($\tau_F$=~5 ns) which can be fitted to 2-3 exponentials. Surprisingly, only $C_5$ showed a very sharp peak at 453 nm, which is very close to one of the $BF_2AVB$ crystal forms (above).

In addition, we also investigated the ML behaviors of smeared powder (Table 6) on quartz surface to further understand processing method effects and thickness effects on this phenomenon. Similar behaviors were observed as for spin-cast films, i.e., sheared powder is red-shifted compared to TA powders, with much longer lifetimes that were also fitted to multiexponential decays. Only compounds $C_2$ and $C_5$ TA sheared powders displayed significant differences compared with TA spin-cast films. For example, $C_2$ displayed ML. Sheared powder emit in orange-green region and TA blue-shift the emission maxima to blue (~475 nm). Furthermore, $C_5$ TA sheared powder considerably red-shifted compared to TA thin films ($\lambda_{em}$=453 vs. 491 nm), and slightly longer lifetime (τ=4.23 ns vs 8.80 ns). On the other hand, $C_6$ and $C_{12}$ sheared powders were blue-shifted as compared to AS films. Reasons are not known for these behaviors, but it appeared that when alkyl chain length in the middle range (n=5, 6, 12), thickness and processing dependent effects are more readily observable.

Figure 15:
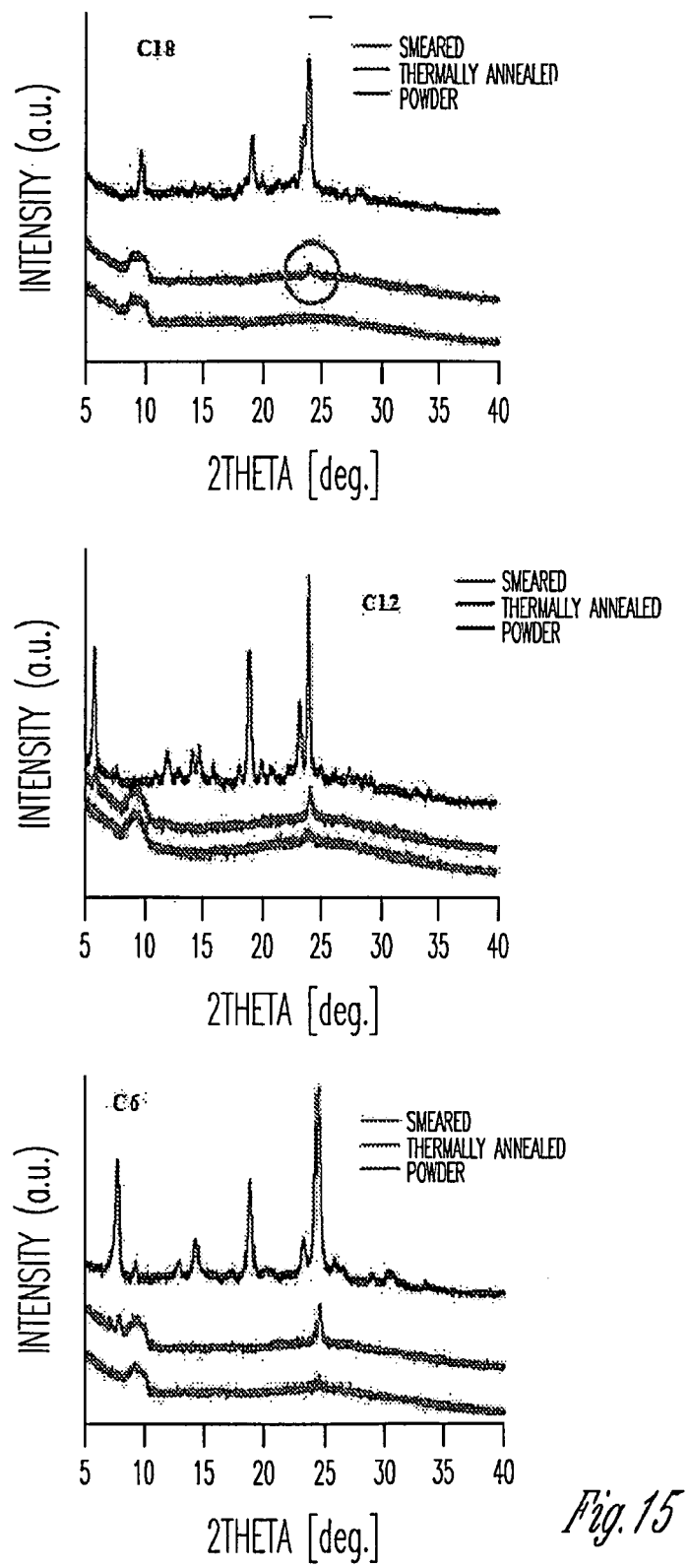
FIG. 15 shows XRD scans of powders of $C_6$, $C_{12}$, and $C_{18}$ as powders (green), sheared (red) and TA (blue) on a glass substrate. For $C_{18}$, a very small change is observed and is marked with a circle.

To further understand this phenomenon, XRD and AFM was employed to visualize microstructures of amorphous and TA solid-state forms of the compounds. A representative image for AFM is shown for $C_5$ (FIG. 14). As observed with $BF_2AVB$, TA induced crystallization of the spin-cast films. This is further confirmed by XRD (FIG. 15). The smeared samples are mostly amorphous and TA caused the crystallization (indicated by the small peaks). After TA a sheared powder, we observed emergence of small peaks at ~6° and 24° for $C_{12}$, ~8° and 24° for $C_6$, and a very small peaks at 24° for $C_{18}$ (FIG. 15). The powder diffraction patterns show that compounds $C_6$, $C_{12}$ and $C_{18}$ probably have very similar crystal structures, noting the three strongest peaks on the powders' spectra. However, no noticeable changes occurred for $C_2$ although optical changes were observed when preparing the samples. The thin films after TA may have crystalline regions, however the crystal size is too small for an observable change in optical properties. Indeed, spin-cast films for $C_2$ showed crystals formed after thermally annealing.

A study was carried out to determine the approximate minimum pressures needed to induce visible mechanochromism in two representative species of this series of compounds. Samples of compounds C3 and C18 (~2.5 mg each) were evenly applied to a 5 cm×5 cm weighing paper using cotton swab tips, then thermally annealed at ~110° C. for 1 min. The weighing paper was then placed on a weighing pan of a balance, pressure applied using a fresh cotton swab, and visible mechanochromism under UV illumination observed. For compound C3, a pressure resulting in a weight measurement of ~20-30 gm produced a strong mechanochromic effect, at a pressure resulting in a weight measurement of ~6-7 gm the mechanochromic effect was still observable. At pressures resulting in a weight measurement of less than about 5 gm, no significant mechanochromic effect was observed. For compound C18: ~20-30 gm again produced a strong mechanochromic effect; ~10 gm produced a small mechanochromic affect, and <10 g produced no observable mechanochromism under UV illumination.

Time Frames for Reversibility of Mechanochromic Luminescence (ML)

As noted above, all $C_n$ except $C_1$ displayed ML. Upon smearing on quartz substrate, the solid-state forms displayed a bathochromic shift to orange and luminescent spectra displayed broad, structureless bands resembling that of the $C_1$ crystalline emission. We ascribed the spectral shifts from ML to structural transition. Previously, we observed for $C_{12}$ and $BF_2AVB$ analogues spontaneous recovery at ambient condition, with ~3 hrs for a thin film of $C_{12}$ and ~1 day for $BF_2AVB$ on quartz surface. In addition, long lipid alkyl chains are known to be capable of aggregation, therefore it is interesting to test for the effects of the chain length on spontaneous ML recovery process. For compound $C_2$, thermally annealing (TA) previously smeared layers on quartz cuvettes led to blue (475 nm) emission. Upon shearing, the blue dye layers turned orange (~510 nm) and exhibited a significant increase in fluorescence lifetime (from 5.4 ns to 33.6 ns). At this stage, spontaneous recovery time takes ~18 hrs at room temperature (about 20° C.) to revert to the stable, TA-and-cooled, state (~475 nm). $C_3$ and $C_5$ display quite similar behaviors when compared with $C_2$. Following smearing, the dyes also exhibit orange emission and then spontaneously blue-shift back to the stable form, with $C_3$ faster than $C_5$ (25 mins and ~1 days, respectively). Smearing $C_6$ and $C_{12}$ also turns the sample orange, but $C_6$ and $C_{12}$ revert back to green emission quickly, <1 sec, and then gradually blue-shifted and completely stopped after ~9 days for $C_6$ but did not revert back to the properties of original TA form. Compound $C_{18}$ does not self-heal to green immediately and the process takes a relatively long time (>20 days). For compounds $C_3$-$C_{18}$, we observed a consistent trend with the alkyl chain length, i.e., increasing recovery time with longer alkyl chains.

In various embodiments, the invention provides a method of preparing the luminescent solid-state composition of the invention comprising forming a solution in an organic solvent of a compound of formula (I), then removing the solvent by evaporation. For example, the solvent can be removed using a spin-casting process, such as to provide a film of the solid-state form of the compound of formula (I) on a substrate. Examples are provided below.

Products prepared by a process of the invention can comprise luminescent films that display mechanochromism when transiently placed under a pressure of about 1 gm/cm² or greater; for example under a pressure of about 10 gm/cm² or of about 100 gm/cm², i.e., in the range of about 0.1 to 1 kPa of pressure or tension. In various embodiments, the mechanochromism can be bathochromic. As described above, the mechanochromism can be reversible, such as thermally reversible. More specifically, the mechanochromism can be thermally reversible at about 20° C. over a period of about 15 minutes to 24 hours.

Compositions Containing Heavy Atoms and Intersystem Crossing $BF_2$dbm molecules display strong excited state interactions that can affect fluorescence. Previously, this phenomenon was studied in a polymer matrix, where $BF_2$dbm was covalently attached to a polylactide (PLA) chain. Singlet excited state energy dropped most dramatically for short $BF_2$dbmPLA chains (i.e. stronger fluorophore-fluorophore interactions). A material with tunable fluorescence-to-phosphorescence (F/P) ratios was also achieved based on this model. When the polymer chain is shorter, the excited state interactions are stronger, the singlet state energy decrease is more significant, and the singlet-to-triplet intersystem crossing is enhanced, especially in the presence of an iodide internal heavy atom. This material design concept was successfully applied to ratiometric oxygen sensing for optical tumor hypoxia imaging with the versatile boron dye-polymer system fabricated as nanoparticles. If the singlet excited state energy can also be lowered after mechanical stimulation, enhanced intersystem crossing is expected here too. Here we extend the F/P tuning concept to non-polymeric boron diketone complexes in the solid state, where the triplet process is enhanced mechanically.

The luminescent boron complex, $BF_2$dbm(I)$OC_{12}H_{25}$, was synthesized via Claisen condensation followed by boronation in $CH_2Cl_2$. A bright yellow waxy solid (m.p.=144-146° C.) was obtained after silica-gel chromatography. The lipid derivative was chosen to increase both the solubility of the iodide dye and the possible organization of the boron complexes in the solid state, given that material ordering can play an important role in ML. The optical properties of 1 were studied in $CH_2Cl_2$ solution. The absorption ($\lambda_{max}$=409 nm) and emission ($\lambda_F$=446 nm) spectra are similar to those for a reported $BF_2$dbm(I) derivative but the fluorescence lifetime ($\tau_F$=1.50 ns) and quantum ($\Phi_F$=0.67) yield of 1 have increased values.

If this ML quenching behavior at room temperature is indeed due to increased triplet quenching (e.g. oxygen or collisional), an increase in relative phosphorescence intensity would be expected at low temperature, where these processes are hindered. At room temperature, the normalized emission spectra of 1 before and after smearing are similar. At 77K, however, the smeared sample shows a much stronger peak around 570 nm. To confirm that the lower energy peak corresponds to phosphorescence, delayed emission spectra (Δt=1 ms) were collected for the thermally annealed and smeared films of 1 both at room temperature under $N_2$ and at 77 K. At room temperature, the two delayed spectra are almost identical with emission maxima at 560 and 558 nm, respectively. At 77 K however, the maxima are red-shifted by ~10 nm to 567 and 571 nm. The red-shift in delayed emission spectra at lower temperatures has been previous ascribed to a diminished contribution from delayed fluorescence (blue-shifted relative to the phosphorescence peak), where thermal back population from triplet to singlet excited states is inhibited. Overlapped excitation spectra at 77 K monitored at the two peak intensities ($\lambda_F$=500 and $\lambda_F$=570 nm) also indicate that these features arise from the same species.

These results suggest that for smeared solid films of 1, the triplet excited state population is indeed increased. As has been discussed before, Eq. 1 explains how a decreased energy gap in the presence of a heavy-atom can enhance the singlet ($^1\Psi$)-triplet($^3\Psi$) mixing and thus, the intersystem crossing. For $BF_2$AVB, without a heavy-atom effect, only a bathochromic shift in fluorescence was observed upon mechanical perturbation. In the case of a solid film of 1, mechanical force is likely to induce the same singlet energy drop, however, with iodide substitution, this also corresponds to an increased fraction of the singlet excited-state species crossing over to the triplet excited state. At room temperature, the triplet excited state for the dye-lipid derivative may be quenched by oxygen or may preferentially decay by thermal pathways.

$$\delta = \frac{<^3\Psi|H_{so}|^1\Psi>}{|E_1 - E_3|} \qquad (1)$$

If this hypothesis is true, this enhanced intersystem crossing may also be reflected in a reduced fluorescence lifetime

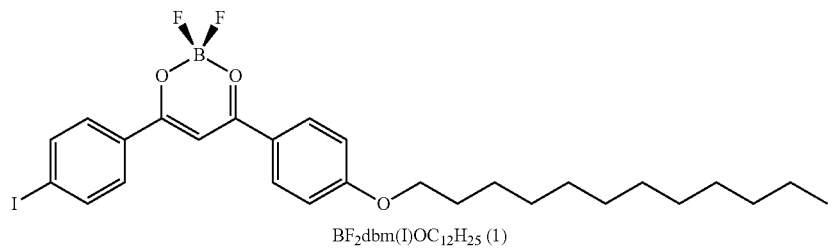

$BF_2$dbm(I)$OC_{12}H_{25}$ (1)

($\tau_F$) for the smeared sample. Indeed, when monitored at the peak intensity (500 nm), a reduction of $\tau_F$ from 1.63 to 1.31 ns was recorded after smearing. However, the decrease in $\tau_F$ could be due to enhanced intersystem crossing from increased excited-state interactions or due to exciton migration. To better understand the mechanism, the $\tau_F$ of $BF_2dbmOC_{12}H_{25}$, a control compound of 1 without iodide substitution, was also measured. Comparison of $\tau_F$ values in $CH_2Cl_2$ (1: 1.50 ns vs control: 2.05 ns) indicates a higher ISC efficiency for 1. When monitored at the emission maximum, $\lambda_F$=466 nm, for solid films the control $\tau_F$ increases from 6.69 to 11.27 ns upon smearing, suggesting changes in excited state energy. To explore whether exciton migration is also involved, we measured $\tau_F$ of the control at a higher wavelength. A consistent increase in lifetime from 7.26 to 13.28 ns was also recorded when the emission was monitored at 530 nm but no initial rise in the decay profile characteristic of exciton migration was observed. This does not rule out exciton migration, however, given that our lifetime instrument (>200 ps) may not reveal fast processes.

Heavy-atom substituted difluoroboron dibenzoymethane-lipid dye exhibits mechanosensitive intersystem crossing and reversible mechanochromic luminescence quenching (MLQ) in the solid state. Under UV excitation, the relative ratio of singlet to triplet excited state populations is decreased when a solid film of the dye is smeared or scratched. One possible explanation is that mechanical processes lower the singlet excited state energy level, and thus increase the degree of singlet and triplet state coupling according to perturbation theory. Luminescence under $N_2$ at room temperature and 77 K shows that the relative intensity of phosphorescence increases in the smeared solid film. This increase corresponds nicely to the drop in fluorescence intensity at room temperature under air, suggesting near complete emission quenching upon mechanical perturbation. This unique force induced method of altering intersystem crossing (in combination with heavy atoms such as I, Br, etc) may be useful in the design of luminescent mechanical sensors.

This property can be used not just for sensing oxygen levels (or stated a different way, atmospheres or environments that are oxygen depleted due to vacuum or the presence of a different gas), such as cause rapid emission quenching (e.g., rapid singlet state to triplet state intersystem crossing), but for a process wherein one wishes to generate a negative image wherein a scratched or perturbed area does not luminesce. Scratching of a film or surface formed of a heavy atom containing solid-state mechanochromic luminescent composition in the presence of oxygen or some other known triplet quencher will result in creation of a negative type image, wherein the scratched region is dark and does not luminesce. Multi-Component Systems as Light Bridge Concept By properly choosing different dioxaborazine compounds, the mechanochromic luminescence range can be significantly increased by means of solid-state energy transfer. For a representative example, a binary system comprised of $BF_2bmm$ (w/w 95%) and $BF_2AVB$ (w/w 5%) solids can be obtained by grinding them together in the solid state or by dissolving the two dyes together and evaporating the solvent.

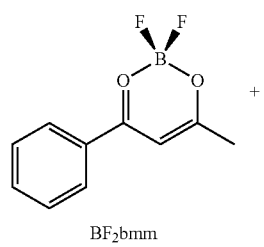

BF$_2$bmm

-continued

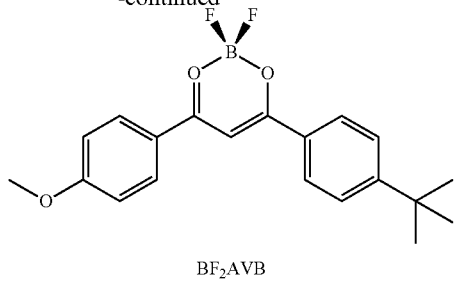

BF$_2$AVB

When the blended composition is smeared onto a piece of weighing paper, the emission color resembles that of the $BF_2AVB$ monosystem under UV light. However, after the solid film is thermally annealed, the emission is deep blue which is characteristic of the $BF_2bmm$ solid. It is possible that energy transfer is restricted after thermal annealing when both solids are more crystalline and possibly microphase separated. In the case of the smeared solid film, amorphous states promote the excited-state energy transfer from the high energy (shorter wavelength) to the lower energy (long wavelength) emitting dye.

In various embodiments, more than two components can be comprised by a "light-bridge" mixture of the invention. The alteration of the luminescent properties is not only applicable for mixtures of two difluoroboron β-diketonates but also for one or more difluoroboron β-diketonates with one or more compounds of other varieties of light-absorbing or luminescent organic compound, such as Rhodamine B (RB), an orange fluorescent dye that is wisely used in biological studies. Mixtures of one or more difluoroboron β-diketonates with additional light-absorbing or luminescing compound(s) which can be selected from one or more structural classes are also provided by the invention.

For example, a mixed composition was prepared by dissolving 0.5% w/w RB and 99.5% w/w $BF_2AVB$ in acetone and drying the mixture. Crystals with a pink hue were obtained which display a dim orange emission color under UV light. Note that RB alone is not emissive in the solid state. Surprisingly, when the solid mixture was smeared onto a piece of weighing paper, instead of the yellow emission observed for $BF_2AVB$, an orange emission, typical of RB in polar solvent was observed. When the film was heated with a heat gun, the emission color of the solid film turned aqua, which was much more blueshifted than the $BF_2AVB$ film alone after thermal annealing. Scratching or rubbing the surface resulted in intense orange emission. Similarly to the $BF_2AVB$ monospecies system, the RB doped film also self-recovered at room temperature. However, the emission color does not revert back to aqua without heating but rather dims down and remains orange. Heating is required to completely erase scratch marks, and to makes the entire surface luminesce an aqua color again. In essence, the scratched regions, presumably amorphous, serve as a light bridge for energy transfer to lower energy RB. Interestingly and counter intuitively, under a nitrogen stream, the emission intensity of the freshly smeared region became darker.

Figure 16:
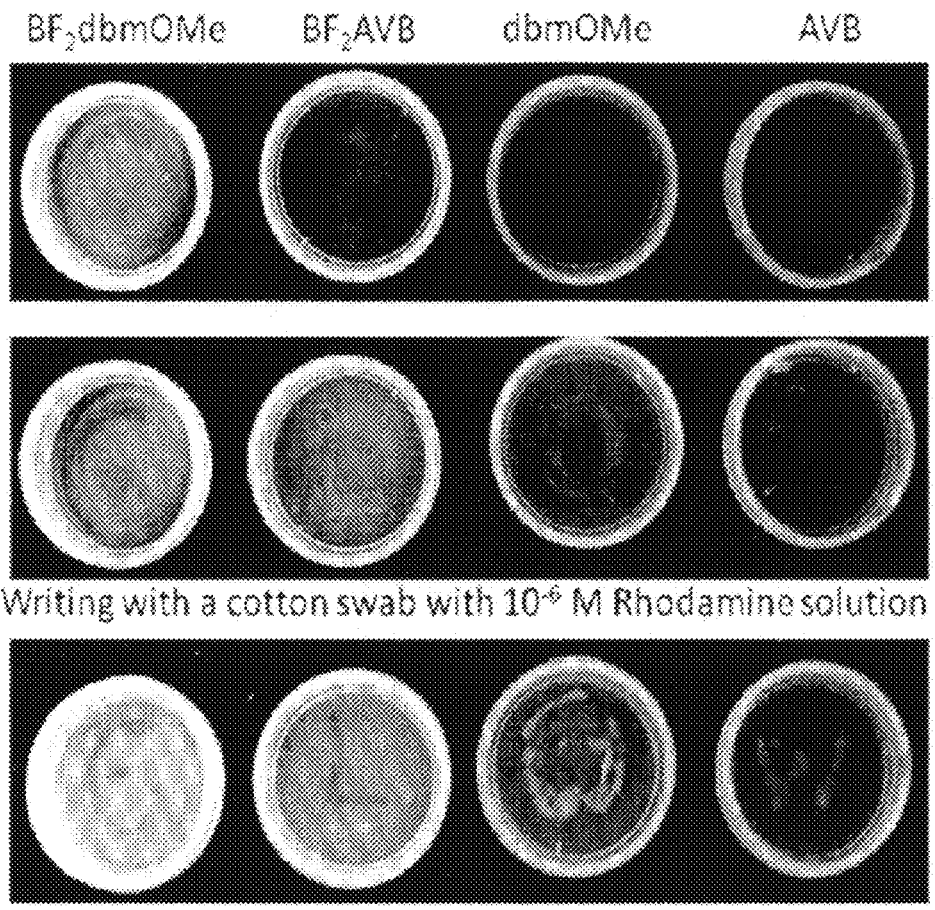
FIG. 16 shows mechanochromic luminescence effects for each of the four compositions $BF_2dbmOMe$ and $BF_2AVB$ (both difluoroboron β-diketonates) and dbmOMe and AVB (both β-diketones) in the four columns, with no Rhodamine B (first row), $10^{-6}$ M Rhodamine B (second row) and $10^{-5}$ M Rhodamine B (third row) under UV illumination, mechanically perturbed by handwriting one of the letters G, L, O, or W with a cotton swab tip.

For example, see FIG. 16, which shows mechanochromic luminescence effects for each of the four compositions $BF_2dbmOMe$ and $BF_2AVB$ (both difluoroboronate compounds) and dbmOMe and AVB (β-diketones not including a difluoroboronate) in the four columns, with no Rhodamine B (first row), $10^{-6}$ M Rhodamine B (second row) and $10^{-5}$ M Rhodamine B (third row) under UV illumination, mechanically perturbed by handwriting one of the letters G, L, O, or W with a cotton swab tip. For $BF_2AVB$ solid films, the typical emission maxima range is ~460 (annealed) to ~540 nm (scratched). Therefore the emission from the scratched film matches well with RhB absorption and may result in efficient energy transfer. To test the idea, we prepared spin-cast films of $BF_2AVB$ and $BF_2dbmOMe$. The latter complex is not mechanochromic but structurally similar to $BF_2AVB$. As controls, the weakly fluorescent films of AVB and dbmOMe diketones were also fabricated. The optical properties of these solid films were first studied by steady-state fluorescence spectroscopy and lifetime measurements. Then the films were immersed in aqueous solutions of RhB (10 mL each, $10^{-6}$ M or $10^{-5}$ M) for ~3-5 s and then washed thoroughly with distilled water and dried before fluorescence measurements. The data before and after RhB solution treatment are presented in FIG. 16.

In various embodiments, a method of the invention can further comprise dissolving a second luminescent compound in the solution prior to removing the solvent. This can be used to prepare a "light-bridge" embodiment wherein two or more luminescent solid-state forms are present. As discussed above, the "light-bridge" in various embodiments can comprise a β-diketone either in free form, or as a difluoroboronate, in combination with a second luminescent material, for example, a Rhodamine dye such as Rhodamine B. The combination of luminescent compounds enables illumination to be provided at a wavelength sufficient to excite the diketone or derivative, but emission is influenced by the presence of the second luminescent material. Indeed, the second luminescent material need not be normally luminescent in the solid state itself, but energy transfer ("light bridging") takes place between the β-diketone or its difluoroboron derivative and the second luminescent material such that emission occurs at least in part from the second luminescent material.

Uses: Displays and Display Devices

In various embodiments, the invention provides a mechanochromic luminescent solid state display system or device comprising the composition of the invention or a composition prepared by the method of the invention. A display system or device comprises a mechanochromic luminescent solid state form, such as a reversibly mechanochromic solid-state form of a difluoroboron β-diketonate compound of the invention suitably disposed, such as on a substrate, or in bulk within a container, along with an illumination system for inducing luminescence in the material. A suitable illumination system can comprise a ultraviolet light source, such as long wave ultraviolet light, that can cause luminescence to occur in the device. some embodiments, the device also includes a system for detecting the luminescence and/or a change in luminescence. For example, a pressure sensor can include a solid-state display device of the invention, wherein the pressure to be measured or detected is mechanically transmitted to the solid-state composition, which is illuminated by the ultraviolet light source, and the response luminescence transmitted to a recording or measuring device that can, for example, detect the emission spectrum of the material. For example, a pressure sensor comprising a display device of the invention can include a fiberoptic system both for illumination of the composition and for detection of the emissive response of the material, which varies as a function of pressure. The emissive response can be detected and its significance determined by a human operator, by a computer system, or the like. Similarly, as it is known that the luminescent properties of various embodiments of the composition can be affected by the presence of oxygen, an oxygen sensor can embody similar concepts of an illumination system, a detection system, and a means of transmitting light to and from the composition, which is itself disposed in the environment in which the oxygen concentration is to be measured. For example, an oxygen sensor for use in an atmospheric environment that might also contain flammable or explosive gases could include a sample of an inventive composition disposed in a gas-permeable container, and a fiber-optic illumination and detection system. Such a device would offer the advantage of having no electrical current present in the sensor which could itself induce an explosion of the dangerous gas component.

In various embodiments of a display device of the invention, the composition can be present as a film. For example, the composition can be disposed as a film, such as behind a protective sheet of transparent material such as plastic through which a mechanical force can be transmitted. If the film is thus coated, the coating should be sufficiently flexible to allow application of a mechanical force such as that of a person drawing with a stylus or other similar device. Alternatively, pressure can be applied directly to the film provided it is of sufficient hardness and durability to withstand the physical contact. In various embodiments, the device can be a component of any of an art, design or consumer product comprising a responsive, intentionally fading, fugitive fluorescent pigment; a toy or novelty item; an optical sensing/detection device for detecting a mechanical event; a self-erasing reusable notesheet; or a display board for permanent or impermanent information. By selection of a suitable composition, a display can self-erase over a suitable time period at room temperature, or can persist indefinitely at room temperature but be erasable at an elevated temperature, such as with a heat gun or an iron.

For example, a film of an inventive composition could be used, such as with a protective coating and a means of illumination, for transient display of useful information to readers. A specific example is a menu board in a restaurant, where the mechanochromic luminescence was adapted to persist for, say, several hours, but would reverse and provide a fresh writing surface by the next morning. A restaurant staffer, wishing to display the specials of the day, could write the information on the surface of the display board and illuminate the board with ultraviolet light, such that the information was attractively presented. Such a board could be designed to present the information in various colors under UV illumination through the use of suitably selected compositions of the invention. The display would persist for a usable period of time, but would self-erase (or could be erased such as by application of moderate heat) in time for the next day's specials to be presented.

These mechanosensor materials compositions could be very important for intelligence applications too, where messages could be written and disappear or be intentionally erased within given time frames, and the reader would need to know the appropriate developing compound (e.g. RhB) or illuminating device (UV) to read the message. Additionally they could be used to detect whether a barrier has been breached or object has been tampered with, given the material provides a record of mechanical events, and the duration of this message is readily tunable with chemistry and physical conditions. The materials can be used in different combinations requiring decoding in different mechanical or chemical ways, given different aforementioned dye combination effects (e.g. scratch as light bridge between two or more compositions to generate a particular luminescence color or visual effect).

Another example might be a graffiti or "self-expression" board, where students or passersby could write their sentiments on an issue of the day, or provide amusing art work, or the like, in a medium that slowly faded over time, thus allowing fresh surfaces to be automatically provided as time went by. Or, such a board could be used for scheduling workers, for example, for a dispatcher in a trucking, delivery, or taxi business, where transient information could be displayed for a suitable period of time, then self-erase to provide a fresh medium for the next round of information to be presented.

Yet another example might be an article of apparel adapted to be worn in an environment where ultraviolet illumination would be present, such as a night club or a rave event. The article of apparel, for example, a shirt, would luminesce under the UV light and present a surface whereupon entertaining, informative, or amusing things could be written or pictures could be drawn, such as with a finger or a stylus, for example a list of dance partners for the evening. The self-erasing composition could then be reused from time to time. By selection of a suitable composition, a garment where the writing self-erased from body heat over a period of minutes to hours could be obtained. Alternatively, the garment could require a higher degree of heat to erase, such as by ironing.

In other embodiments, the invention provides a biological probe system comprising the composition of the invention or a composition prepared by the method of the invention wherein an emission luminescence of the composition or described mixtures of compositions provides information about a biological environment in a cell or tissue. For example, the dyes or bdk ligands of which they are comprised, combined with RhB, and application of pressure or force (e.g. by a dispenser, applicator, RhB inked pen/writing device) could be used for biotechnological assays, to detect RhB and other energy acceptor analytes, e.g. deriving from a RhB labeled biomolecule, cell or tissue extract. In any other example, implantation of microscopic particles, such as nanoparticles, of a solid-state composition of the invention or introduction of dyes that can form assemblies or ordered aggregates in biological systems, could be used in conjunction with fluorescence microscopy to provide information about micro-conditions within a mechanically active living cell or tissue, such as temperature or pressure or oxygen levels (for heavy atom substituted systems) in that micro-environment. In various embodiments, the solid-state compositions of the invention, such as in a nanoparticulate or nanoassembly form or dyes on surfaces or matrices discussed below, are responsive mechanochromically to pressures or tensions in the range of about 0.1 to about 5 kilopascals (kPa), such as are exerted by cells acting on external surfaces as discussed above, or to forces within cells which would be expected to be of similar magnitudes. In other embodiments, cells, tissues, or organisms could interact with a surface or matrix external to the living tissue, such that the response of the mechanochromic composition on the surface or in a dye containing matrix could provide information about the biological subject, e.g., a bird or animal walking on a surface, or the grip of a cephalopod's suckers, or gecko, or the like. In this way, the composition serves as a biomechanical sensor.

In various embodiments, the invention provides a kit for detection of fingerprints or other biological samples deposited on a surface, comprising a solid-state composition of the invention or a composition prepared by the method of the invention and, optionally, an application system and/or a UV light source. As discussed above, the solid-state compositions in powder or film form are sensitive detection media for skin oils or other biological materials and can be used to aid in their detection and visualization on surfaces. Synthetic oils (e.g. from lotions, soaps, personal care products) and compounds could also be thus detected. For example, an aerosol preparation of an inventive composition can be sprayed on a surface as fingerprint detection powder, and the sprayed area examined under ultraviolet illumination and photographed to provide a permanent record of a fingerprint or the like disposed on that surface.

In various embodiments, the invention provides novel difluoroboron diketonates that can be used in a solid-state form as an optionally reversibly mechanochromic luminescent composition. Such compounds include any of the following:

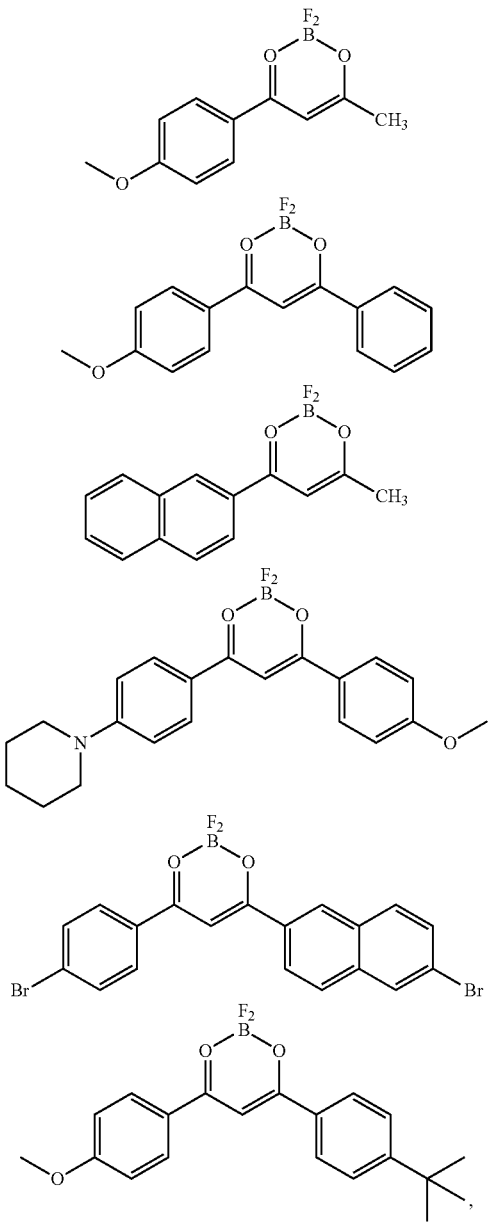

or a compound of formula

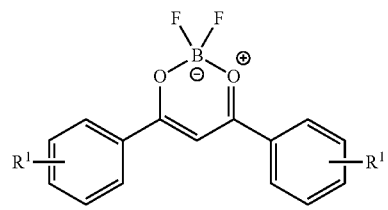

wherein each independently selected $R^1$ is C1-C24 alkyl or C1-C24 alkoxy, wherein any alkyl or alkoxy can be unsubstituted or can be mono- or independently multi-substituted with J;

or any salt thereof.

Examples

Materials

Solvents $CH_2Cl_2$ and THF were dried and purified by passage through alumina columns. Boron trifluoride diethyl etherate (Aldrich, purified, redistilled) and all other reagents and solvents were used as received without further purification.

Methods.

$^1$H NMR (300 MHz) spectra were recorded on a UnityInova 300/51 instrument in $CDCl_3$ unless indicated otherwise. $^1$H NMR spectra were referenced to the signal for residual protio chloroform at 7.26 ppm and coupling constants are given in hertz. UV/vis spectra were recorded on a Hewlett-Packard 8452A diode-array spectrophotometer. Elemental analysis was performed by Atlantic Microlab, Inc., Norcross, Ga. The melting point of $BF_2AVB$ was measured with a MeI-Temp II (Laboratory Devices, USA) melting temperature apparatus coupled with a mercury thermometer with a heating rate of ~5° C./min. A Laurell Technologies WS-650S spin-coater was used to cast $BF_2AVB$ films (1 mg/mL in $CH_2Cl_2$) for fluorescence, X-ray diffraction, and AFM measurements. Steady-state fluorescence emission spectra were recorded on a Horiba Fluorolog-3 Model FL3-22 spectrofluorometer (double-grating excitation and double-grating emission monochromator). Time-correlated single-photon counting (TCSPC) fluorescence lifetime measurements were performed with a NanoLED-370 (369 nm) excitation source and DataStation Hub as the SPC controller. Lifetime data were analyzed with DataStation v2.4 software from Horiba Jobin Yvon. Fluorescence quantum yields, $\Phi_F$, for $BF_2AVB$ in $CH_2Cl_2$ was calculated versus anthracene in EtOH as a standard as previously described using the following values: $\Phi_F$ anthracene=0.27, $n_D^{20}$ EtOH=1.360, $n_D^{20} CH_2Cl_2$=1.424. Optically dilute $CH_2CH_2$ solution of $BF_2AVB$ and EtOH solution of the anthracene standard were prepared in 1 cm path length quartz cuvettes with absorbances <0.1. Both absorption and steady state fluorescence spectra ($\lambda_{ex}$=350 nm; emission integration range: 365-700 nm) were averaged over three runs. Fluorescence microscopy images were obtained on a Leica SP5 X imaging system coupled to DMI6000 epifluorescence microscope excited with a blue laser ($\lambda_{max}$=405 nm). Scanning electron microscopy images were obtained from a JEOL JSM-6700F scanning electron microscope equipped with a cold field-emission electron source. Spincast film X-ray diffraction (Smart-Lab®, Rigaku Inc., Japan) used the Cu Kα radiation wavelength (0.154 nm). The scan was theta-2 theta, ranging from 4 to 40 degrees with a step size of 0.01 degree. Tappy mode AFM (DI 3000, Digital Instrument, CA) was used to characterize the morphology of spin cast films with a scan rate of 0.5 Hz over an area of 10×10 µm².

Difluoroboron Avobenzone ($BF_2AVB$).

AVB was prepared by standard Claisen condensation under basic conditions. Methyl 4-tert-butylbenzoate (7.68 g, 40.0 mmol) in THF (50 mL) and sodium hydride (1.19 g, 50.0 mmol) in THF (100 mL) were transferred via cannula to a round-bottom flask containing 4-methoxyacetophenone (5.00 g, 33.3 mmol). After refluxing under $N_2$ at 60° C. for 18 h, the reaction mixture was quenched by dropwise addition of saturated $NaHCO_3$(aq) in an ice bath. The pH of the solution was adjusted to ~3-4 with 1M HCl(aq), THF was removed in vacuo and the aqueous suspension was extracted with EtOAc (2×100 mL). The combined organic layers were dried over $Na_2SO_4$ and the solvent was removed in vacuo to yield a dark oil. The crude product was crystallized in EtOAc/MeOH to form off-white crystals. AVB was collected by filtration, washed with cold MeOH and dried in vacuo (4.96 g, 48%). $^1$H NMR ($CDCl_2$) δ 7.98 (d, 2H, J=8.8, 2',6'-ArH), 7.92 (d, 2H, J=8.7, 2",6"-ArH), 7.50 (d, 2H, J=8.7, 3",5"-ArH), 6.98 (d, 2H, J=8.8, 3',5'-ArH), 6.78 (s, 1H, COCHCO), 3.89 (s, 3H, $CH_3OAr$), 1.36 (s, 9H, $(CH_3)_3COAr$). AVB (4.00 g, 12.9 mmol) was added to a flame-dried 2-neck round bottom flask under nitrogen, and dissolved in $CH_2Cl_2$ (100 mL) to give a pale yellow solution. Boron trifluoride diethyl etherate (2.20 mL, 15.5 mmol) was added via syringe and the solution turned bright yellow instantly. The flask was equipped with a reflux condenser and heated in an oil bath at 60° C. (1 h). The reaction mixture was then cooled to room temperature and the solvent was removed in vacuo. The crude product was first purified by flash silica-gel chromatography in $CH_2Cl_2$ to remove polar impurities and then recrystallized in acetone to give $BF_2AVB$ as bright yellow crystals: 2.70 g (59%). $^1$H NMR ($CDCl_3$) δ 8.15 (d, 2H, J=9.0, 2',6'-ArH), 8.06 (d, 2H, J=8.8, 2",6"-ArH), 7.55 (d, 2H, J=8.8, 3",5"-ArH), 7.07 (s, 1H, COCHCO), 7.02 (d, 2H, J=9.0, 3',5'-ArH), 3.93 (s, 3H, $CH_3OAr$), 1.37 (s, 9H, $(CH_3)_3COAr$). M.p. 234-236° C. Anal. calcd for $C_{20}H_{21}BF_2O_3$: C, 67.07; H, 5.91. Found: C, 67.14; H, 5.92. UV/vis ($CH_2Cl_2$): $\lambda_{abs}$=402 nm, $\epsilon$=51,200 M$^{-1}$ cm$^{-1}$.

Crystals (Green and Cyan).

$BF_2AVB$ (50 mg) was dissolved in hot acetone (~3 mL) in a glass vial to make a saturated solution. Insoluble solid was removed by hot filtration and the filtrate was transferred to another glass vial. The vial was capped with a piece of Kim Wipe secured with a rubber band for slow evaporation. The cyan and green emitting crystals typically grew for 6-10 h before they reached a size suitable for single crystal x-ray diffraction experiments. The crystals were harvested from the wall and bottom of the vial through gentle swirling, collected by filtration using a glass frit and then separated based on emission color with the aid of a handheld UV-lamp. The crystals were dried in vacuo (~15 h) prior to fluorescence and XRD measurements.

Dendritic Solid (Blue).

A cotton swab was dipped into a $BF_2AVB$ $CH_2Cl_2$ (5 mg/mL) solution, then removed and let stand for rapid solvent evaporation. With time, a light emitting solid crystallized on the surface of the cotton fibers. Visual inspection of this process revealed that the crystals started to nucleate and grow within minutes in air, then collapsed onto the cotton swab after the $CH_2Cl_2$ evaporation neared completion. The emission color changed from blue to spotted gold to blue again during this process. The dried solid adsorbed onto the cotton swab surface appeared to have very low density, given the tiny bright blue particles have "fly away" properties from the cotton substrate when the swab is subjected to movement or airflow. The material was harvested by gently tapping the swab over weighing paper or directly into a vial to dislodge the unique $BF_2AVB$ solid. The light yellow solid particles were then harvested and dried in vacuo for at least 6 h before SEM and fluorescence measurements.

$BF_2dbm(I)OC_{12}H_{25}$

A reaction flask containing 4-hydroxyacetophenone (5.00 g, 36.7 mmol) and 1-bromododecane (10 mL, 41.7 mmol) in NaOH (aq) (1.55 g, 38.7 mmol in 100 mL $H_2O$) was heated at 110° C. under $N_2$ for overnight under reflux. The organic layer was then extracted with hexanes and purified by silica gel chromatography with hexanes to result in colorless 4-dodecyloxyacetophenone crystals (6.63 g, 59%). The diketone ligand was then synthesized through standard Claisen condensation from 4-dodecyloxyacetophenone and methyl 4-iodobenzoate in NaH/THF suspension. Specifically, methyl 4-iodobenzoate (0.786 g, 3.00 mmol) in THF (15 mL) and sodium hydride (0.096 g, 4.00 mmol) in THF (15 mL) were transfer to a round-bottom flask containing 4-dodecyloxyaceto-phenone (0.608 g, 2.00 mmol) via cannula. After refluxing under N₂ at 60° C. for 18 h, the reaction mixture was quenched by drop wise addition of saturated NaHCO₃ (aq) in an ice bath. The pH of the solution was adjusted to ~3-4 by 1M HCl(aq) and then THF was removed on vacuo to give a dark oil. The crude diketone ligand was then dissolved in CH₂Cl₂ (30 mL) under N₂, BF₃·OEt₂ (400 μL, 3.00 mmol) was added to the solution via a Hamilton syringe, and the reaction was refluxed under N₂ at 60° C. for 6 h. The reaction was quenched with triethylamine (1 mL). The dark red solution was passed through a silica column with CH₂Cl₂ to give a bright yellow solution. The pure boron complex product 1 was obtained by silica column chromatography one more time from 50:50 EtOAc/hexanes (0.424 g, 37%). M.p. 144-146° C. ¹H NMR (CDCl₃) δ 8.14 (t, 2H, J=9.1, 2",6"-ArH), 7.91 (t, 2H, J=8.8, 2',6'-ArH), 7.81 (t, 2H, J=8.8, 3', 5'-ArH), 7.05 (s, 1H, COCHCO), 7.02 (d, 2H, J=9.1, 3",5"-ArH), 4.08 (t, 2H, J=6.6, RCH₂OAr), 1.83 (m, 2H, J=6.6, RCH₂CH₂OAr), 1.48 (m, 2H, J=6.6, RCH₂CH₂CH₂OAr), 1.27 (s, broad, 16H, CH₃(CH₂)₈CH₂CH₂OAr), 0.88 (t, 3H, J=6.6, CH₃ROAr). HRMS calcd for C₂₇H₃₅BO₃F₂₁Na (M+Na): 605.1506. Found: 605.1501; UV/vis (CH₂Cl₂): λ$_{max}$=409 nm, ε=62,500 M⁻¹ cm⁻¹.

Additional Mechanochromic Luminescent Compounds and their Syntheses Synthesis of

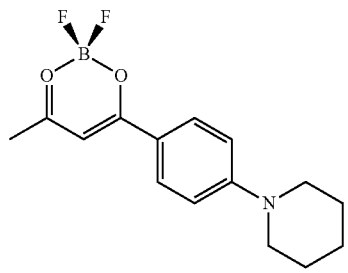

A round bottom flask and stir-bar was flame-dried three times while under vacuum. It was then filled with nitrogen, and 1.8 mL of ethyl acetate and 0.75 g of 4-piperidonacetophenone were dissolved in DCM in said flask. The flask was placed in a dry ice-isopropanol bath, under nitrogen. After a few minutes, 2.7 mL of room-temperature 1.76 M LDA was added to the flask. The reaction was run for 24 hours. The ice bath was removed 12 hours in to improve reactivity. Reaction progress was measured with TLC. The reaction was quenched with HCl and an extraction done with DCM. The DCM layer was rotovapped. The resulting solid was run through a silica gel column to obtain light tan flaky crystals. Purity was verified via ¹H NMR with d-chloroform as a solvent to provide the diketone of structure

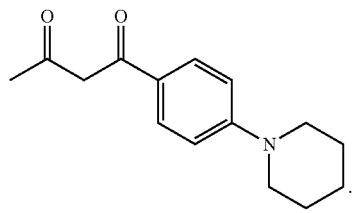 [SMILES: CC(=O)CC(=O)c1ccc(N2CCCCC2)cc1]

Figure 17:
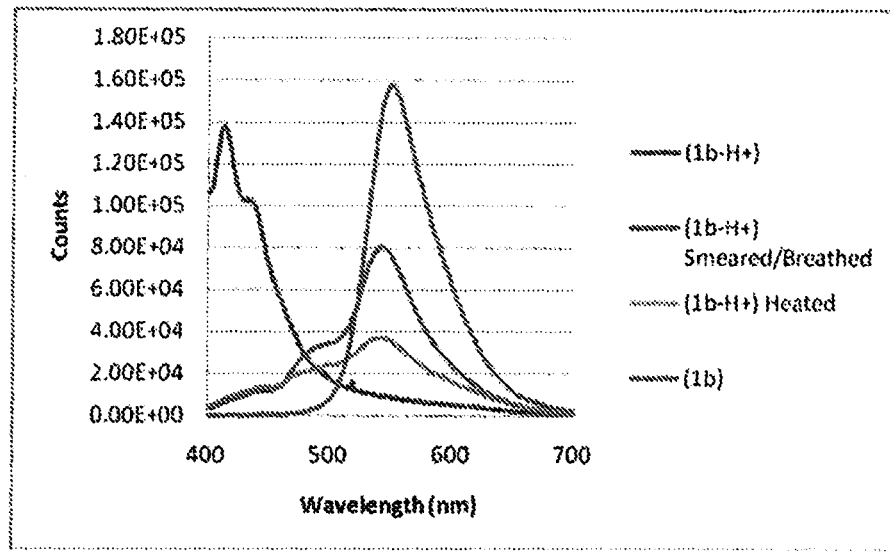
FIG. 17 shows emission spectra for (1b-H+), (1b-H+) Smeared/Breathed, (1b-H+) Heated, and (1b).

A round bottom flask and stir-bar was flame-dried three times while under vacuum. 0.073 g of (1a) was dissolved in DCM in the flask. The flask was purged under nitrogen for (1b minutes. Then, 0.06 mL room-temperature boron trifluoride etherate was added to the flask. Reaction was allowed to run at room temperature for 18 hours. Progress was measured using TLC. Reaction was stopped by rotovapping off solvent. Collected light tan precipitate; the protonated form of (1b), designated as (1b-H+) hereafter; via Buchner funnel filtration while trying to dissolve in DCM. The remaining solution was run through a silica gel column to obtain a flaky dark-orange solid. Purity was verified via ¹H NMR in d-chloroform. For these emission spectra, the solid state protonated form was sprinkled on a quartz cuvette and the spectra taken for (1b-H+). These sprinkles were then smeared with the tip of a clean nitrile glove and breathed on, and then another spectra was taken to get (1b-H+) Smeared/Breathed. The cuvette was then placed in a 110° C. oven for 10 min, and the spectra taken again to get (1b-H+) Heated. Finally, solid state (1b) was sprinkled on a clean quartz cuvette and the spectra taken to obtain the (1b) curve. Emission spectra follow the same naming system and the same procedure are provided in FIG. 17.

Synthesis of

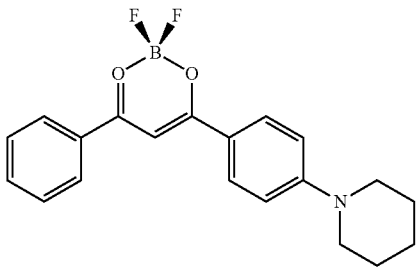

See "Dicarbonyl compounds, metal complexes with them, and light-emitting elements using either of them with high emission intensity", Fujii, Hiroyuki; Hirao, Shunichi; Sakurai, Hidehiro; Tani, Kazuyuki, Jpn. Kokai Tokkyo Koho (2005), JP2005035902 A 20050210.

Figure 18:
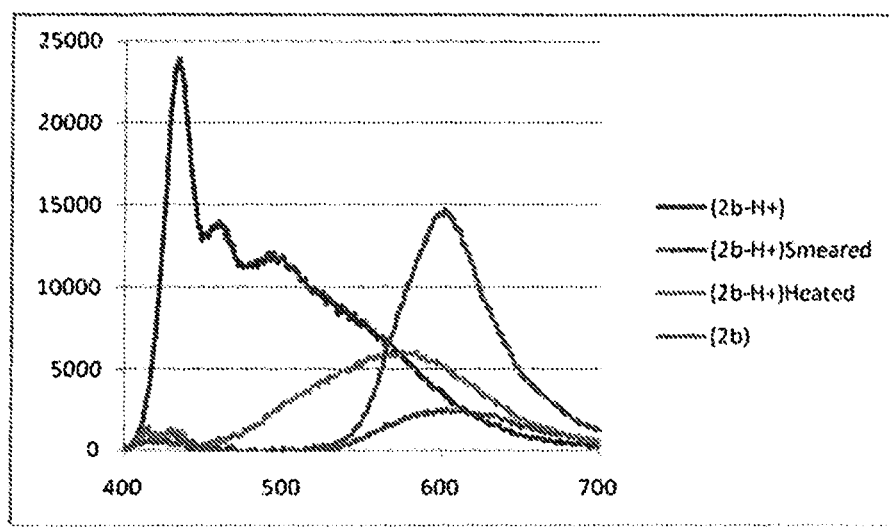
FIG. 18 shows emission spectra for (2b-H+), (2b-H+) Smeared, (2b-H+) Heated, and (2b).

This compound was prepared as above, with the following changes: 0.3999 g methyl benzoate and 0.4998 g 4-piperidinoacetophenone were used as the initial reagents. 1.8 mL of room-temperature 1.76 M LDA was added to start the reaction. Purification and purity verification were the same. The difluoroboronate complex was prepared as above, but using 0.1759 g of (2a) as the initial reagent and 0.107 mL of boron trifluoride etherate. (2b-H+) is a light orange powder and (2b) is red powder. For these spectra, only smearing was done, no breathing (see FIG. 18).

Synthesis of

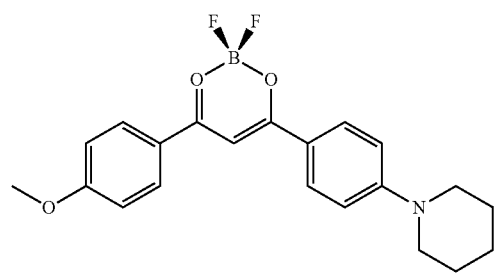

Figure 19:
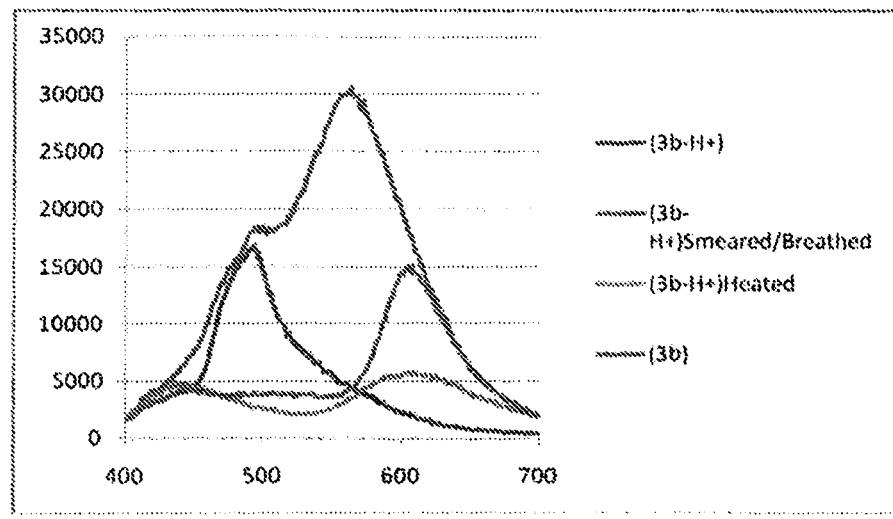
FIG. 19 shows emission spectra for (3b-H+), (3b-H+) Smeared/Breathed, (3b-H+) Heated, and (3b).

This was prepared as above, with the following changes. 4.506 g methyl 4-methoxybenzoate and 5.0218 g 4-piperidinoacetophenone were used as the initial reagents. 0.7803 g NaH suspended in THY was added dropwise to start the reaction. Purification and purity verification were the same. Formation of the difluoroboronate complex proceeded analogously, using 0.2005 g of (3a) as the initial reagent and 0.225 mL of boron trifluoride etherate. (3b-H-+) is a light yellow solid, and (3b) has a red crystalline solid form (see FIG. 19).

Synthesis of

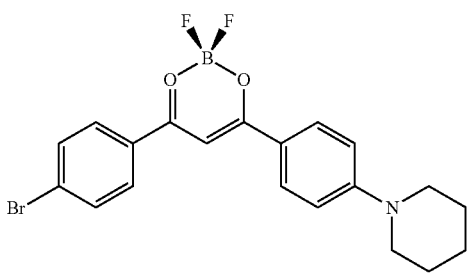

Figure 20:
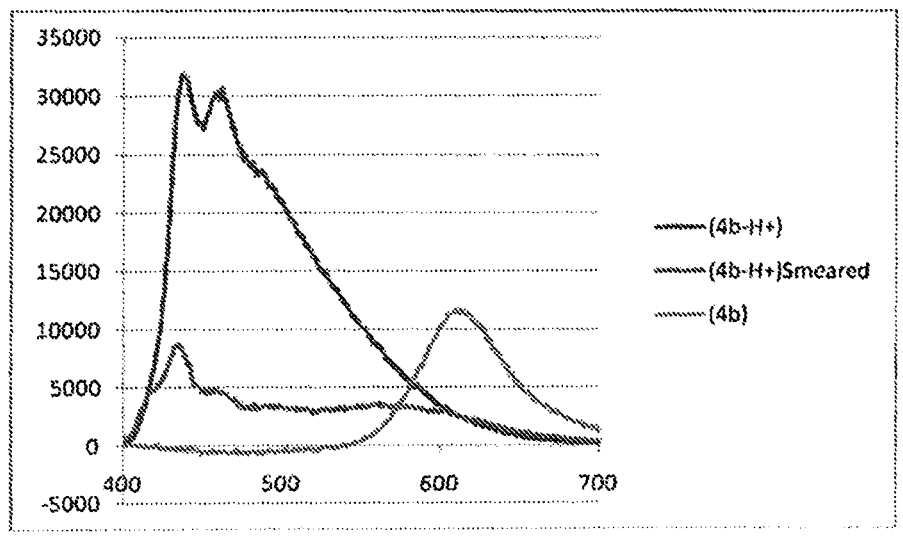
FIG. 20 shows emission spectra for (4b-H+), (4b-H+) Smeared, and (4b).

This was prepared as above with the following changes. 0.44 mL ethyl 4-bromobenzoate and 0.5008 g 4-piperidinoacetophenone were used as the initial reagents. 1.63 mL of room-temperature 1.76 M LDA was added to start the reaction. Purification and purity verification were the same. Formation of the difluoroboronate complex proceeded as above, but using 0.027 g of (3a) as the initial reagent and 0.019 mL of boron trifluoride etherate. (4b-H+) is a yellow-orange solid and (4b) is a reddish powder (see FIG. 20).

2-Naphthoyl benzoyl methane (nbm)

Acetophenone (500 mg, 4.12 mmol), methyl 2-naphthoate (1.03 g, 5.36 mmol) and THF (20 mL) were added sequentially to a 50 mL round bottom flask. After stirring the mixture for 10 min, a suspension containing NaH (167 mg, 6.61 mmol) in THF (10 mL) was added dropwise at room temperature under $N_2$. The mixture was stirred for 20 h before saturated aqueous $NaHCO_3$ (1 mL) was added to quench the reaction. THF was removed in vacuo before 1 M HCl (20 mL) was added. The aqueous phase was extracted with $CH_2Cl_2$ (3×20 mL). The combined organic layers were washed with distilled water (2×10 mL) and brine (10 mL), and dried over $Na_2SO_4$ before concentrated in vacuo. The residue was purified by column chromatography on silica gel eluting with hexanes/ethyl acetate (6:1) to give 2-naphthoyl benzoylmethane, thin, as a yellow solid: 700 mg (62%). $^1$H NMR (300 MHz, $CDCl_3$) δ 16.98 (s, 1H, ArCOH), 8.62 (s, 1H, 1'-ArH), 8.08-7.87 (m, 6H, 3', 4', 5', 2", 6"-ArH), 7.62-7.49 (m, 5H, 6',7'-ArH. 3", 4", 5"-ArH), 7.01 (s, 1H, COCHCO); MS (MALDI) m/z 275.13 (M+H$^+$), calcd m/z 275.11.

2-Anthracenoyl benzoyl methane (abm)

The anthracyl ligand was prepared from 2-acetyl anthracence (301 mg, 1.34 mmol.) and methyl benzoate (252 μL, 2.01 mmol) as described for nbm except that 3 equivalents of NaH were used and the reaction was refluxed for 12 h. After purification by column chromatography (3:1 hexanes/EtOAc to remove impurities, then $CH_2Cl_2$ to elute the product), the diketone, abm, was obtained as red solid: 362 mg (84%). $^1$H NMR (300 MHz, $CDCl_3$) δ 16.96 (s, 1H, ArCOH), 8.75 (s, 1H, 1'-ArH), 8.60 (s, 1H, 10'-ArH), 8.46 (s, 1H, 9'-ArH), 8.10-7.95 (m, 6H, 3', 4', 5', 8'-ArH. 2", 6"-ArH), 7.61-7.50 (m, 5H, 6',7'-ArH. 3", 4", 5"-ArH), 7.01 (s, 1H, COCHCO); MS (MALDI) m/z=324.07 (M+H$^+$), calcd m/z=324.12.

Difluoroboron-Diketonate Synthesis

A representative synthesis is provided for difluoroboron 2-naphthoyl benzoyl methane (BF$_2$nbm). Boron trifluoride diethyl etherate (88 μL, 0.70 mmol) was added to a solution of 2-naphthoyl benzoyl methane (191 mg, 0.70 mmol) in $CH_2Cl_2$ (20 mL) under $N_2$. After stirring the mixture at room temperature for 12 h, the solvent was removed in vacuo. (Note: Under reflux, boronation reactions are complete after ~1-2 h.) The residue was recrystallized from acetone to give difluoroboron 2-naphthoyl benzoyl methane, BF$_2$nbm, as a yellow powdery solid: 147 mg (65%). NMR (300 MHz, $CDCl_3$) δ 8.80 (s, 1H, 1'-ArH), 8.22 (d, J=8.1, 2H, 2", 6"-ArH), 8.10-7.92 (m, 4H, 3', 4', 5', 8'-ArH), 7.73-7.59 (m, 5H, 6', 7', 3", 4", 5"-ArH), 7.35 (s, 1H, COCHCO); MS (MALDI) m/z=345.00 (M+Na$^-$), calcd m/z=345.09.

Difluoroboron acetyl benzoyl methane, BF$_2$mbm

Pale yellow needle-like crystals precipitated from acetone/hexanes. NMR (300 MHz, $CDCl_3$) δ 8.08-8.04 (m, 2H, 2',6'-ArH), 7.72-7.66 (m, 1H, 4'-ArH), 7.56-7.50 (m, 2H, 3',5'-ArH), 6.59 (s, 1H, COCHCO), 2.42 (s, 3H, $CH_3CO$); MS (MALDI) m/z=233.02 (M+Na$^+$), calcd m/z=233.06.

Difluoroboron dibenzoyl methane, BF$_2$dbm

Pale yellow powder precipitated from acetone/hexanes. Data are in accord with literature values. $^1$H NMR (300 MHz, $CDCl_3$) δ 8.19-8.15 (m, 4H, 2', 6'-ArH, 2",6"-ArH), 7.74-7.68 (m, 2H, 4'-ArH, 4"-ArH), 7.60-7.54 (m, 4H, 3',5'-ArH, 3",5"-ArH), 7.21 (s, 1H, COCHCO); MS (MALDI) m/z=295.06 (M+Na$^-$), calcd m/z=295.07.

Difluoroboron 2-anthracenoyl benzoyl methane, BF$_2$abm

Boron trifluoride diethyl etherate (210 μA, 1.67 mmol) was added dropwise to a stirred solution of 2-anthracenoyl benzoyl methane (abm) (362 mg, 1.12 mmol) in $CH_2Cl_2$ (20 mL) under $N_2$. After stirring the mixture at room temperature for 12 h, saturated aqueous $NaHCO_3$ (1 mL) was added to quench the reaction. (Note: Under reflux, boronation reactions are complete after ~1-2 h.) The aqueous phase was extracted with $CH_2Cl_2$ (3×20 mL) and the combined organic layers were washed with distilled water (2×10 mL) and brine (10 mL), and dried over $Na_2SO_4$ before concentrated in vacuo. The residue was recrystallized from acetone to give difluoroboron 2-anthracenoyl benzoyl methane, BF$_2$abm, as a red powdery solid: 186 mg (42%). $^1$H NMR (300 MHz, $CDCl_3$) δ 9.02 (s, 1H, 1'-ArH), 8.65 (s, 1H, 9'-ArH), 8.47 (s, 1H, 10'-ArH), 8.23-7.97 (m, 6H, 3', 4', 5', 8'-ArH. 2", 6"-ArH), 7.74-7.52 (m, 5H, 6', 7', 3", 4", 5"-ArH), 7.36 (s, 1H, COCHCO); MS (MALDI) m/z=395.05 (M+Na$^+$), calcd m/z=395.10.

Synthesis of 4-alkoxyacetophenone

Two methods are used to synthesize the series of acetophenones. Below are the general procedures for each method:
Method A.
4-hydroxyacetophenone (5.0 g, 36.7 mmol) were dissolved in NaOH (aq) (1.5 g, 37.5 mmol, 100 mL $H_2O$) to obtain a clear, brown-yellow solution. The solution was then treated with 1-bromoalkane (40.4 mmol) and reflux. Upon completion, the reaction mixture was adjusted to pH ~12 by adding 1M NaOH solution, and allowed to cool down to room temperature. The aqueous solution was extracted with EtOAc (2×100 mL) and the combined organic layer was washed with sat. NaHCO$_3$ solution (2×100 mL), water (2×100 mL), and brine (2×100 mL), dried over anhydrous Na$_2$SO$_4$. Next, the organic layer was evaporated under vacuo and the resulting solid was vacuumed overnight.

4-propyloxyacetophenone (1.644 g, 25%). $\delta_H$ NMR (300 MHz, CDCl$_3$, ppm): 7.92 (2H, d, J9, Ar—H), 6.9 (2H, d, J9, Ar—H), 3.98 (2H, t, J 6, —OCH$_2$CH$_2$CH$_3$), 2.55 (3H, s, —C(O)CH$_3$), 1.89-1.77 (2H, m, —OCH$_2$CH$_2$CH$_3$), 1.05 (3H, t, J 7.5, —OCH$_2$CH$_2$CH$_3$).

4-hexyloxyacetophenone (5.1 g, 63%). $\delta_H$ NMR (300 MHz, CDCl$_3$, ppm): 7.92 (2H, d, J9, Ar—H), 6.92 (2H, d, J9, Ar—H), 4.01 (2H, t, J7.5, —OCH$_2$CH$_2$CH$_2$CH$_2$CH$_2$CH$_3$), 2.55 (3H, s, —C(O)CH$_3$), 1.85-1.75 (2H, m, —OCH$_2$CH$_2$CH$_2$CH$_2$CH$_2$CH$_3$), 1.5-1.31 (3×2 H, t, —OCH$_2$CH$_2$CH$_2$CH$_2$CH$_2$CH$_3$), 0.91 (3H, t, J7.5, —OCH$_2$CH$_2$CH$_2$CH$_2$CH$_2$CH$_3$).

4-hexadecyloxyacetophenone (1.96 g, 15%). $\delta_H$ NMR (300 MHz, CDCl$_3$, ppm): δ 7.92 (2H, d, J 9, Ar—H), 6.92 (2H, d, J 9, Ar—H), 4.01 (2H, t, J 6, —OCH$_2$—), 2.55 (3H, s, —C(O)CH$_3$), 1.80-1.75 (2H, m, —OCH$_2$CH$_2$—), 1.50-1.26 (alkyl protons, m, —OCH$_2$CH$_2$C$_n$H$_n$CH$_3$), 0.88 (3H, t, J 6, —OC$_n$H$_n$CH$_3$).

Method B.

A reaction mixture containing 4-hydroxyacetophenone, 1-bromoalkane, K$_2$CO$_3$, KI (ca. 0.35 g) in dried acetone (80 mL) was refluxed under N$_2$ and monitored by TLC. Upon completion, reaction mixture was filtered to remove all the insoluble materials. The resulting colorless solid was purified by redissolving in 1M NaOH solution (150 mL) and extracted with EtOAc (2×100 mL). The combined organic layer was washed with sat. NaHCO$_3$ solution (2×100 mL), water (2×100 mL), and brine (2×100 mL), dried over anhydrous Na$_2$SO$_4$. Finally, the organic layer was removed under vacuo and the solid was vacuumed overnight.

4-pentyloxyacetophenone (5.595 g, 78%). $\delta_H$ NMR (300 MHz, CDCl$_3$, ppm): 7.84 (2H, d, J9, Ar—H), 6.82 (2H, d, J9, Ar—H), 3.91 (2H, t, J 6, —OCH$_2$CH$_2$CH$_2$CH$_2$CH$_3$), 2.45 (3H, s, —C(O)CH$_3$), 1.76-1.67 (2H, m, —OCH$_2$CH$_2$CH$_2$CH$_2$CH$_3$), 1.41-1.21 (2×2 H, m, —OCH$_2$CH$_2$CH$_2$CH$_2$CH$_3$), 0.86 (3H, t, J 6, —OCH$_2$CH$_2$CH$_3$).

4-tetradecyloxyacetophenone (6.65 g, 75%). $\delta_H$ NMR (300 MHz, CDCl$_3$, ppm): δ 7.92 (2H, d, J 9, Ar—H), 6.92 (2H, d, J 9, Ar—H), 4.01 (2H, t, J 6, —OCH$_2$—), 2.55 (3H, s, —C(O)CH$_3$), 1.85-1.75 (2H, m, —OCH$_2$CH$_2$—), 1.5-1.26 (alkyl protons, m, —OCH$_2$CH$_2$C$_n$H$_n$CH$_3$), 0.88 (3H, t, J 6, —OC$_n$H$_n$CH$_3$).

4-octadecyloxyacetophenone (1.005 g, 10%). O$_H$ NMR (300 MHz, CDCl$_3$, ppm): δ 7.92 (2H, d, J 9, Ar—H), 6.92 (2H, d, J 9, Ar—H), 4.01 (2H, t, J 6, —OCH$_2$—), 2.55 (3H, s, —C(O)CH$_3$), 1.85-1.75 (2H, m, —OCH$_2$CH$_2$—), 1.48-1.26 (alkyl protons, m, —OCH$_2$CH$_2$C$_n$H$_n$CH$_3$), 0.88 (3H, t, J 6, —OC$_n$H$_n$CH$_3$).

Synthesis of p-Diketones

The β-diketone ligands were prepared by Claisen condensation using NaH as deprotonating base as previously described. Briefly, 4-alkoxyacetophenone (2.5 mmol), methyl benzoate (1.2 equiv) and THF (~20 mL) were added sequentially to a 50 mL round bottom flask, previously dried in the oven overnight and backfilled with N$_2$. After stirring the mixture for 10 min, a suspension containing NaH (1.5 equiv) in THF (10 mL) was added dropwise at room temperature under N$_2$. The mixture was refluxed overnight before saturated aqueous NaHCO$_3$ (1 mL) was added to quench the reaction, followed by addition of 1M HCl solution to adjust the pH to ~1. THF was removed in vacuo and the aqueous solution was extracted with CH$_2$Cl$_2$ (3×20 mL). The combined organic layers were washed with distilled water (2×10 mL) and brine (2×10 mL), and dried over Na$_2$SO$_4$ before concentration in vacuo. The resulting solid was chromatographied (silica, hexanes/ethyl acetate) DdmOC$_2$H$_5$. Yellow solid (0.467 g, 68%). O$_H$ NMR (300 MHz, CDCl$_3$, ppm) 17.00 (1H, s, OH), 7.98 (2×2H, d, J 9, Ar—H), 7.56-7.46 (3H, m, Ar—H), 6.96 (2H, d, J9, Ar—H), 6.80 (1H, s, Ar—C(O)—CH=C(OH)—Ar), 4.12 (2H, quartet, J 6, —OCH$_2$CH$_3$), 1.46 (3H, t, J 7.5, —OCH$_2$CH$_3$); m/z (MALDI-TOF) expected 268.11. found 269.08 (100) [M+H]$^+$, 291.07 (30) [M+Na]$^+$.

DdmOC$_3$H$_7$ (0.495 g, 70%). $\delta_H$ NMR (300 MHz, CDCl$_3$, ppm): 17.00 (1H, s, OH), 7.97 (2×2H, d, J 9, Ar—H), 7.54-7.46 (3H, m, Ar—H), 6.97 (2H, d, J 9, Ar—H), 6.80 (1H, s, Ar—C(O)—CH=C(OH)—Ar), 4.0 (2H, t, J 6, —OCH$_2$CH$_2$CH$_3$), 1.91-1.76 (2H, m, J 6, —OCH$_2$CH$_2$CH$_3$ 1.06 (3H, t, J 7.5, —OCH$_2$CH$_2$CH$_3$); m/z (MALDI-TOF) expected 282.13. found 283.07 [M+H]$^+$, 305.05 [M+Na]$^+$.

DdmOC$_5$H$_{11}$ (0.387 g, 50%). $\delta_H$ NMR (300 MHz, CDCl$_3$, ppm): 17.01 (1H, s, OH), 7.97 (2×2H, d, J9, Ar—H), 7.54-7.46 (3H, m, Ar—H), 6.66 (2H, d, J 9, Ar—H), 6.80 (1H, s, Ar—C(O)—CH=C(OH)—Ar), 4.04 (2H, t, J 6, —OCH$_2$CH$_2$CH$_2$CH$_2$CH$_3$), 1.87-1.78 (2H, m, J 6, —OCH$_2$CH$_2$CH$_2$CH$_2$CH$_3$), 1.52-1.34 (alkyl protons, m, —OCH$_2$CH$_2$CH$_2$CH$_2$CH$_3$), 0.95 (3H, t, J 7.5, —OCH$_2$CH$_2$CH$_2$CH$_2$CH$_3$); m/z expected 310.16. found 311.09 [M+H]$^+$.

DdmOC$_{14}$H$_{29}$ (0.519 g, 47%). $\delta_H$ NMR (300 MHz, CDCl$_3$, ppm): 17.00 (1H, s, OH), 7.96 (2×2H, d, J9, Ar—H), 7.54-7.48 (3H, m, Ar—H), 6.97 (2H, d, J 9, Ar—H), 6.80 (1H, s, Ar—C(O)—CH=C(OH)—Ar), 4.03 (2H, t, J 6, —OCH$_2$CH$_2$C$_n$H$_n$CH$_3$), 1.86-1.77 (2H, m, J 6, —OCH$_2$CH$_2$C$_n$H$_n$CH$_3$), 1.48-1.26 (alkyl protons, m, —OCH$_2$CH$_2$C$_n$H$_n$CH$_3$), 0.88 (3H, t, J 7.5, —OCH$_2$CH$_2$C$_n$H$_n$CH$_3$); m/z (MALDI-TOF) expected 436.30. found 437.22 [M+H]$^+$, 459.19 [M+Na]$^+$.

DdmOC$_{/6}$H$_{33}$ (59 mg) $\delta_H$ NMR (300 MHz, CDCl$_3$, ppm): 17.01 (1H, s, OH), 7.96 (2×2H, d, J 9, Ar—H), 7.54-7.45 (3H, m, Ar—H), 6.97 (2H, d, J9, Ar—H), 6.80 (1H, s, Ar—C(O)—CH═C(OH)—Ar), 4.03 (2H, t, J 6, —OCH$_2$CH$_2$C$_n$H$_n$CH$_3$), 1.86-1.77 (2H, m, J 6, —OCH$_2$CH$_2$C$_n$H$_n$CH$_3$), 1.47-1.26 (alkyl protons, m, —OCH$_2$CH$_2$C$_n$H$_n$CH$_3$), 0.88 (3H, t, J 7.5, —OCH$_2$CH$_2$C$_n$H$_n$CH$_3$); m/z (MALDI-TOF) expected 464.33. found 465.25 [M+H]$^+$.

DdmOC$_{18}$H$_{37}$ (1.070 g, 87%) $\delta_H$ NMR (300 MHz, CDCl$_3$, ppm): 17.01 (1H, s, OH), 7.96 (2×2H, d, J9, Ar—H), 7.54-7.45 (3H, m, Ar—H), 6.97 (2H, d, J 9, Ar—H), 6.80 (1H, s, Ar—C(O)—CH═C(OH)—Ar), 4.03 (2H, t, J 6, —OCH$_2$CH$_2$C$_n$H$_n$CH$_3$), 1.86-1.77 (2H, m, J 6, —OCH$_2$CH$_2$C$_n$H$_n$CH$_3$), 1.47-1.26 (alkyl protons, m, —OCH$_2$CH$_2$C$_n$H$_n$CH$_3$), 0.88 (3H, t, J 7.5, —OCH$_2$CH$_2$C$_n$H$_n$CH$_3$); m/z (MALDI-TOF) expected 492.36. found 493.30 [M+H]$^+$.

Difluoroboron-Diketonate Complex Synthesis

To a solution of DbmOC$_n$H$_{2n+1}$ (0.43 mmol) in 20 mL CH$_2$Cl$_2$, boron trifluoride diethyl etherate (81 µL, 0.64 mmol) was added at room temperature under N$_2$. The reaction was allowed to run at room temperature overnight. Upon completion, the reaction mixture was ran through a silica plug (CH$_2$Cl$_2$) and then chromatographied (silica, Hexanes/CH$_2$Cl$_2$) or precipitated by adding excess hexane, followed by vacuum filtration to obtain the solid. The resulting solid was further purified by recrystallization in CH$_2$Cl$_2$/Hexanes.

BF$_2$dbmOC$_2$H$_5$

Yellow solid (0.594 g). $\delta_H$ NMR (300 MHz, CDCl$_3$, ppm): 8.14 (2×2H, overlap), 7.67 (1H, t, J 7.5, Ar—H), 7.55 (2H, t, J 9, Ar—H), 7.1 (1H, s, Ar—C(O)—CH═C(OH)—Ar), 7.2 (2H, d, J 9, Ar—H), 4.17 (2H, quartet, J 6, —OCH$_2$CH$_3$), 1.48 (3H, t, J 6, —OCH$_2$CH$_3$); m/z expected 316.11. found 339.03 [M+Na]$^+$. UV-Vis: $\lambda_{max}$ (CH$_2$Cl$_2$)/nm 399 ($\epsilon$/M$^{-1}$ cm$^{-1}$ 65 100). Fluorescence spectroscopy: $\lambda_{exc}$=350 nm, $\lambda_{em}$=436 nm, $\Phi_f$=0.91, $\tau_f$=2.04 ns.

BF$_2$dbmOC$_3$H$_7$

Yellow solid (336 mg, 89%). $\delta_H$ NMR (300 MHz, CDCl$_3$, ppm): 8.14 (2×2H, overlap), 7.67 (1H, t, J7.5, Ar—H), 7.54 (2H, d, J9, Ar—H), 7.1 (1H, s, Ar—C(O)—CH═C(O—BF$_2$)—Ar), 7.03 (2H, d, J 9, Ar—H), 4.05 (2H, t, J 6, —OCH$_2$CH$_2$CH$_3$), 1.93-1.81 (2H, m, J 6, —OCH$_2$CH$_2$CH$_3$), 1.07 (3H, t, J7.5, —OCH$_2$CH$_2$CH$_3$); m/z (MALDI-TOF) expected 330.12. found 353.04 [M+Na]$^+$. UV-Vis: $\lambda_{max}$ (CH$_2$Cl$_2$)/nm 398 ($\epsilon$/M$^{-1}$ cm$^{-1}$ 51 000). Fluorescence spectroscopy: $\lambda_{em}$=435 nm ($\lambda_{exc}$=350 nm), $\Phi_f$=1.00, $\tau_f$=2.10 ns.

BF$_2$dbmOC$_5$H$_{11}$

Yellow solid (237 mg, 61%). $\delta_H$ NMR (300 MHz, CDCl$_3$, ppm): 8.14 (2×2H, overlap), 7.67 (1H, t, J7.5, Ar—H), 7.54 (2H, d, J9, Ar—H), 7.1 (1H, s, Ar—C(O)—CH═C(O—BF$_2$)—Ar), 7.02 (2H, d, J 9, Ar—H), 4.08 (2H, t, J 6, —OCH$_2$CH$_2$C$_n$H$_n$CH$_3$), 1.89-1.80 (2H, m, J 6, —OCH$_2$CH$_2$C$_n$H$_n$CH$_3$), 1.44 (4H, br. m, —OCH$_2$CH$_2$C$_2$H$_4$—CH$_3$), 0.95 (3H, t, J 7.5, —OCH$_2$CH$_2$C$_2$H$_4$—CH$_3$); m/z (MALDI-TOF) expected 358.16. found 381.07 [M+Na]$^+$. UV-Vis: $\lambda_{max}$(CH$_2$Cl$_2$)/nm 398 ($\epsilon$/M$^{-1}$ cm$^{-1}$ 51 000). Fluorescence spectroscopy: $\lambda_{em}$=436 nm ($\lambda_{exc}$=350 nm), D=1.00, $\tau_f$=2.03 ns.

BF$_2$dbmOC$_6$H$_{13}$

Yellow solid (0.862 g, 92%). $\delta_H$ NMR (300 MHz, CDCl$_3$, ppm): 8.14 (2×2H, overlap), 7.67 (1H, t, J 7.5, Ar—H), 7.54 (2H, d, J9, Ar—H), 7.1 (1H, s, Ar—C(O)—CH═C(O—BF$_2$)—Ar), 7.02 (2H, d, J 9, Ar—H), 4.08 (2H, t, J6, —OCH$_2$CH$_2$C$_n$H$_n$CH$_3$), 1.88-1.79 (2H, m, J 6, —OCH$_2$CH$_2$C$_n$H$_n$CH$_3$), 1.55-1.34 (alkyl protons, m, —OCH$_2$CH$_2$C$_n$H$_n$CH$_3$), 0.92 (3H, t, J 7.5, —OCH$_2$CH$_2$C$_n$H$_n$CH$_3$); m/z (MALDI-TOF) expected 372.17. found 395.09 [M+Na]$^+$. UV-Vis: $\lambda_{max}$(CH$_2$Cl$_2$)/nm 399 ($\epsilon$/m$^{-1}$ cm$^{-1}$ 53 100). Fluorescence spectroscopy: $\lambda_{em}$=437 nm ($\lambda_{exc}$=350 nm), $\Phi_f$=1.00, $\tau_f$=2.04 ns.

BF$_2$dbmOC$_{14}$H$_{29}$

Yellow solid (0.484 g, 66%). $\delta_H$ NMR (300 MHz, CDCl$_3$, ppm): 8.14 (2×2H, overlap), 7.67 (1H, t, J7.5, Ar—H), 7.55 (2H, d, J9, Ar—H), 7.1 (1H, s, Ar—C(O)—CH═C(O—BF$_2$)—Ar), 7.02 (2H, d, J9, Ar—H), 4.08 (2H, t, J 6, —OCH$_2$CH$_2$C$_n$H$_n$CH$_3$), 1.88-1.79 (2H, m, J 6, —OCH$_2$CH$_2$C$_n$H$_n$CH$_3$), 1.50-1.26 (alkyl protons, m, —OCH$_2$CH$_2$C$_n$H$_n$CH$_3$), 0.88 (3H, t, J 7.5, —OCH$_2$CH$_2$C$_n$H$_n$CH$_3$); m/z (MALDI-TOF) expected 484.30. found 507.20 [M+Na]$^+$. UV-Vis: $\lambda_{max}$(CH$_2$Cl$_2$)/nm 398 ($\epsilon$/m$^{-1}$ cm$^{-1}$ 66 200). Fluorescence spectroscopy: $\lambda_{em}$=437 nm ($\lambda_{exc}$=350 nm), $\Phi_f$=0.94, $\tau_f$=2.02 ns.

BF$_2$dbmOC$_{16}$H$_{33}$

Yellow solid (88 mg). $\delta_H$ NMR (300 MHz, CDCl$_3$, ppm): 8.14 (2×21-1, overlap), 7.67 (1H, t, J7.5, Ar—H), 7.55 (2H, d, J9, Ar—H), 7.10 (1H, s, Ar—C(O)—CH═C(O—BF$_2$)—Ar), 7.00 (2H, d, J 9, Ar—H), 4.08 (2H, t, J 6, —OCH$_2$CH$_2$C$_n$H$_n$CH$_3$), 1.86-1.78 (2H, m, J 6, —OCH$_2$CH$_2$C$_n$H$_n$CH$_3$), 1.48-1.26 (alkyl protons, m, —OCH$_2$CH$_2$C$_n$H$_n$CH$_3$), 0.88 (3H, t, J 7.5, —OCH$_2$CH$_2$C$_n$H$_n$CH$_3$); m/z (MALDI-TOF) expected 512.13. found 535.21 [M+Na]$^+$. UV-Vis: $\lambda_{max}$(CH$_2$Cl$_2$)/nm 399 ($\epsilon$/m$^{-1}$ cm$^{-1}$ 70 800). Fluorescence spectroscopy: $\lambda_{em}$=438 nm ($\lambda_{exc}$=350 nm), $\Phi_f$=0.82, $\tau_f$=2.05.

BF$_2$dbmOC$_{18}$H$_{37}$

Yellow solid (0.862 g, 92%). $\delta_H$ NMR (300 MHz, CDCl$_3$, ppm): 8.14 (2×2H, overlap), 7.67 (1H, t, J 7.5, Ar—H), 7.55 (2H, d, J 9, Ar—H), 7.1 (1H, s, Ar—C(O)—CH═C(O—BF$_2$)—Ar), 7.02 (2H, d, J 9, Ar—H), 4.08 (2H, t, J 6, —OCH$_2$CH$_2$C$_n$H$_n$CH$_3$), 1.88-1.79 (2H, m, J 6, —OCH$_2$CH$_2$C$_n$H$_n$CH$_3$), 1.48-1.26 (alkyl protons, m, —OCH$_2$CH$_2$C$_n$H$_n$CH$_3$), 0.88 (3H, t, J 7.5, —OCH$_2$CH$_2$C$_n$H$_n$CH$_3$); m/z (MALDI-TOF) expected 540.36. found 563.23 [M+Na]$^+$. UV-Vis: $\lambda_{max}$(CH$_2$Cl$_2$)/nm 399 ($\epsilon$/M$^{-1}$ cm$^{-1}$ 83 800). Fluorescence spectroscopy: $\lambda_{em}$=436 nm ($\lambda_{exc}$=350 nm), $\Phi_f$=1.00, $\tau_f$=2.02.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A composition comprising a mechanochromic luminescent solid-state form of a difluoroboron β-diketonate of formula

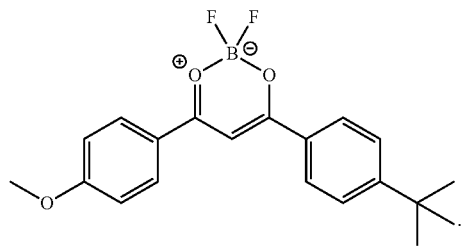 [SMILES: COc1ccc(C2=[O+][B-](F)(F)OC(c3ccc(C(C)(C)C)cc3)=C2)cc1]

2. A composition comprising a difluoroboron β-diketonate of a formula selected from:

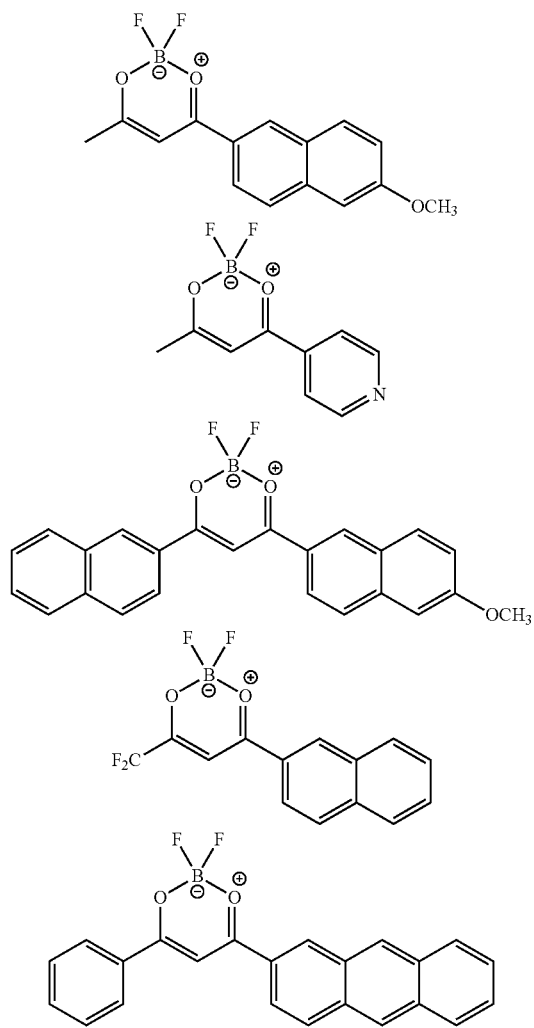

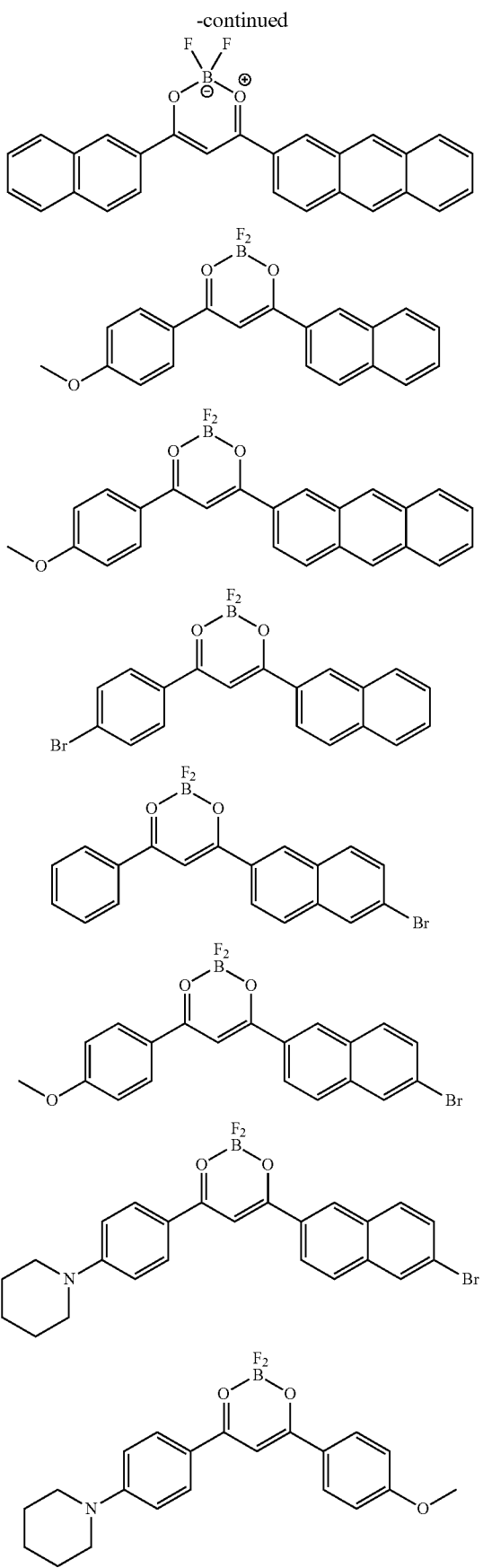

-continued

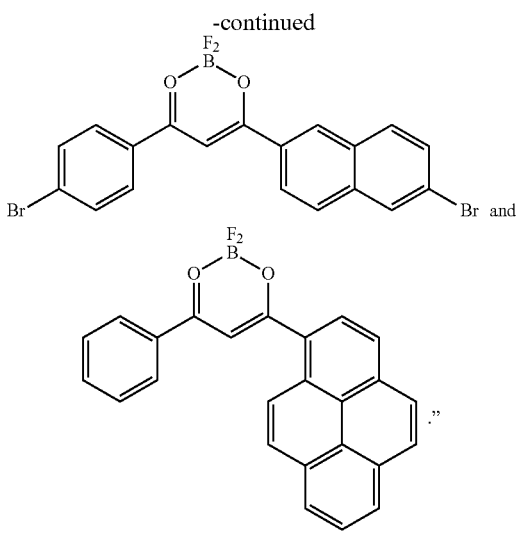

3. A solid-state mechanochromic luminescent composition comprising a mechanochromic luminescent solid-state form of a difluoroboron β-diketonate of formula (I)

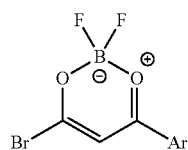
(I)

wherein
R is alkyl, alkenyl, alkynyl, cycloalkyl, or cycloalkylalkyl, wherein any alkyl, alkenyl, alkynyl, cycloalkyl, or cycloalkylalkyl is optionally substituted with 1-5 independently selected J groups; or R is Ar; wherein each Ar is an independently selected aryl, arylalkenyl, arylalkynyl, heteroaryl, heteroarylalkenyl, or heteroarylalkynyl group, wherein any aryl or heteroaryl can be monocyclic or polycyclic, and is optionally substituted with 1-5 independently selected J groups;

J is F, Cl, Br, I, OR', OC(O)N(R')$_2$, CN, NO, NO$_2$, ONO$_2$, N$_3$, CF$_3$, OCF$_3$, R', N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R'), N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with F, Cl, Br, I, CN, NO, NO$_2$, ONO$_2$, N$_3$, CF$_3$, OCF$_3$, hydrogen, alkyl, cycloalkyl, aryl, aralkyl, heterocyclyl, heteroaryl, or heteroarylalkyl; or wherein two R' groups bonded to a nitrogen atom or to adjacent nitrogen atoms can together with the nitrogen atom or atoms form a heterocyclyl, which can be mono- or independently multi-substituted with F, Cl, Br, I, CN, NO, NO$_2$, ONO$_2$, N$_3$, CF$_3$, OCF$_3$, hydrogen, alkyl, cycloalkyl, aryl, aralkyl, heterocyclyl, heteroaryl, or heteroarylalkyl;

or any salt thereof, with the provisos
A) that when R is 4-methoxyphenyl, Ar is not 4-methoxyphenyl, 4-fluorophenyl, or 4-trifluoromethylphenyl,
B) that when R is 4-trifluoromethylphenyl, Ar is not 4-methylphenyl,
C) that when R is methyl, Ar is not phenyl,
D) that when R is 4-(2-hydroxyethoxy)phenyl, Ar is not phenyl, and
E) that when R is trifluoromethyl, Ar is not thiophene,
F) that when R is alkenyl substituted with dialkylaminophenyl, Ar is not phenyl and a second light-absorbing or luminescing material, and, optionally, additional light-absorbing or luminescing materials, wherein the second luminescent material comprises Rhodamine B.

4. A biological sensor or assay comprising a solid-state mechanochromic luminescent composition comprising a mechanochromic luminescent solid-state form of a difluoroboron β-diketonate of formula (I)

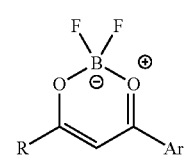
(I)

wherein
R is alkyl, alkenyl, alkynyl, cycloalkyl, or cycloalkylalkyl, wherein any alkyl, alkenyl, alkynyl, cycloalkyl, or cycloalkylalkyl is optionally substituted with 1-5 independently selected J groups; or R is Ar; wherein each Ar is an independently selected aryl, arylalkenyl, arylalkynyl, heteroaryl, heteroarylalkenyl, or heteroarylalkynyl group, wherein any aryl or heteroaryl can be monocyclic or polycyclic, and is optionally substituted with 1-5 independently selected J groups;

J is F, Cl, Br, I, OR', OC(O)N(R')$_2$, CN, NO, NO$_2$, ONO$_2$, N$_3$, CF$_3$, OCF$_3$, R', N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with F, Cl, Br, I, CN, NO, NO$_2$, ONO$_2$, N$_3$, CF$_3$, OCF$_3$, hydrogen, alkyl, cycloalkyl, aryl, aralkyl, heterocyclyl, heteroaryl, or heteroarylalkyl; or wherein two R' groups bonded to a nitrogen atom or to adjacent nitrogen atoms can together with the nitrogen atom or atoms form a heterocyclyl, which can be mono- or independently multi-substituted with F, Cl, Br, I, CN, NO, NO$_2$, ONO$_2$, N$_3$, CF$_3$, OCF$_3$, hydrogen, alkyl, cycloalkyl, aryl, aralkyl, heterocyclyl, heteroaryl, or heteroarylalkyl;

or any salt thereof, with the provisos
A) that when R is 4-methoxyphenyl, Ar is not 4-methoxyphenyl, 4-fluorophenyl, or 4-trifluoromethylphenyl,
B) that when R is 4-trifluoromethylphenyl, Ar is not 4-methylphenyl,
C) that when R is methyl, Ar is not phenyl,
D) that when R is 4-(2-hydroxyethoxy)phenyl, Ar is not phenyl, and
E) that when R is trifluoromethyl, Ar is not thiophene,
F) that when R is alkenyl substituted with dialkylaminophenyl, Ar is not phenyl and a second light-absorbing or luminescing material, and, optionally, additional light-absorbing or luminescing materials.
5. A composition comprising a mechanochromic luminescent solid-state form of a difluoroboron β-diketonate, wherein the difluoroboron β-diketonate has a formula selected from:
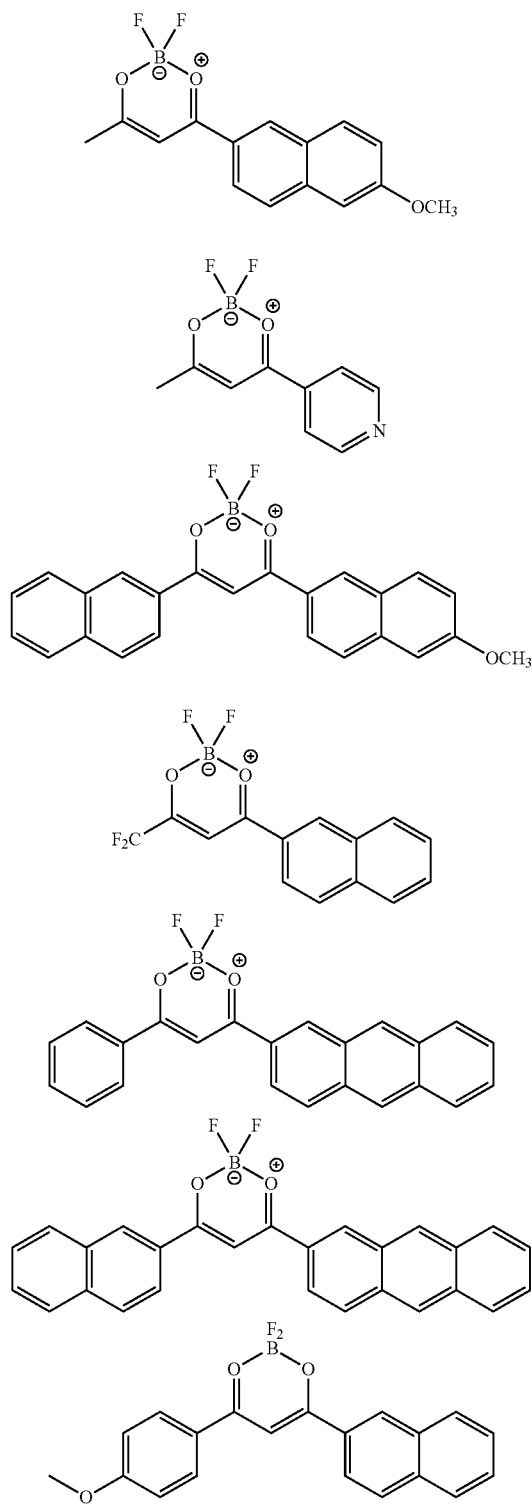
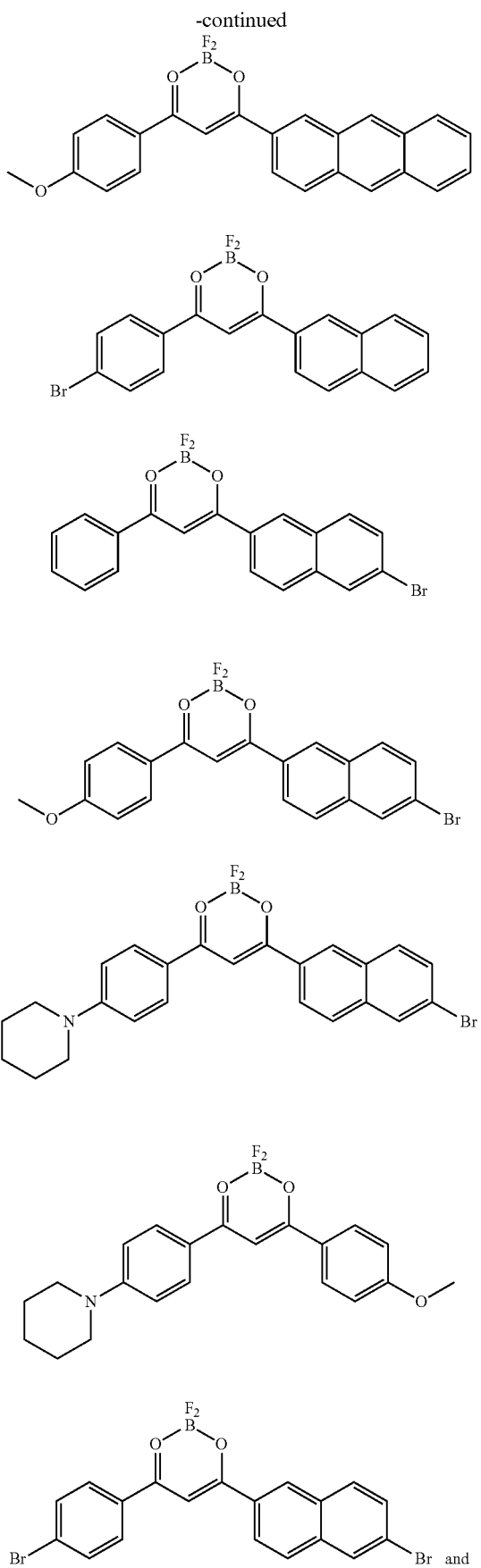

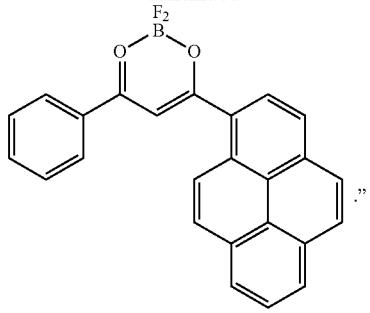
6. A composition comprising a mechanochromic luminescent solid-state form of a difluoroboron β-diketonate, wherein the difluoroboron β-diketonate has a formula selected from:
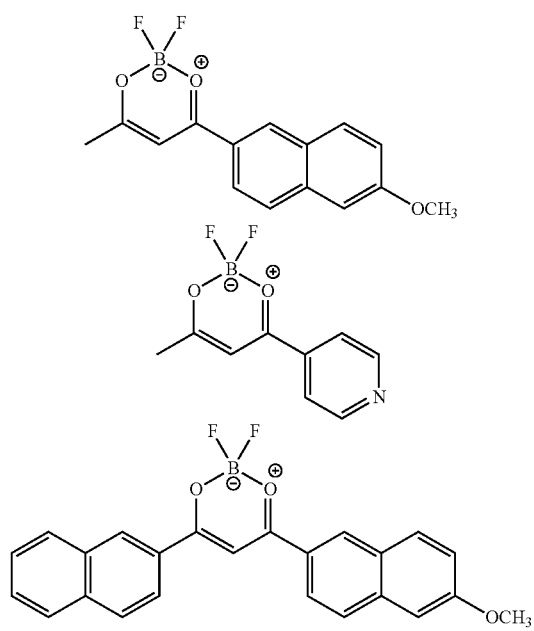
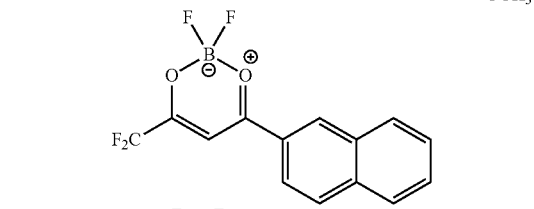
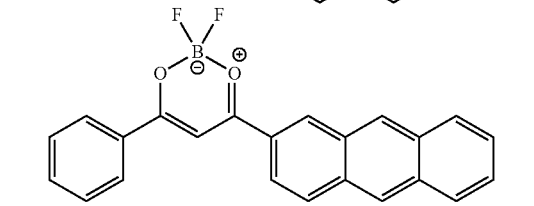
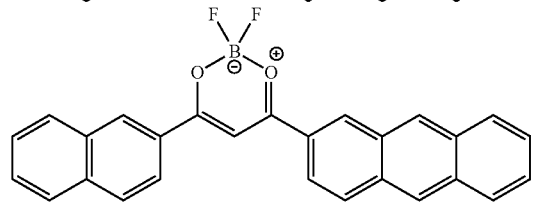
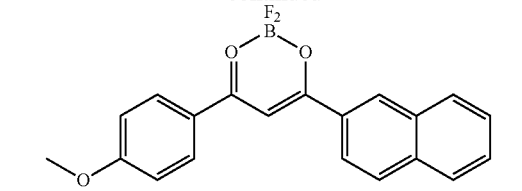
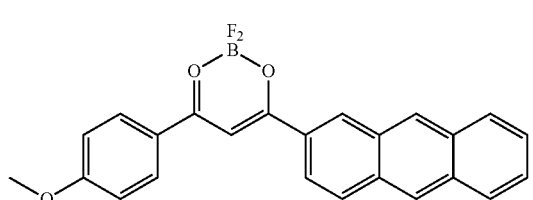
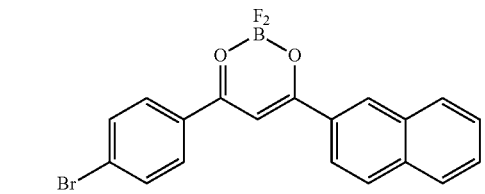
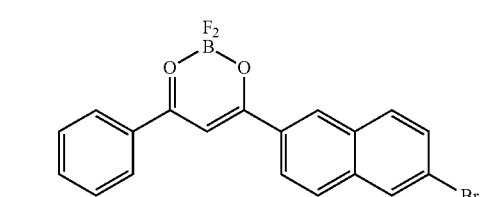
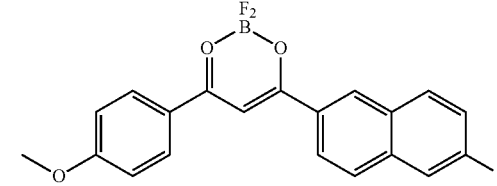
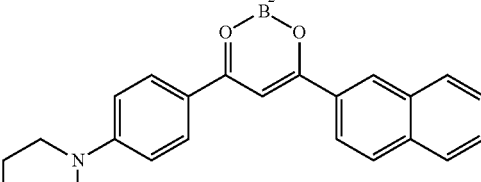
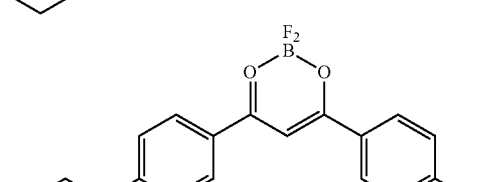
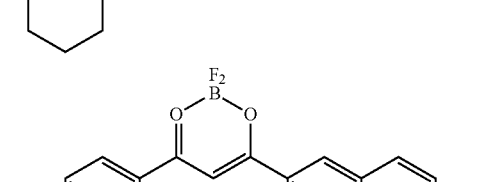
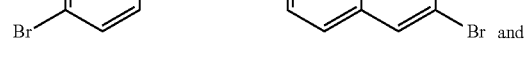

-continued

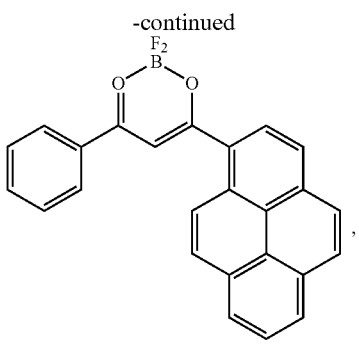

wherein the solid-state form is an amorphous film.

7. The composition of claim 6 wherein the film is spin-cast.

8. The composition of claim 5 wherein the solid-state form is crystalline.

9. The composition of claim 5 wherein the mechanochromic effect on the luminescence is induced by a pressure of at least about 1 gm/cm$^2$, or at least 10 gm/cm$^2$, or at least 100 gm/cm$^2$ on the solid-state form.

10. The composition of claim 5 wherein luminescence of a mechanically perturbed portion of the composition, wherein the composition comprises a heavy atom, is quenched by the presence of oxygen or another quenching agent.

11. The composition of claim 9 wherein the mechanochromic effect on the luminescence is reversible.

12. A composition comprising a mechanochromic luminescent solid-state form of a difluoroboron β-diketonate of formula (I)

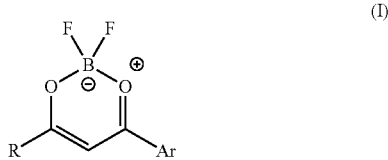

wherein
R is alkyl, alkenyl, alkynyl, cycloalkyl, or cycloalkylalkyl, wherein any alkyl, alkenyl, alkynyl, cycloalkyl, or cycloalkylalkyl is optionally substituted with 1-5 independently selected J groups; or R is Ar; wherein each Ar is an independently selected aryl, arylalkenyl, arylalkynyl, heteroaryl, heteroarylalkenyl, or heteroarylalkynyl group, wherein any aryl or heteroaryl can be monocyclic or polycyclic, and is optionally substituted with 1-5 independently selected J groups;
J is F, Cl, Br, I, OR', OC(O)N(R')$_2$, CN, NO, NO$_2$, ONO$_2$, N$_3$, CF$_3$, OCF$_3$, R', N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with F, Cl, Br, I, CN, NO, NO$_2$, ONO$_2$, N$_3$, CF$_3$, OCF$_3$, hydrogen, alkyl, cycloalkyl, aryl, aralkyl, heterocyclyl, heteroaryl, or heteroarylalkyl; or wherein two R' groups bonded to a nitrogen atom or to adjacent nitrogen atoms can together with the nitrogen atom or atoms form a heterocyclyl, which can be mono- or independently multi-substituted with F, Cl, Br, I, CN, NO, NO$_2$, ONO$_2$, N$_3$, CF$_3$, OCF$_3$, hydrogen, alkyl, cycloalkyl, aryl, aralkyl, heterocyclyl, heteroaryl, or heteroarylalkyl;
or any salt thereof, with the provisos
A) that when R is 4-methoxyphenyl, Ar is not 4-methoxyphenyl, 4-fluorophenyl, or 4-trifluoromethylphenyl,
B) that when R is 4-trifluoromethylphenyl, Ar is not 4-methylphenyl,
C) that when R is methyl, Ar is not phenyl,
D) that when R is 4-(2-hydroxyethoxy)phenyl, Ar is not phenyl, and
E) that when R is trifluoromethyl, Ar is not thiophene,
F) that when R is alkenyl substituted with dialkylaminophenyl, Ar is not phenyl
wherein the solid-state form is an amorphous film.

13. The composition of claim 12 wherein the film is spin-cast.

14. The biological sensor or assay of claim 4, wherein the solid-state form is an amorphous film.

15. The biological sensor or assay of claim 14 wherein the film is spin-cast.

16. The biological sensor or assay of claim 4 wherein the solid-state form is crystalline.

17. The biological sensor or assay of claim 16 wherein each of a plurality of crystalline forms of the compound of formula (I) each has a luminescence emission spectrum that is distinct from at least one of a different crystalline form.

18. The biological sensor or assay of claim 4 wherein the mechanochromic effect on the luminescence is induced by a pressure of at least about 1 gm/cm$^2$, or at least 10 gm/cm$^2$, or at least 100 gm/cm$^2$ on the solid-state form.

19. The biological sensor or assay of claim 4 wherein luminescence of a mechanically perturbed portion of the composition, wherein the composition comprises a heavy atom, is quenched by the presence of oxygen or another quenching agent.

20. The biological sensor or assay of claim 18 wherein the mechanochromic effect on the luminescence is reversible.

21. The biological sensor or assay of claim 20 wherein the mechanochromic effect on the luminescence is thermally reversible.

22. The biological sensor or assay of claim 20 wherein the mechanochromic effect on the luminescence is thermally reversible at a temperature of about 20° C. over a period of time of about 1 second to about 24 hours.

23. The biological sensor or assay of claim 4 disposed within or external to a living cell, tissue, or organism, wherein the mechanochromic effect on the luminescence is induced by a mechanical perturbation induced within or external to the living cell, tissue, or organism.

24. The biological sensor or assay of claim 23 wherein a pressure or tension of at least about 0.1 to at least about 5 kilopascals (kPa) is exerted within or external to the cell, tissue, or organism.

25. The biological sensor or assay of claim 4 wherein a luminescence light emission band is more narrow than a luminescence light emission band from the respective difluoroboron β-diketonate of formula (I) in solution, or wherein the luminescence light emission band of the composition of claim 1 is bathochromically shifted with respect to a luminescence light emission band from the respective difluoroboron β-diketonate of formula (I) in solution, or both.

26. The biological sensor or assay of claim 4 wherein for the compound of formula (I), R is alkyl or fluoroalkyl.

27. The biological sensor or assay of claim 4 wherein for the compound of formula (I), R is aryl or heteroaryl, optionally substituted with 1-5 independently selected J groups.

* * * * *